US012698289B2

(12) United States Patent
Lu et al.

(10) Patent No.: US 12,698,289 B2
(45) Date of Patent: Aug. 4, 2026

(54) SOLID FORMS OF PHARMACEUTICALLY ACCEPTABLE SALTS OF (S)-(2-ETHYL-5-FLUORO-4-HYDROXYPHENYL)-1H-INDAZOL-3-YL)-4,6-DIHYDROPYRROLO [3,4-D]IMIDAZOL-5(1H)-YL)(3-HYDROXYPYRROLIDIN-1-YL)METHANONE AS JAK INHIBITORS

(71) Applicant: HENAN MEDINNO PHARMACEUTICAL TECHNOLOGY CO., LTD., Zhengzhou (CN)

(72) Inventors: Liang Lu, Zhengzhou (CN); Saisai Zhao, Zhengzhou (CN)

(73) Assignee: HENAN MEDINNO PHARMACEUTICAL TECHNOLOGY CO., LTD. (CN)

( * ) Notice: Subject to any disclaimer, the term of this patent is extended or adjusted under 35 U.S.C. 154(b) by 672 days.

(21) Appl. No.: 18/168,874

(22) Filed: Feb. 14, 2023

(65) Prior Publication Data

US 2023/0192710 A1 Jun. 22, 2023

Related U.S. Application Data

(63) Continuation of application No. PCT/CN2021/112352, filed on Aug. 12, 2021, and a continuation-in-part of application No. 17/410,965, filed on Aug. 24, 2021, now Pat. No. 11,629,148, which is a continuation of application No. PCT/CN2020/076231, filed on Feb. 21, 2020.

(30) Foreign Application Priority Data

Feb. 25, 2019 (CN) ......................... 201910137984.0
Sep. 17, 2019 (CN) ......................... 201910877661.5
Aug. 14, 2020 (CN) ......................... 202010818212.6

(51) Int. Cl.
*A61K 31/4188* (2006.01)
*C07D 487/04* (2006.01)

(52) U.S. Cl.
CPC ........ *C07D 487/04* (2013.01); *C07B 2200/13* (2013.01)

(58) Field of Classification Search
CPC .......................... A61K 31/4188; C07D 487/04
USPC ....................................... 514/393; 548/303.1
See application file for complete search history.

(56) References Cited

U.S. PATENT DOCUMENTS

| | | | |
|---|---|---|---|
| 6,313,129 B1 | 11/2001 | Uckun et al. | |
| 11,629,148 B2 | 4/2023 | Lu et al. | |
| 2017/0071946 A1 | 3/2017 | Coe et al. | |

FOREIGN PATENT DOCUMENTS

| | | |
|---|---|---|
| CL | 2014000122 A1 | 8/2014 |
| CN | 101401807 A | 4/2009 |
| CN | 103476770 A | 12/2013 |
| CN | 103717599 A | 4/2014 |
| CN | 108349972 A | 7/2018 |
| CN | 110461839 A | 11/2019 |
| CN | 110573508 A | 12/2019 |
| CN | 111606908 A | 9/2020 |
| CN | 114075200 A | 2/2022 |
| JP | 2014522865 A | 9/2014 |
| JP | 2017515836 A | 6/2017 |
| JP | 2018531982 A | 11/2018 |
| WO | 2013014567 A1 | 1/2013 |
| WO | 2017077283 A1 | 5/2017 |
| WO | 2017077288 A1 | 5/2017 |
| WO | 2017079205 A1 | 5/2017 |
| WO | 2018204238 A1 | 11/2018 |
| WO | 2020173400 A1 | 9/2020 |
| WO | 2022033562 A1 | 2/2022 |

OTHER PUBLICATIONS

China National Intellectual Property Adminstration; First Office Action issued in CN App. No. 202010818212.6; dated Aug. 13, 2024; 9 pages.

(Continued)

*Primary Examiner* — Douglas M Willis
(74) *Attorney, Agent, or Firm* — MASCHOFF BRENNAN

(57) ABSTRACT

The present disclosure relates to a JAK inhibitor compound and uses thereof. Specifically, the present disclosure discloses a compound of formula (G) in a solid form, isotopically labeled compound thereof, or optical isomer thereof, geometric isomer thereof, a tautomer thereof or a mixture of various isomers, or a pharmaceutically acceptable salt thereof, or a prodrug thereof, or a metabolite thereof. The present disclosure also relates to the application of the compound in a solid form in medicine.

(I)

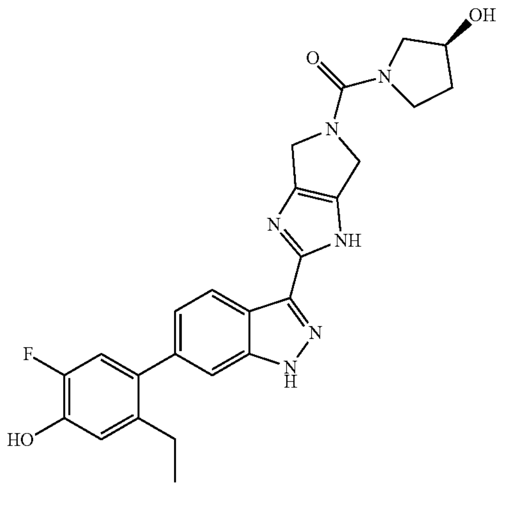

32 Claims, 27 Drawing Sheets

(56) References Cited

OTHER PUBLICATIONS

China National Intellectual Property Adminstration; First Office Action issued in CN App. No. 202010818470.4 dated Aug. 9, 2024; 9 pages.
Spinelli, Francesca Romana et al.; "HiJAKing SARS-CoV-2? The potential role of JAK inhibitors in the management of COVID-19"; Sci Immunol. May 8, 2020;5(47):eabc5367. doi: 10.1126/sciimmunol.abc5367. PMID: 32385052.
Bagca; Bakiey Goker et al.; "The potential of JAK/STAT pathway inhibition by ruxolitinib in the treatment of COVID-19"; Cytokine and Growth Factor Reviews 54; Jun. 20, 2020; pp. 51-61; DOI: https://doi.org/10.1016/j.cytogfr.2020.06.013.
Atallah, E. et al., Prospect of JAK2 inhibitor therapy in myeloproliferative neoplasms, Expert Reviews Anticancer Therapy, 9(5), 663-670, May 2009.
Barosi, G. et al., Novel strategies for patients with chronic myeloproliferative disorders, Current Opinion in Hematology, 16(2), 129-134, Mar. 2009.
Borie, D.C. et al., JAK3 inhibition as a new concept for immune suppression, Current Opinion in Investigational Drugs, 4(11), 1297-1303, Nov. 2003. (Abstract).
Dörwald, F. Zaragoza, Side Reactions in Organic Synthesis: A Guide to Successful Synthesis Design, Weinheim: Wiley-VCH Verlag GmbH & Co. KGaA, 2005, Preface.
Jones, P. et al., Design and Synthesis of a Pan-Janus Kinase Inhibitor Clinical Candidate (PF-06263276) Suitable for Inhaled and Topical Delivery for the Treatment of Inflammatory Diseases of the Lungs and Skin, Journal of Medicinal Chemistry, 60(2), 767-786, Jan. 2017.
Jordan, V. C., Tamoxifen: A Most Unlikely Pioneering Medicine, Nature Reviews: Drug Discovery, 2, 205-213, Mar. 2003.
Kisseleva, T. et al., Signaling through the JAK/STAT pathway, recent advances and future challenges, Gene, 285 (1-2), 1-24, Feb. 2002.
Santos, F. et al., Phase 2 study of CEP-701, an orally available JAK2 inhibitor, in patients with primary or post-polycythemia vera/essential thrombocythemia myelofibrosis, Blood, The Journal of the American Society of Hematology, 115(6), 1131-1136, Feb. 2010.
Stahl, P. H. et al., Handbook of Pharmaceutical Salts: Properties, Selection, and Use, Chemistry International, 24 (3), 20, 2002. (Abstract).
Yamaoka, K. et al., The Janus kinases (Jaks), Genome Biology, 5(12), 253-253.6, Nov. 2004.
The first Office Action issued by the Chilean Patent Office dated Oct. 24, 2022 for the Chilean Patent Application No. 202102244.
The first Office Action issued by the China National Intellectual Property Administration (CNIPA) dated Dec. 23, 2020 for the Chinese Patent Application No. 202010110961.3.
The second Office Action issued by the China National Intellectual Property Administration (CNIPA) dated Mar. 12, 2021 for the Chinese Patent Application No. 202010110961.3.
The Extended European Search Report for the European Patent Application No. 20763885.9, issued on Nov. 14, 2022.
The first Office Action issued by the European Patent Office dated Apr. 3, 2023 for the European Patent Application No. 20763885.9.
International Search Report and Written Opinion for PCT/CN2020/076231, mailed May 15, 2020.
International Search Report and Written Opinion for PCT/CN2021/112352, mailed Oct. 14, 2021.
International Search Report and Written Opinion for PCT/CN2021/112351, mailed Nov. 4, 2021.
The first Office Action issued by the Intellectual Property Office of Singapore dated Jan. 23, 2023 for the Singapore Patent Application No. 11202109300Q.
Luo, W. et al., Targeting JAK-STAT Signaling to Control Cytokine Release Syndrome in COVID-19, Trends in Pharmacological Sciences, 41(8), 531-543, Aug. 2020.
Hackam, D. G. et al., Translation of Research Evidence From Animals to Humans, JAMA, 296(14), 1731-1732, Oct. 2006.
Oetjen, L. K. et al., Sensory Neurons Co-opt Classical Immune Signaling Pathways to Mediate Chronic Itch, Cell, 171(1), 217-228, Sep. 2017.
Immunopharmaceutics, Inc.; Burger's Medicinal Chemistry and Drug Discovery; Fifth Edition; vol. 1: Principles and Practice; Dec. 19, 1994; pp. 975-977.
Jones et al.; "Design and Synthesis of Pan-Janus Kinase Inhibitor Clinical Candidate (PF-06263276) Suitable for Inhaled and Topical Delivery for the Treatment of Inflammatory Disease of the Lungs and Skin"; Journal of Medicinal Chemistry; Dec. 16, 2016; 20 pages.
Japanese Patent Office; Notice of Refusal; issued in JP-2023507516 dated Jan. 30, 2024; 6 pages.
Japanese Patent Office; Notice of Refusal; issued in JP-2023507517 dated Feb. 19, 2024; 6 pages.
United States Patent and Trademark Office; Non-Final Office Action issued in U.S. Appl. No. 18/169,580; 50 pages.
State Intellectual Property Office of People's Republic of China; Second Office Action issued in CN App No. 2020108182126 dated May 20, 2025; 14 pages.
Zeng, Jingze; "Biopharmeceutical Analysis, Theory and technology applied to in vivo research of new drugs and monitoring of therapeutic drugs"; Second Edition; Feb. 1998; ISBN 7-81034-778-0.
Liang, Fang; "Pharmaceutrics"; Third Edition; Mar. 3, 2016; ISBN 978-7-5067-7405-5.
Rowe, Derek 8.; "The Chemistry Book, From Gunpowder to Graphene, 250 Milestones in the History of Chemistry"; Mar. 1, 2019; ISBN: 978-7-5689-1057-6.
Taiwan Patent Office; Concise Explanation of Relevance for TW OA 1; issued in TW App No. 110130006 dated Apr. 18, 2025; 7 pages.
The Technical Examination Report issued by the Brazilian Patent and Trademark Office dated May 18, 2023 for the Brazilian Patent Application No. BR 11 2021 016751-0 [Translation of the Office Action included].
The Communication pursuant to Article 94(3) EPC issued by the European Patent Office dated Sep. 14, 2023 for the European Patent Application No. 20 763 885.9-1110.
The Supplementary European Search Report issued by the European Patent Office dated Dec. 1, 2023 for the European Patent Application No. 21855613.2.
The First Examination Report issued by the Mexican Patent Office dated Aug. 1, 2023 for the Mexican Patent Application No. MX/a/2021/010242 [Translation of the Office Action included].
The Second Examination Report issued by the Mexican Patent Office dated Nov. 3, 2023 for the Mexican Patent Application No. MX/a/2021/010242 [Translation of the Office Action included].
The First Examination Report issued by the New Zealand Intellectual Property Office dated Dec. 12, 2023 for the New Zealand Patent Application No. 779955.
The First Examination Report issued by the Russian Patent Office dated Jul. 7, 2023 for the Russian Patent Application No. 2021127827 [Translation of the Office Action included].
The Second Examination Report issued by the Russian Patent Office dated Nov. 30, 2023 for the Russian Patent Application No. 2021127827 [Translation of the Office Action included].
The Examination Report issued by the Vietnamese Patent Office dated Oct. 10, 2023 for the Vietnamese Patent Application No. 1-2021-05946 [Translation of the Office Action included].
Eberl et al. "Chemical Proteomics Reveals Target Selectivity of Clinical Jak Inhibitors in Human Primary Cells," Scientific Reports, 9(1), 14159, Oct. 2019.
Tomaselli et al. "Epigenetic Polypharmacology: A New Frontier for Epi-Drug Discovery," Medicinal Research Reviews, 40(1), 190-244, Jan. 2020.
Zhang et al. "Recent Advances in Indazole-Containing Derivatives: Synthesis and Biological Perspectives," Molecules, 23(11), 2783, Oct. 2018.
Turner et al. "Identification of an Indazole-Based Pharmacophore for the Inhibition of FGFR Kinases Using Fragment-Led De Novo Design," ACS medicinal chemistry letters, 8(12), 1264-1268, Dec. 2017.

(56) References Cited

OTHER PUBLICATIONS

Lupardus PJ, Ultsch M, Wallweber H, Bir Kohli P, Johnson AR, Eigenbrot C. Structure of the pseudokinase-kinase domains from protein kinase TYK2 reveals a mechanism for Janus kinase (JAK) autoinhibition. Proc Natl Acad Sci U S A. Jun. 3, 2014;111(22):8025-30. doi: 10.1073/pnas.1401180111. Epub May 19, 2014. PMID: 24843152; PMCID: PMC4050602.

Solimani F, Meier K, Ghoreschi K. Emerging Topical and Systemic JAK Inhibitors in Dermatology. Front Immunol. Dec. 3, 2019;10:2847. doi: 10.3389/fimmu.2019.02847. PMID: 31849996; PMCID: PMC6901833.

Wrobleski ST, Moslin R, Lin S, Zhang Y, Spergel S, Kempson J, Tokarski JS, Strnad J, Zupa-Fernandez A, Cheng L, Shuster D, Gillooly K, Yang X, Heimrich E, McIntyre KW, Chaudhry C, Khan J, Ruzanov M, Tredup J, Mulligan D, Xie D, Sun H, Huang C, D'Arienzo C, Aranibar N, Chiney M, Chimalakonda A, Pitts WJ, Lombardo L, Carter PH, Burke JR, Weinstein DS. Highly Selective Inhibition of Tyrosine Kinase 2 (TYK2) for the Treatment of Autoimmune Diseases: Discovery of the Allosteric Inhibitor BMS-986165. J Med Chem. Oct. 24, 2019;62(20):8973-8995. doi: 10.1021/acs.

Jones P, Storer RI, Sabnis YA, Wakenhut FM, Whitlock GA, England KS, Mukaiyama T, Dehnhardt CM, Coe JW, Kortum SW, Chrencik JE, Brown DG, Jones RM, Murphy JR, Yeoh T, Morgan P, Kilty I. Design and Synthesis of a Pan-Janus Kinase Inhibitor Clinical Candidate (PF-06263276) Suitable for Inhaled and Topical Delivery for the Treatment of Inflammatory Diseases of the Lungs and Skin. J Med Chem. Jan. 26, 2017;60(2):767-786. doi: 10.1021/acs.jmedchem.6b01634. Epub Jan. 4, 2017. PMID: 27983835.

Jones P, Storer RI, Sabnis YA, Wakenhut FM, Whitlock GA, England KS, Mukaiyama T, Dehnhardt CM, Coe JW, Kortum SW, Chrencik JE, Brown DG, Jones RM, Murphy JR, Yeoh T, Morgan P, Kilty I. Supporting Information: Design and Synthesis of a Pan-Janus Kinase Inhibitor Clinical Candidate (PF-06263276) Suitable for Inhaled and Topical Delivery for the Treatment of Inflammatory Diseases of the Lungs and Skin. J Med Chem. Jan. 26, 2017;60(2):767-786. doi: 10.1021/acs.jmedchem.6b01634. Epub Jan. 4, 2017. PMID: 27983835.

SOLID FORMS OF PHARMACEUTICALLY ACCEPTABLE SALTS OF (S)-(2-ETHYL-5-FLUORO-4-HYDROXYPHENYL)-1H-INDAZOL-3-YL)-4,6-DIHYDROPYRROLO-[3,4-D]IMIDAZOL-5(1H)-YL)(3-HYDROXYPYRROLIDIN-1-YL)METHANONE AS JAK INHIBITORS

CROSS REFERENCE TO RELATED APPLICATION

This application is a continuation of International Patent Application No. PCT/CN2021/112352, filed on Aug. 12, 2021, which claims priority to Chinese Patent Application No. 202010818212.6, filed on Aug. 14, 2020; this application is also a continuation-in-part of U.S. patent application Ser. No. 17/410,965, filed on Aug. 24, 2021, which is a continuation of International Patent Application No. PCT/CN2020/076231, filed on Feb. 21, 2020, which claims priority to Chinese Patent Application No. 201910877661.5, filed on Sep. 17, 2019 and Chinese Patent Application No. 201910137984.0, filed on Feb. 25, 2019, all of which are incorporated herein by reference in their entireties.

TECHNICAL FIELD

The present disclosure provides a novel compound with pharmacological activity, which can be used to inhibit Janus kinase (JAK). The present disclosure also relates to a composition comprising the compound, and use of the compound and the composition in a field of medicine.

BACKGROUND

Protein kinases are a family of enzymes that catalyze phosphorylation of specific residues in proteins, and are broadly classified into tyrosine and serine/threonine kinases. Inappropriate kinase activities caused by mutations, over-expression or inappropriate regulation, abnormal regulation or dysregulation, and excessive or insufficient production of growth factors or cytokines are involved in many diseases, including but not limited to cancers, cardiovascular diseases, allergies, asthma and other respiratory diseases, autoimmune diseases, inflammatory diseases, bone diseases, metabolic disorders and neurological and neurodegenerative disorders (such as Alzheimer's disease). Inappropriate kinase activity triggers a variety of biological cell responses associated with cell growth, cell differentiation, cell function, survival, apoptosis, and cell motility related to the aforementioned diseases and other related diseases. Therefore, protein kinases have become an important class of enzymes as targets for therapeutic intervention. In particular, the JAK family of cellular protein tyrosine kinases plays an important role in cytokine signal transduction (Kisseleva et al., Gene, 2002, 285, 1; Yamaoka et al., Genome Biology 2004, 5, 253).

Since the first JAK inhibitor was discovered in the early 1990s, the development of JAK inhibitors has gone through nearly 30 years. JAK is a family of intracellular non-receptor tyrosine kinases, which plays an important role in cytokine receptor signaling pathway by interacting with signal transducer and activator of transcription (STAT). JAK/STAT signaling pathway is involved in many important biological processes such as cell proliferation, differentiation, apoptosis and immune regulation. Compared with other signal pathways, the transmission process of this signal pathway is relatively simple. It is mainly composed of three components, namely tyrosine kinase associated receptor, tyrosine kinase JAK, signal transducer and activator of transcription STAT.

Many cytokines and growth factors transmit signals through the JAK-STAT signal pathway, including interleukins (such as IL-2 to IL-7, IL-9, IL-10, IL-15, IL-21, and the like), GM-CSF (granulocyte/macrophage colony stimulating factor), GH (growth hormone), EGF (epidermal growth factor), PRL (prolactin), EPO (erythropoietin), TPO (thrombopoietin), PDGF (platelet derived factors) and interferons (including IFN-α, IFN-β, IFN-γ and the like) and so on. These cytokines and growth factors have corresponding receptors on the cell membrane. The common feature of these receptors is that the receptor itself does not have kinase activity, but its intracellular segment has a binding site for tyrosine kinase JAK. After the receptor binds to a ligand, tyrosine residues of various target proteins are phosphorylated by activation of JAK that binds to the receptor to realize signal transfer from the extracellular to the intracellular.

JAK is a cytoplasmic tyrosine kinase that transduces cytokine signals from membrane receptors to STAT transcription factors. As mentioned above, JAK is the abbreviation of Janus kinase in English. In Roman mythology, Janus is the double-faced god in charge of the beginning and the end. The reason why it is called Janus kinase is that JAK can phosphorylate cytokine receptors that it binds to, and also phosphorylate multiple signal molecules containing specific SH2 domains. The JAK protein family includes 4 members: JAK1, JAK2, JAK3, and TYK2. They have 7 JAK homology domains (JH) in structure in which the JH1 domain is a kinase domain having the function of encoding kinase proteins; JH2 domain is a "pseudo" kinase domain, which regulates the activity of JH1; and JH3-JH7 constitute a four-in-one domain, which regulates the binding of JAK proteins to receptors.

STAT is a type of cytoplasmic protein that can bind to DNA in the regulatory region of target genes, and is a downstream substrate of JAK. Seven members of the STAT family have been discovered, namely STAT1, STAT2, STAT3, STAT4, STAT5A, STAT5B and STAT6. STAT protein can be divided into the following functional segments in structure including N-terminal conserved sequence, DNA binding region, SH3 domain, SH2 domain and C-terminal transcription activation region. Among them, the segment of the most conserved in sequence and most important in function is the SH2 domain, which has the same core sequence "GTFLLRESS" as the SH2 domain of tyrosine kinase Src.

JAK-STAT signaling pathway has a wide range of functions and is involved in many important biological processes such as cell proliferation, differentiation, apoptosis, and immune regulation. At present, the research related to disease and drug innovation mainly focuses on inflammatory diseases and neoplastic diseases in which the inflammatory diseases mainly include rheumatoid arthritis, canine dermatitis, psoriasis, ulcerative colitis and Crohn's disease; and the neoplastic diseases mainly involve myelofibrosis, polycythemia vera and primary platelets hyperplasia. In addition, mutations in JAK molecule itself can also cause acute myeloid leukemia (AML), acute lymphocytic leukemia (ALL), ductal breast carcinoma and non-small cell lung cancer (NSCLC), polycythemia vera (PV), essential thrombocythemia (ET), idiopathic myelofibrosis (IMF), chronic myeloid leukemia (CML), and the like. In addition, the JAK-STAT signaling pathway has been reported to be closely associated with cytokine storm in Covid-19.

JAK is a very important drug target. JAK inhibitors developed for this target are mainly used to screen therapeutic drugs for blood system diseases, tumors, rheumatoid arthritis and psoriasis. JAK-1, JAK-2 and TYK-2 are expressed in various tissue cells of human body. JAK-3 is mainly expressed in various hematopoietic tissue cells, mainly in bone marrow cells, thymocytes, NK cells and activated B lymphocytes and T lymphocytes. Studies have shown that JAK2 inhibitors are suitable for myeloproliferative diseases (Santos et al., Blood, 2010, 115:1131; Barosi G. and Rosti V., Curr. Opin. Hematol., 2009, 16:129; Atallah E. and Versotvsek S., 2009 Exp. Rev. Anticancer Ther. 9:663), and JAK3 inhibitors are suitable as immunosuppressive agents (such as, U.S. Pat. No. 6,313,129; Borie et al., Curr. Opin. Investigational Drugs, 2003, 4:1297). In addition, JAK inhibitors are considered promising for the treatment of severe pneumonia, such as pneumonia caused by Covid-19, to suppress inflammatory response, and reduce the risk of cytokine storm, thereby reducing mortality (Wei Luo et al. Trends in Pharmacological Science, 41 (8)—June 2020, "Targeting JAK-STAT Signaling to Control Cytokine Release Syndrome in COVID-19"). There is also literature reporting the efficacy of JAK inhibitors for the treatment of pruritus (Landon K. Oetjen et al, Cell, 171, P217-228, Sep. 21, 2017, "Sensory Neurons Co-opt Classical Immune Signaling Pathways to Mediate Chronic Itch").

Currently, JAK inhibitors approved by the FDA and EMA include Tofacitinib, Ruxolitinib, and Oclacitinib. JAK inhibitors in the middle and late stages of clinical research include Filgotinib, Peficitinib and so on.

Tofacitinib, a JAK3 inhibitor, was developed by Pfizer and was approved by the FDA in November 2012 for the treatment of moderate to severe rheumatoid arthritis (RA) due to inadequate response or intolerance to methotrexate in adult patients. It is the first oral JAK inhibitor approved for RA treatment. After that, it was approved by Japan PMDA for listing in March 2013 under the trade name Xeljanz. On Mar. 16, 2017, Pfizer China announced that the CFDA had formally approved Pfizer's application for the marketing of the oral JAK inhibitor. It was reported that the drug was approved for the treatment of adult patients with moderate to severe rheumatoid arthritis having inadequate response or intolerance to methotrexate. At present, Tofacitinib is close to being approved for indications such as psoriasis, ulcerative colitis, juvenile idiopathic arthritis; and clinical trials for the treatment of indications such as Crohn's disease and alopecia areata have also entered the mid- to late-stage. The main side effects of Tofacitinib are serious infection rate and increased low-density lipoprotein level. The most common adverse effects are upper respiratory tract infection, headache, diarrhea, nasal congestion, sore throat and nasopharyngitis. In addition, it has been have reported that Tofacitinib can cause side effects such as anemia and neutropenia in clinical studies.

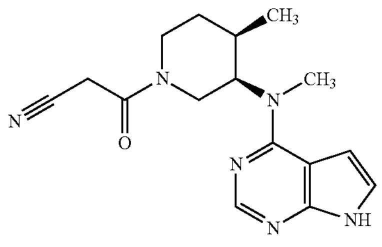

Tofacitinib

Filgotinib, a JAK1 inhibitor, passed Phase III clinical trials in September 2018 for the treatment of rheumatoid arthritis. At the same time, the study of Filgotinib for the treatment of ulcerative colitis and Crohn's disease is currently in clinical phase II/III trials. Filgotinib is a selective JAK1 inhibitor with IC50 of about 10 nM, 28 nM, 810 nM and 116 nM for JAK1, JAK2, JAK3 and TYK2, respectively, as reported.

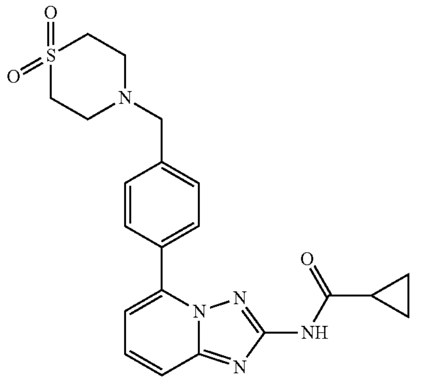

Filgotinib

Although some JAK inhibitors have been approved for listing, and some of JAK inhibitors are still in clinical research, these JAK inhibitors are not satisfactory in terms of efficacy or safety. Therefore, there is always a need for JAK inhibitors with better efficacy and/or fewer side effects.

SUMMARY

It is one object of the present disclosure to provide a novel JAK inhibitor alternative to existing JAK inhibitors, so as to provide more options for the treatment of JAK-related diseases.

A further object of the present disclosure is to provide a novel JAK inhibitor with better efficacy and/or better safety than existing JAK inhibitors.

An even further object of the present disclosure is to provide solid forms of a novel JAK inhibitor that are more suitable for pharmaceutical formulation.

In a first aspect, the present disclosure provides a solid form of a compound, wherein the compound is the compound of formula (I)

(I)

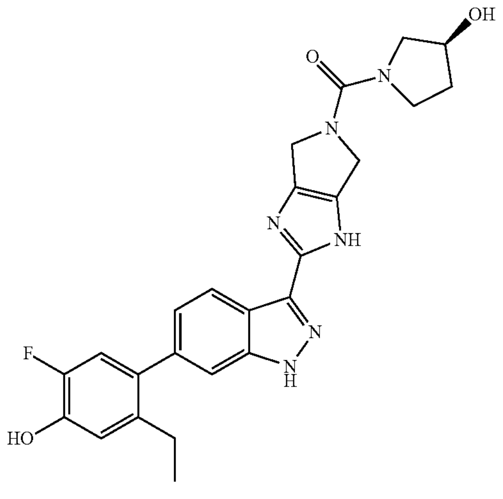

or an isotopically labeled compound of compound of formula (I), or an optical isomer of compound of formula (I), or a geometric isomer of compound of formula (I), or a tautomer of compound of formula (I), or a mixture of isomers of compound of formula (I), a pharmaceutically acceptable salt of compound of formula (I), or a solvate of any one of these compounds. Preferably, the solid form of the compound is a crystal form.

In a second aspect, the present disclosure provides a pharmaceutical composition comprising the compound in solid form as described in a first aspect of the present disclosure and one or more pharmaceutically acceptable carriers, adjuvants or excipients. For example, said pharmaceutical composition may be in the form of a dispersion or in the form of a solution.

In a third aspect, the present disclosure provides use of the compound in solid form as described in the first aspect of the present disclosure or the pharmaceutical composition as described in the second aspect of the present disclosure in the preparation of a drug for the treatment and/or prevention of a disease or condition associated with JAK.

In a fourth aspect, the present disclosure provides a method of treating a disease or condition associated with JAK, said method comprising administering to a patient in need thereof a therapeutically effective amount of the compound in solid form as described in the first aspect of the present disclosure or a pharmaceutical composition as described in the second aspect of the present disclosure. Said patient is preferably a mammal, more preferably human. The route of administration may be oral administration, topical administration, parenteral administration, bronchial administration or nasal administration, preferably oral administration.

The present application provides a novel compound that inhibits JAK, thereby providing additional options for the prevention or treatment of JAK-related diseases. In addition, the present application provides a plurality of solid forms of the compound, including a plurality of crystal forms and amorphous forms, which have different chemical and physical properties as well as different metabolic properties in vivo, thus providing more freedom in the production, storage and selection of different drug dosage forms. Thus, novel drug dosage forms with higher bioavailability and/or better efficacy may be provided.

DETAILED DESCRIPTION

The following is a specific description of how the technical solutions of the present application are implemented. In these specific descriptions, a number of technical terms are used. In this disclosure, unless otherwise indicated, all terms have the meaning commonly understood by those skilled in the art.

In a first aspect, the present disclosure relates to a solid form of a compound, wherein the compound is the compound of formula (I)

(I)

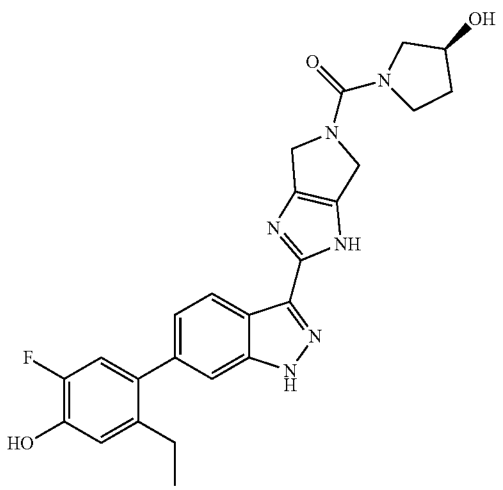

or an isotopically labeled compound of compound of formula (I), or an optical isomer of compound of formula (I), or a geometric isomer of compound of formula (I), or a tautomer of compound of formula (I), or a mixture of isomers of compound of formula (I), a pharmaceutically acceptable salt of compound of formula (I), or a solvate of any one of these compounds.

The compound of formula (I) can be named as(S)-(2-(6-(2-ethyl-5-fluoro-4-hydroxyphenyl)-1H-indazol-3-yl)-4,6-dihydropyrrolo[3,4-d]imidazol-5-(1H)-yl) (3-hydroxy pyrrolidin-1-yl) ketone.

For simplicity, hereinafter, the term "compound according to the present application" or "compound of the present application" encompasses the compound of Formula (I), or an isotopically labeled compound of compound of formula (I), or an optical isomer of compound of formula (I), or a geometric isomer of compound of formula (I), or a tautomer of compound of formula (I), or a mixture of isomers of compound of formula (I), or a solvate of any one of these compounds.

The term "optical isomer" refers that when a compound has one or more chiral centers, each chiral center may have an R configuration or an S configuration, and the various isomers thus constituted are known as an optical isomer. Optical isomers comprise all diastereomers, enantiomers, meso forms, racemates or mixtures thereof. For example, optical isomers can be separated by a chiral chromatography or by chiral synthesis.

The term "geometric isomer" refers that when a double bond is present in a compound, the compound may exist as a cis isomer, a trans isomer, an E isomer, or a Z isomer. A geometric isomer comprises a cis isomer, trans isomer, E isomer, Z isomer, or a mixture thereof.

The term "tautomer" refers to an isomer that is formed by rapid movement of an atom at two positions in a single molecule. It will be understood by those skilled in the art that tautomers can be mutually transformed, and in a certain state, may coexist by reaching an equilibrium state. As used herein, the term "compound of formula (I)" also encompasses any tautomer of the compound of formula (I).

Unless otherwise indicated, reference to "compound as shown by formula (I)" or "compound of formula (I)" or "compound of the present application" herein also encompasses isotopically-labeled compounds obtained by replacing any atom of the compound with its isotopic atom.

The term "isotopically-labeled compounds" refers to such a compound in which one or more atoms are displaced by atoms having the same atomic number but different atomic mass or mass number than those normally found in nature.

Examples of isotopes suitable for inclusion in the compound of the present application include isotopes of hydrogen, such as $^{2}H$ (D) and $^{3}H$ (T), of carbon, such as $^{11}C$, $^{13}C$ and $^{14}C$, of chlorine, such as $^{36}Cl$, of fluorine, such as $^{18}F$, of iodine, such as $^{123}I$ and $^{125}I$, of nitrogen, such as $^{13}N$ and $^{15}N$, of oxygen, such as $^{15}O$, $^{17}O$ and $^{18}O$, and of sulphur, such as $^{35}S$.

Certain isotopically-labelled compounds of formula (I), for example, those incorporating a radioactive isotope, are useful in drug and/or substrate tissue distribution studies. The radioactive isotopes deuterium, i.e. $^{2}H$, and carbon-14, i.e. $^{14}C$, are particularly useful for this purpose in view of their ease of incorporation and ready means of detection.

Substitution with heavier isotopes such as deuterium, i.e. $^{2}H$, may afford certain therapeutic advantages resulting from greater metabolic stability, for example, increased in vivo half-life or reduced dosage requirements, and hence may be preferred in some circumstances.

Substitution with positron emitting isotopes, such as $^{11}C$, $^{18}F$, $^{15}O$ and $^{13}N$, can be useful in Positron Emission Topography (PET) studies for examining substrate receptor occupancy.

Isotopically-labeled compounds of formula (I) can generally be prepared by conventional techniques known to those skilled in the art or by processes analogous to those described in the accompanying Examples using an appropriate isotopically-labeled reagents in place of the non-labeled reagent previously employed.

The compound of the present application may be in the form of a pharmaceutically acceptable salt of the compound of formula (I), particularly, an acid addition salt of the compound of formula (I). Suitable acid addition salts are formed from acids that form non-toxic salts. Examples include but are not limited to: muconate, hippurate, ascorbate, succinate, naphthalene-2-sulfonate, acetate, adipate, aspartate, benzoate, benzenesulfonate, bicarbonate/carbonate, bisulfate/sulfate, borate, camphor sulfonate, citrate, cyclohexamine sulfonate, ethanedisulfonate, formate, fumarate, glucoheptonate, gluconate, glucuronate, hexafluorophosphate, 2-(4-hydroxybenzyl)benzoate, hydrochloride/chloride, hydrobromide/bromide, hydroiodide/iodide, 2-isethionate, lactate, malate, maleate, malonate, methanesulfonate, methyl sulfate, naphthalate, 2-naphthalenesulfonate, nicotinate, nitrate, orotate, oxalate, palmitate, phosphate/hydrogen phosphate/dihydrogen phosphate, pyroglutamate, glucarate, stearate, salicylate, tannate, tartrate, tosylate and trifluoroacetate. For a review of suitable salts, please refer to Handbook of Pharmaceutical Salts: Properties, Selection and Use by Stahl and Wermuth (Wiley-VCH, 2002). Methods for preparing pharmaceutically acceptable salts of the compounds described herein are known to those skilled in the art.

Particularly preferred pharmaceutically acceptable salts of the compound of formula (I) are its hydrochloride, phosphate, maleate, L-tartrate, fumarate, mucinate, citrate, p-toluenesulfonate, methanesulfonate, or benzenesulfonate. The most preferred pharmaceutically acceptable salt of the compound of formula (I) is its phosphate, maleate, or methanesulfonate.

The term "pharmaceutically acceptable" means that the corresponding compound, carrier or molecule is suitable for administration to mammals, preferably humans. Preferably, the term refers to it is approved by regulatory agencies such as CFDA (China), EMEA (Europe), FDA (United States), and other national regulatory agencies to be suitable for mammals, preferably humans.

As used herein, the term "pharmaceutically acceptable salt of compound of formula (I)" is used to denote a pharmaceutically acceptable salt of compound of formula (I) in any form, encompassing a pharmaceutically acceptable salt of any one of compound of formula (I), an isotopically labeled compound of compound of formula (I), an optical isomer of compound of formula (I), a geometric isomer of compound of formula (I), a tautomer of compound of formula (I) and a mixture of isomers of compound of formula (I).

Certain compounds of the present application may be present in a nonsolvated form as well as a solvated form, including a hydrated form. In the present disclosure, the terms "compound of formula (I)", "isotopically labeled compound of formula (I)", "optical isomer of compound of formula (I)", "geometric isomer of compound of formula (I)", "tautomer of compound of formula (I)", "a mixture of isomers of compound of formula (I)" and "pharmaceutically acceptable salt of compound of formula (I)" all cover their solvates.

In the present application, the terms "solid form of a compound" and "compound in solid form" are understood to have the same meaning and are therefore used interchangeably, indicating that the compound is predominantly in solid form. It is understood by those of ordinary skill in the art that a compound in solid form can exist as a crystal (crystal form), an amorphous substance (non-crystal), or a mixture of both.

The term "crystal" or "crystal form" refers to a solid form as a crystal, which can be determined, for example, by X-ray diffraction. In some embodiments, a crystal form of substance may be substantially free of non-crystalline and/or other crystal forms. In certain embodiments, the crystal form of substance may contain one or more non-crystalline and/or other crystal forms of less than about 1%, less than about 2%, less than about 3%, less than about 4%, less than about 5%, less than about 6%, less than about 7%, less than about 8%, less than about 9%, or less than about 10% by weight. In some embodiments, a crystal form of substance may have a purity of about 99%, about 98%, about 97%, about 96%, about 95%, about 94%, about 93%, about 92%, about 91%, or about 90%.

The term "non-crystal" or "non-crystal form" or "amorphous form" means a solid form that is essentially not a crystal, and which can be determined, for example, by X-ray diffraction. Specifically, the term "non-crystal" or "non-crystal form" or "amorphous form" describes a disordered solid form, i.e., a solid form that lacks long-range ordering. In some embodiments, a non-crystal form of substance may be substantially free of other non-crystal forms and/or crystal forms. In certain embodiments, a non-crystal form of substance may contain one or more other amorphous forms and/or crystal forms of less than about 1%, less than about 2%, less than about 3%, less than about 4%, less than about 5%, less than about 6%, less than about 7%, less than about 8%, less than about 9%, less than about 10% by weight. In some embodiments, a non-crystal form of substance may have a purity of about 99%, about 98%, about 97%, about 96%, about 95%, about 94%, about 93%, about 92%, about 91%, or about 90%.

A polymorphism phenomenon exists in the compound of the present application. The term "polymorphism phenomenon" refers to a situation in which different crystals having the same molecular structure are formed due to different arrangements or conformations in the crystal lattice. It is known in the art that crystals of a compound with the same molecular structure but having different crystal forms may have different chemical and physical properties such as bioavailability, solubility, dissolution rate, chemical and physical stability, melting point, color, filterability, hygroscopicity, density, and the like.

In a preferred embodiment of the present application, said solid form is a crystal of compound of formula (I) or a crystal of a salt of compound of formula (I) as prepared in the Examples of the present application. For example, in some preferred embodiments of the present application, said solid form is a phosphate crystal form A of compound of formula (I), a maleate crystal form A of compound of formula (I), a methanesulfonate crystal form B of compound of formula (I), a crystal form A of a hydrate of compound of formula (I), a crystal form B of compound of formula (I), and the like.

In a preferred embodiment of the present application, said solid form is a crystal of compound of formula (I) or a crystal of a salt of compound of formula (I) prepared in the "Examples" section of the present disclosure, and said crystal (or crystal form) has a powder X-ray diffraction pattern preferably with one or more characteristic peaks at the same position of the diffraction angle (20) as in the corresponding XRPD spectrum measured in the "Examples" section of the present disclosure. By "one or more characteristic peaks" it is meant at least 1, at least 2, at least 3, at least 4, at least 5, at least 6, at least 7, at least 8, at least 9, at least 10, at least 11, at least 12, at least 13, at least 14, at least 15, at least 16, at least 17, at least 19 at least 18, at least 19, or at least 20 characteristic peaks. Herein, "characteristic peak" is understood to mean one or more peaks with the greatest relative intensity in an XRPD spectrum. It would be understood by those skilled in the art that the positions of XRPD peaks measured under different conditions may deviate to some extent due to differences in sample purity and test conditions. The expression "same position" is therefore understood herein to mean that there can be a difference of ±0.50°, ±0.40°, ±0.30°, ±0.20°, preferably ±0.10° with respect to the corresponding diffraction angle (20) position given in the "Examples" section of the present disclosure. Most preferably, the powder X-ray diffraction pattern of said crystals (or crystal forms) is substantially the same as the corresponding XRPD pattern measured in the "Examples" section of the present disclosure. By "substantially the same as the corresponding XRPD pattern" it is meant that the two XRPD patterns are identical, or that there are some differences, but those skilled in the art can identify that the differences are immaterial and caused by different sample purities, measurement conditions, instrumentation errors or operating habits, and thus they may confirm that the two XRPD patterns are obtained from the same crystal.

In a preferred embodiment of the present application, said solid form is a crystal of compound of formula (I) or a crystal of a salt of compound of formula (I) prepared in the "Examples" section of the present disclosure, and said crystal (or crystal form) has a TGA or DSC profile preferably with at least one, at least two, at least three, or at least four characteristic peaks at the same position as the corresponding TGA or DSC profile measured in the "Examples" section of the present disclosure. The "characteristic peaks" are understood herein to be heat absorption or exothermic peaks in the TGA/DSC curves. It would be understood by those skilled in the art that the temperature readings indicating the peak positions in the TGA/DSC curves measured under different conditions may deviate to some extent due to differences in sample purity and test conditions. The expression "same position" is therefore understood herein to mean that relative to the corresponding TGA and/or DSC curves given in the "Examples" section of the present disclosure, the temperature at the same position can vary by ±5° C., ±4° C., ±3° C., ±2° C., ±1° C. Most preferably, the TGA/DSC curves of said crystal (or crystal form) are substantially the same as the corresponding TGA/DSC curves measured in the "Examples" section of the present disclosure. By "substantially the same as the corresponding TGA/DSC curves" it is meant that the two TGA and/or DSC curves are identical, or that there are some differences, but those skilled in the art can identify that the differences are immaterial and caused by different sample purities, measurement conditions, instrumentation errors or operating habits, and thus they may confirm that the two TGA and/or DSC curves are obtained from the same crystal.

A preferred embodiment of the present application relates to a crystal form A of a hydrate of compound of formula (I) with a powder X-ray diffraction pattern (XRPD) having one or more characteristic peaks at a diffraction angle (2θ) selected from 8.67±0.10°, 13.39±0.10°, 15.05±0.10°, 17.38±0.10°, 21.24±0.10°, 22.86±0.10°, 24.89±0.10°+0.10°, preferably with one or more characteristic peaks at a diffraction angle (2θ) selected from 8.67±0.10°, 11.53±0.10°, 13.39±0.10°, 15.05±0.10°, 17.38±0.10°, 21.24±0.10°, 21.63±0.10°, 22.19±0.10°, 22.86±0.10°±0.10°, 23.43±0.10°, 24.89±0.10°.

Further preferably, the crystal form A of a hydrate of compound of formula (I) has multiple thermal signals in the range of about 50-290° C. in its TGA/DSC curve.

A preferred embodiment of the present application relates to a crystal form B of compound of formula (I) with a powder X-ray diffraction pattern (XRPD) having one or more characteristic peaks at a diffraction angle (2θ) selected from 7.70±0.10°, 11.20±0.10°, 12.46±0.10°, 15.44±0.10°, 18.17±0.10°, 18.48±0.10°, 19.27±0.10°, 21.84±0.10°, 22.94±0.10°, 24.29±0.10°, 25.40±0.10°, 27.92±0.10°, preferably with one or more characteristic peaks at a diffraction angle (2θ) selected from 7.70±0.10°, 11.20±0.10°, 12.46±0.10°, 15.44±0.10°, 18.17±0.10°, 18.48±0.10°, 18.93±0.10°, 19.27±0.10°, 19.50±0.10°, 20.83±0.10°, 21.84±0.10°, 22.94±0.10°, 23.22=0.10°, 24.29±0.10°, 25.40±0.10°, 26.74±0.10°, 27.92±0.10°.

Further preferably, the crystal form B of compound of formula (I) has a heat absorption peak at about 319.1° C. (onset temperature) in its TGA/DSC curve.

A preferred embodiment of the present application relates to a crystal form C of a hydrate of compound of formula (I) with a powder X-ray diffraction pattern (XRPD) having one or more characteristic peaks at a diffraction angle (2θ) selected from 4.96±0.10°, 7.66±0.10°, 10.18±0.10°, 11.07±0.10°, 14.73±0.10°, 22.87±0.10°, preferably with one or more characteristic peaks at a diffraction angle (2θ) selected from 4.96±0.10°, 7.66±0.10°, 10.18±0.10°, 11.07±0.10°, 12.43±0.10°, 14.73±0.10°, 16.10±0.10°, 19.24±0.10°, 22.87±0.10°, 23.52±0.10° 0.10°, 24.27±0.10°, 25.09±0.10°.

Further preferably, the crystal form C of a hydrate of compound of formula (I) has a thermal signal at about 78.1° C. (onset temperature) and thermal signals at about 279.4 (onset temperature) and 303.8° C. (onset temperature) in its TGA/DSC curve.

A preferred embodiment of the present application relates to a crystal form G of a hydrate of compound of formula (I) with a powder X-ray diffraction pattern (XRPD) having one or more characteristic peaks at a diffraction angle (2θ)

selected from 6.42±0.10°, 7.04±0.10°, 7.69±0.10°, 12.52±0.10°, 15.81±0.10°, 18.83±0.10°, 22.85±0.10°, 23.40±0.10°, preferably with one or more characteristic peaks at a diffraction angle (2θ) selected from 6.42±0.10°, 7.04±0.10°, 7.69±0.10°, 11.48±0.10°, 12.52±0.10°, 15.81±0.10°, 18.83±0.10°, 19.58±0.10°, 22.85±0.10°, 23.40±0.10°, 25.31±0.10°, 27.85±0.10°.

Further preferably, the crystal form G of a hydrate of compound of formula (I) has a thermal signal at about 81.2° C. (onset temperature) and two thermal signals at about 209.6° C. (onset temperature), and about 314.0° C. (onset temperature) in its TGA/DSC curve.

A preferred embodiment of the present application relates to a phosphate crystal form A of compound of formula (I) having a powder X-ray diffraction pattern (XRPD) having one or more characteristic peaks at a diffraction angle (2θ) selected from 5.29±0.10°, 7.47±0.10°, 10.61±0.10°, 19.16±0.10° and 21.32±0.10°, preferably with one or more characteristic peaks at a diffraction angle (2θ) selected from 5.29±0.10°, 7.47±0.10°, 10.61±0.10°, 15.94±0.10°, 16.77±0.10°, 18.68±0.10°, 19.16±0.10°, 21.32±0.10° and 25.36±0.10°.

Further preferably, the phosphate crystal form A of compound of formula (I) has a shape heat absorption peak at about 279.3° C. (onset temperature) in its TGA/DSC curve.

A preferred embodiment of the present application relates to a maleate crystal form A of compound of formula (I) having a powder X-ray diffraction pattern (XRPD) having one or more characteristic peaks at a diffraction angle (2θ) selected from 4.55±0.10°, 8.78±0.10°, 12.69±0.10°, 13.96±0.10°, 16.62±0.10°, 17.61±0.10°, 18.32±0.10° 0.10°, 25.39±0.10°, and 26.53±0.10°, preferably with one or more characteristic peaks at a diffraction angle (2θ) selected from 4.55±0.10°, 8.78±0.10°, 12.69±0.10°, 13.74±0.10°, 13.96±0.10°, 16.62±0.10°, 17.61±0.10°, 18.32±0.10°, 21.72±0.10°, 25.39±0.10°, and 26.53±0.10°.

Further preferably, the maleate crystal form A of compound of formula (I) has two thermal signals at about 211.2° C. and about 278.1° C. (onset temperature) in its TGA/DSC curve.

A preferred embodiment of the present application relates to a methanesulfonate crystal form B of compound of formula (I) having a powder X-ray diffraction pattern (XRPD) having one or more characteristic peaks at a diffraction angle (2θ) selected from 5.91±0.10°, 9.22±0.10°, 15.83±0.10°, 17.73±0.10°, 19.02±0.10°, and 25.01±0.10°, preferably with one or more characteristic peaks at a diffraction angle (2θ) selected from 5.91±0.10°, 9.22±0.10°, 15.83±0.10°, 17.73±0.10°, 19.02±0.10°, 20.61±0.10°, 21.36±0.10°, 23.18±0.10°, and 25.01±0.10°.

Further preferably, the methanesulfonate crystal form B of compound of formula (I) has two heat absorption signals at about 234.4° C. (peak temperature) and about 264.1° C. (onset temperature) in its TGA/DSC curve.

A preferred embodiment of the present application relates to a hydrochloride crystal form A of compound of formula (I) having a powder X-ray diffraction pattern (XRPD) having one or more characteristic peaks at a diffraction angle (2θ) selected from 8.05±0.10°, 17.11±0.10°, 18.02±0.10°, 20.84±0.10°, 21.09±0.10°, 22.77±0.10°, and 23.14±0.10°, preferably with one or more characteristic peaks at a diffraction angle (2θ) selected from 8.05±0.10°, 15.04±0.10°, 17.11±0.10°, 18.02±0.10°, 20.44±0.10°, 20.84±0.10°, 21.09±0.10°, 22.07±0.10°, 22.77±0.10°, and 23.14±0.10°.

Further preferably, the hydrochloride crystal form A of compound of formula (I) has three heat absorption peaks at about 80.1° C., about 118.0° C. (peak temperature) and about 224.5° (onset temperature), and an exothermic signal at about 231.5° C. (onset temperature) in its TGA/DSC curve.

A preferred embodiment of the present application relates to a tartrate crystal form A of compound of formula (I) having a powder X-ray diffraction pattern (XRPD) with one or more characteristic peaks at a diffraction angle (2θ) selected from 7.90±0.10°, 8.69±0.10°, 13.12±0.10°, 13.43±0.10°, 18.11±0.10°, 21.28±0.10°, and 22.90±0.10°, preferably with one or more characteristic peaks at the diffraction angle (2θ) selected from 7.90±0.10°, 8.69±0.10°, 13.12±0.10°, 13.43±0.10°, 15.08±0.10°, 17.17±0.10°, 17.44±0.10°, 18.11±0.10°, 19.40±0.10°, 20.74±0.10°, 21.28±0.10°, 22.90±0.10°, 24.15±0.10°, and 24.95±0.10°.

Further preferably, the tartarate crystal form A of compound of formula (I) have two thermal signals at about 125.2° C. and about 168.8° C. (onset temperature) in its TGA/DSC curve.

A preferred embodiment of the present application relates to a fumarate crystal form A of compound of formula (I) having a powder X-ray diffraction pattern (XRPD) with one or more characteristic peaks at a diffraction angle (2θ) selected from 4.96±0.10°, 7.66±0.10°, 10.21±0.10°, 11.06±0.10°, 14.74±0.10°, 16.11±0.10°, 22.87±0.10°, and 25.10±0.10°, preferably with one or more characteristic peaks at a diffraction angel (20) selected from 4.96±0.10°, 7.66±0.10°, 10.21±0.10°, 11.06±0.10°, 12.44±0.10°, 14.74±0.10°, 16.11±0.10°, 19.25±0.10°, 22.87±0.10°, 23.54±0.10°, 24.27±0.10°, 25.10±0.10°, 25.37±0.10°.

Further preferably, the fumarate crystal form A of compound of formula (I) have multiple thermal signals at about 71.1° C., about 205.3° C., about 273.7° C., and about 299.4° C. (onset temperature) in its TGA/DSC curve.

A preferred embodiment of the present application relates to a mucolate crystal form A of compound of formula (I) having a powder X-ray diffraction pattern (XRPD) with one or more characteristic peaks at a diffraction angle (2θ) selected from 4.98±0.10°, 10.22±0.10°, 11.07±0.10°, 14.75±0.10°, 14.94±0.10°, 16.13±0.10°, 19.65±0.10°, and 30.79±0.10°, preferably with one or more characteristic peaks at a diffraction angle (2θ) selected from 4.98±0.10°, 7.69±0.10°, 10.22±0.10°, 11.07±0.10°, 14.75±0.10°, 14.94±0.10°, 16.13±0.10°, 19.65±0.10°, 21.51±0.10°, 22.92±0.10°, and 30.79±0.10°.

Further preferably, the mucolate crystal form A of compound of formula (I) has two thermal signals at about 69.8° C. and about 210.4° C. (onset temperature) in its TGA/DSC curve.

A preferred embodiment of the present application relates to a citrate crystal form A of compound of formula (I) having a powder X-ray diffraction pattern (XRPD) with one or more characteristic peaks at a diffraction angle (2θ) selected from 4.85±0.10°, 6.42±0.10°, 14.63±0.10°, 17.12±0.10°, 20.75±0.10°, and 25.34±0.10°, preferably with one or more characteristic peaks at a diffraction angle (2θ) selected from 4.85±0.10°, 6.42±0.10°, 7.64±0.10°, 14.63±0.10°, 15.40±0.10°, 17.12±0.10°, 18.12±0.10°, 18.84±0.10°, 19.37±0.10°, 20.75±0.10°, 25.34 0.10°, and 25.34±0.10°.

Further preferably, the citrate crystal form A of compound of formula (I) has three heat absorption peaks at about 68.2° C. (peak temperature), about 154.4° C. and 164.0° C. (onset temperature) in its TGA/DSC curve.

A preferred embodiment of the present application relates to a citrate crystal form B of compound of formula (I) having a powder X-ray diffraction pattern (XRPD) with one or more characteristic peaks at a diffraction angle (2θ) selected from 4.96±0.10°, 7.67±0.10°, 10.20±0.10°, 11.04±0.10°, 14.73±0.10°, 19.23±0.10°, 22.86±0.10°, 23.54±0.10°, 24.28±0.10°, and 25.08±0.10°, preferably with one or more characteristic peaks at a diffraction angle (2θ) selected from 4.96±0.10°, 7.67±0.10°, 10.20±0.10°, 11.04±0.10°, 12.42±0.10°, 14.73±0.10°, 16.09±0.10°, 17.55±0.10°, 19.23±0.10°, 22.86±0.10°, 23.54±0.10°, 24.28±0.10°, 25.08±0.10°, and 27.91±0.10°.

Further preferably, the citrate crystal form B of compound of formula (I) has four heat absorption peaks at about 73.1° C., about 280.2° C., about 301.6° C. (onset temperature) and about 179.7° C. (peak temperature) in its TGA/DSC curve.

A preferred embodiment of the present application relates to a p-toluenesulfonate crystal form A of compound of formula (I) having a powder X-ray diffraction pattern (XRPD) with one or more characteristic peaks at a diffraction angle (2θ) selected from 5.90±0.10°, 9.34±0.10°, 14.87±0.10°, 15.33±0.10°, 17.88±0.10°, 18.76±0.10°, 19.71±0.10°, 24.26±0.10°, preferably with one or more characteristic peaks at a diffraction angle (2θ) selected from 5.90±0.10°, 9.34±0.10°, 12.99±0.10°, 14.87±0.10°, 15.33±0.10°, 16.10±0.10°, 17.88±0.10°, 18.76±0.10°, 19.34±0.10°, 19.71±0.10°, 20.39±0.10°, 24.26±0.10°, and 24.99±0.10°.

Further preferably, the p-toluenesulfonate crystal form A of compound of formula (I) has two thermal signals at about 121.2° C. and about 222.3° C. (onset temperature) in its TGA/DSC curves.

A preferred embodiment of the present application relates to a benzenesulfonate crystal form A of compound of formula (I) having a powder X-ray diffraction pattern (XRPD) with one or more characteristic peaks at a diffraction angle (2θ) selected from 5.82±0.10°, 6.74±0.10°, 11.85±0.10°, and 16.38±0.10°, preferably with one or more characteristic peaks at a diffraction angle (2θ) selected from 5.82±0.10°, 6.74±0.10°, 11.85±0.10°, 16.38±0.10°, 19.46±0.10°, and 20.20±0.10°.

Further preferably, the benzenesulfonate crystal form A of compound of formula (I) has multiple thermal signals at about 60-200° C. in its TGA/DSC curve.

A preferred embodiment of the present application relates to a benzenesulfonate crystal form B of compound of formula (I) having a powder X-ray diffraction pattern (XRPD) with one or more characteristic peaks at a diffraction angle (2θ) selected from 4.93±0.10°, 5.63±0.10°, 9.02±0.10°, 10.89±0.10°, 14.84±0.10°, 17.55±0.10°, 18.84±0.10°, 23.12±0.10°, 25.55±0.10°, and 26.14±0.10°, preferably with one or more characteristic peaks at a diffraction angle (2θ) selected from 4.93±0.10°, 5.63±0.10°, 9.02±0.10°, 10.30±0.10°, 10.89±0.10°, 11.43±0.10° 14.23±0.10°, 14.84±0.10°, 17.04±0.10°, 17.55±0.10°, 18.84±0.10°, 19.66±0.10°, 20.24±0.10°, 22.71±0.10°, 23.12±0.10°, 24.91±0.10°, 25.55±0.10°, 26.14 0.10°, 26.14±0.10°.

Further preferably, the benzenesulfonate crystal form B of compound of formula (I) has two thermal signals at about 90.1° C. (peak temperature) and about 236.7° C. (onset temperature) in its TGA/DSC curve.

In the most preferred embodiment of the present application, said solid form is phosphate crystal form A of compound of formula (I), maleate crystal form A of compound of formula (I), methanesulfonate crystal form B of compound of formula (I), crystal form A of a hydrate of compound of formula (I), and crystal form B of compound of formula (I), each of which has substantially the same XPRD spectrum as the corresponding crystal form described in the "Examples" section of the present disclosure.

In some embodiments of the present application, said solid forms is phosphate crystal form A of compound of formula (I), maleate crystal form A of compound of formula (I), methanesulfonate crystal form B of compound of formula (I), crystal form A of a hydrate of compound of formula (I), crystal form B of compound of formula (I), each of which has substantially the same TGA and/or DSC curves as the corresponding crystal form described in the "Examples" section of the present disclosure.

In a second aspect, the present disclosure provides a pharmaceutical composition comprising the solid form as mentioned in the first aspect of the present disclosure, and one or more pharmaceutically acceptable carriers, adjuvants or excipients.

The pharmaceutical composition of the present application may be a solid composition or a liquid composition (e.g., a dispersion or a solution).

The pharmaceutical compositions of the invention may be formulated as suitable dosage forms for oral, external (including not limited to external application, spraying, and the like), parenteral (including subcutaneous, intramuscular, intradermal and intravenous), bronchial or nasal administration as desire. Preferably, the pharmaceutical compositions of the invention may be formulated as suitable dosage forms for external administration, or bronchial administration or nasal administration. More preferably, the pharmaceutical compositions of the invention may be formulated as suitable dosage forms for external administration.

If a solid carrier is used, the preparation may be tableted, placed in a hard gelatin capsule in powder or pellet form, or in the form of a troche or lozenge. The solid carrier may contain conventional excipients such as binding agents, fillers, tableting lubricants, disintegrants, wetting agents and the like. The tablet may, if desired, be film coated by conventional techniques. If a liquid carrier is employed, the preparation may be in the form of a syrup, emulsion, paste, soft gelatin capsule, sterile vehicle for injection, an aqueous or non-aqueous liquid suspension, or may be a dry product for reconstitution with water or other suitable vehicle before use. Liquid preparations may contain conventional additives such as suspending agents, emulsifying agents, wetting agents, non-aqueous vehicle (including edible oils), preservatives, as well as flavoring and/or coloring agents. For parenteral administration, a vehicle normally will comprise sterile water, at least in large part, although saline solutions, glucose solutions and like may be utilized. Injectable suspensions also may be used, in which case conventional suspending agents may be employed. Conventional preservatives, buffering agents and the like also may be added to the parenteral dosage forms. The pharmaceutical compositions are prepared by conventional techniques appropriate to the desired preparation containing appropriate amounts of the active ingredient, that is, the compound of Formula (I) according to the invention.

Compositions suitable for parenteral injection may comprise physiologically acceptable sterile aqueous or nonaqueous solutions, dispersions (such as suspensions or emulsions), and sterile powders for reconstitution into sterile injectable solutions or dispersions. Examples of suitable aqueous and nonaqueous carriers, diluents, solvents, or dispersing medium include water, ethanol, polyols (propyleneglycol, polyethyleneglycol, glycerol, and the like), suitable mixtures thereof, vegetable oils (such as olive oil), and injectable organic esters such as ethyl oleate.

These compositions may also contain excipients such as preserving, wetting, emulsifying, and dispensing agents. Prevention of the action of microorganisms can be ensured by various antibacterial and antifungal agents, for example, parabens, chlorobutanol, phenol, sorbic acid, and the like. It may also be desirable to include isotonic agents, for example sugars, sodium chloride, and the like. Prolonged absorption of the injectable pharmaceutical form can be brought about by the use of agents delaying absorption, for example, aluminum monostearate and gelatin.

Solid dosage forms for oral administration include capsules, tablets, pills, powders, and granules. In such solid dosage forms, the active compound is admixed with at least one inert customary excipient (or carrier) such as sodium citrate or dicalcium phosphate or (a) fillers or extenders, as for example, starches, lactose, sucrose, glucose, mannitol, and silicic acid; (b) binders, as for example, carboxymethylcellulose, alignates, gelatin, polyvinylpyrrolidone, sucrose, and acacia; (c) humectants, as for example, glycerol; (d) disintegrating agents, as for example, agar-agar, calcium carbonate, potato or tapioca starch, alginic acid, certain complex silicates, and sodium carbonate; (e) solution retarders, as for example paraffin; (f) absorption accelerators, as for example, quaternary ammonium compounds; (g) wetting agents, as for example, cetyl alcohol and glycerol monostearate; (h) adsorbents, as for example, kaolin and bentonite; and (i) lubricants, as for example, talc, calcium stearate, magnesium stearate, solid polyethylene glycols, sodium lauryl sulfate, or mixtures thereof.

Solid compositions of a similar type may also be employed as fillers in soft and hard-filled gelatin capsules using such excipients as lactose or milk sugar as well as high molecular weight polyethyleneglycols, and the like.

Solid dosage forms such as tablets, dragees, capsules, pills, and granules can be prepared with coatings and shells, such as enteric coatings and others well-known in the art. They may contain opacifying agents, and can also be of such composition that they release the active compound or compounds in a certain part of the intestinal tract in a delayed manner. Examples of embedding compositions which can be used are polymeric substances and waxes. The active compounds can also be in micro-encapsulated form, if appropriate, with one or more of the above-mentioned excipients.

Liquid dosage forms for oral administration include pharmaceutically acceptable emulsions, solutions, suspensions, syrups, and elixirs. In addition to the active compounds, the liquid dosage forms may contain inert diluents commonly used in the art, such as water or other solvents, solubilizing agents and emulsifiers, as for example, ethyl alcohol, isopropyl alcohol, ethyl carbonate, ethyl acetate, benzyl alcohol, benzyl benzoate, propyleneglycol, 1,3-butyleneglycol, dimethylformamide, oils, in particular, cottonseed oil, groundnut oil, corn germ oil, olive oil, castor oil and sesame oil, glycerol, tetrahydrofurfuryl alcohol, polyethyleneglycols and fatty acid esters of sorbitan or mixtures of these substances, and the like.

Besides such inert diluents, the composition can also include adjuvants, such as wetting agents, emulsifying and suspending agents, sweetening, flavoring, and perfuming agents.

Suspensions, in addition to the active compounds, may contain suspending agents, as for example, ethoxylatedisostearyl alcohols, polyoxyethylene sorbitol and sorbitan esters, microcrystalline cellulose, aluminum metahydroxide, bentonite, agar-agar and tragacanth, or mixtures of these substances, and the like.

Dosage forms for topical administration of a compound of the application include paste, powders, sprays, and inhalants. The active component is admixed under sterile conditions with a physiologically acceptable carrier and any preservatives, buffers, or propellants as may be required. Ophthalmic formulations, eye ointments, powders, and solutions are also contemplated as being within the scope of this invention.

The external dosage form of the compound of the present application may be in the form of a water-in-oil (W/O) or oil-in-water (O/W) emulsion, a multi-emulsion form, such as a water-in-oil-in-water (W/O/W) form or an oil-in-water-oil (O/W/O) emulsion, or in the form of water dispersion or lipid dispersion, gel or aerosol.

The external dosage form of the compound of the present application may contain additives and aids, such as emulsifiers, thickeners, gelling agents, water fixatives, spreading agents, stabilizers, dyes, fragrances, and preservatives. Suitable emulsifiers include stearic acid, triethanolamine and PEG-40-stearate. Suitable thickeners include glyceryl monostearate, Carbomer and PEG600. Suitable preservatives include propyl paraben and chlorocresol. Suitable spreading agents include dimethicone and polydimethylcyclosiloxane. Suitable water fixatives include polyethylene glycol, preferably polyethylene glycol 600.

The external dosage form of the compound of the present application may include pastes, lotions, gels, emulsions, microemulsions, sprays, skin patches, and the like, which can be applied topically to treat atopic dermatitis, eczema, psoriasis, and scleroderma, itching, vitiligo, hair loss and other skin diseases. In particular, the external dosage form of the compound of the present application is pastes, which can be applied topically to treat skin diseases such as atopic dermatitis, eczema, psoriasis, scleroderma, itching, vitiligo, and hair loss and other skin diseases.

The amount of the compound of formula (I) in the pharmaceutical composition and dosage form can be appropriately determined by those skilled in the art as needed. For example, the compound of formula (I) can be present in the pharmaceutical composition or dosage form in a therapeutically effective amount.

In a third aspect, the present disclosure provides use of the compound in a solid form as described in the first aspect or the pharmaceutical composition as described in the second aspect in the preparation of a medicament for the treatment and/or prevention of JAK-related diseases or disorders.

"Diseases or disorders related to JAK" include but not limited to:

Arthritis, including rheumatoid arthritis, juvenile arthritis and psoriatic arthritis;

Autoimmune diseases or disorders, including single organ or single cell type autoimmune disorders, such as Hashimoto's thyroiditis, autoimmune hemolytic anemia, pernicious anemia of autoimmune atrophic gastritis, autoimmune encephalomyelitis, autoimmune orchitis, Goodpasture's disease, autoimmune thrombocytopenia, sympathetic ophthalmia, myasthenia gravis, Graves' disease, primary biliary cirrhosis, chronic aggressive hepatitis, ulcerative colitis and membranous glomerulopathy, those involving systemic autoimmune disorders (e.g. systemic lupus erythematosus, rheumatoid arthritis, Sjogren's syndrome, Reiter's syndrome, polymyositis-dermatomyositis, systemic sclerosis, polyarteritis nodosa, multiple sclerosis and bullous pemphigoid) and other O-cell (humoral) or T-cell autoimmune diseases (including Kogan syndrome), ankylosing spondylitis, Wegener's Granuloma, autoimmune alopecia, type I diabetes or juvenile-onset diabetes or thyroiditis;

Cancer or tumor, including digestive/gastrointestinal cancer, colorectal cancer, liver cancer, skin cancer (including mast cell tumor and squamous cell carcinoma), breast cancer, ovarian cancer, prostate cancer, lymphoma, leukemia (including acute myeloid leukemia and chronic myeloid leukemia), kidney cancer, lung cancer, muscle cancer, bone cancer, bladder cancer, brain cancer, melanoma (including oral and metastatic melanoma), Kaposi's sarcoma, myeloma (including multiple myeloma), myeloproliferative disorders, proliferative diabetic retinopathy or disorders related to angiogenesis (including solid tumors);

Diabetes, including type I diabetes or diabetic complications;

Eye diseases, disorders or conditions, including autoimmune diseases of eyes, keratoconjunctivitis, vernal conjunctivitis, uveitis (including uveitis and lens uveitis related to Behcet's disease), keratitis, herpetic keratitis, keratitis conus, corneal epithelial dystrophy, leukoplakia, ocular pemphigus, Moran ulcer, scleritis, Grave's eye disease, Vogt-Koyanagi-Harada syndrome, keratoconjunctivitis sicca (dry eye), blisters, iridocyclitis, sarcoidosis, endocrine ophthalmopathy, sympathetic ophthalmia, allergic conjunctivitis, or ocular neovascularization;

Intestinal inflammation, allergies or conditions, including Crohn's disease and/or ulcerative colitis, inflammatory bowel disease, celiac disease, proctitis, eosinophilic gastroenteritis or mastocytosis; Neurodegenerative diseases, including motor neuron disease, Alzheimer's disease, Parkinson's disease, amyotrophic lateral sclerosis, Huntington's disease, neurodegenerative disease caused by cerebral ischemia or traumatic injury, stroke, glutamate neurotoxicity or hypoxia; stroke ischemia/reperfusion injury, myocardial ischemia, renal ischemia, heart attack, cardiac hypertrophy, atherosclerosis and arteriosclerosis, organ hypoxia or platelet aggregation; Skin diseases, conditions or disorders, including atopic dermatitis, eczema, psoriasis, scleroderma, itching or other pruritic conditions, vitiligo, hair loss;

Allergies, including mammalian allergic dermatitis (including allergic diseases, such as bite allergies), summer eczema, *Culex* mosquito itch syndrome (sweet itch), emphysema, inflammatory airway disease, recurrent airway obstruction, airway overreaction, or chronic obstructive pulmonary disease;

Asthma and other obstructive airway diseases, including chronic or refractory asthma, advanced asthma, bronchitis, bronchial asthma, allergic asthma, endogenous asthma, exogenous asthma or dusty asthma;

Transplant rejection, including islet transplant rejection, bone marrow transplant rejection, graft versus host disease, organ and cell transplant rejection (for example bone marrow, cartilage, cornea, heart, intervertebral disc, pancreatic islets, kidney, limbs, liver, lung, muscle, myoblasts, nerve, pancreas, skin, small intestine or trachea) or xenotransplantation; and Severe pneumonia due to influenza virus or coronavirus infection, including Sars, Mers and Covid-19 (neo-coronavirus pneumonia), especially in Covid-19 to suppress an inflammatory response and inhibit or prevent cytokine storm.

In a fourth aspect, the present disclosure provides a method for treating JAK-related diseases or disorders, the method comprising administrating to patients in need a therapeutically effective amount of the compound in a solid form as described above or the pharmaceutical composition as described above. Among them, the patient is preferably a mammal, and more preferably a human patient. The route of administration can be oral, topical (including but not limited to external application, spraying, and the like), parenteral (including subcutaneous, intramuscular, cortical, and intravenous) administration, bronchial administration, or nasal administration. Among them, it is preferably administered nasally or externally. It is more preferably administered externally.

In order to have the desired effect, a therapeutically effective amount of the solid compound or pharmaceutical composition or dosage form of the present application is usually required to be administered to the patient. The phrase "therapeutically effective amount" is a recognized term in the art. In some embodiments, the term refers to an amount necessary or sufficient to eliminate, reduce, or maintain the target of a particular therapeutic regimen. The effective amount may vary depending on factors such as diseases or conditions being treated, the specific targeting construct being administered, age of the subject, or severity of the diseases or conditions. A person of ordinary skill in the art or a physician may determine the effective amount of a particular compound empirically, without the need for excessive experimentation. In some embodiments, the therapeutically effective amount of a therapeutic agent used in vivo may depend on many factors, including: administration manner and way; and any other materials included in the drug in addition to the active agent. In vitro or in vivo tests may optionally be used to help determine the optimal dose range.

Unexpectedly, the compound of the present application demonstrated in experiments excellent efficacy as a JAK kinase inhibitor that is superior to existing JAK kinase inhibitors, such as Filgotinib or Tofacitinib, and showed good safety potentially.

The present application will be further illustrated and described below in conjunction with the drawings and specific examples.

EXAMPLES

Figure 1:
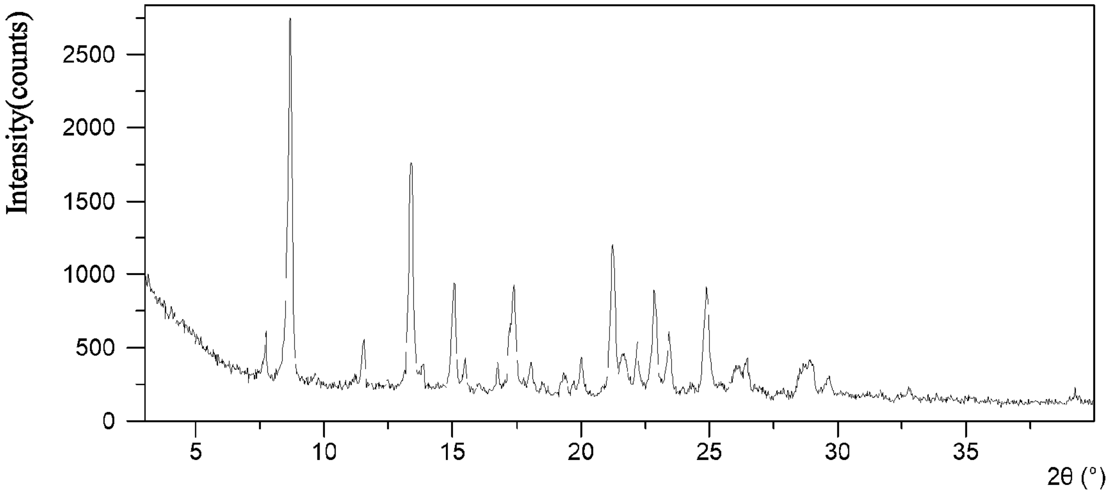
FIG. 1 illustrates an XRPD diagram for crystal form A of compound of formula (I).

The compound of the present application can be synthesized by a variety of methods familiar to those skilled in the field of organic synthesis. Exemplary methods well known in the field of synthetic chemistry for the compounds of formula (I) are given in the following examples. Obviously, with reference to the exemplary schemes in the present application, other synthetic routes for the compound of formula (I) or for other compounds can be easily designed by those skilled in the art by suitably adjusting the reactants, reaction conditions and protecting groups.

Suitable crystal or amorphous forms of the compounds of the present application can be obtained using purification, crystallization and/or drying methods familiar to those skilled in the art. Exemplary methods for the preparation of certain crystal forms and amorphous forms are given in the following examples. Obviously, referring to the exemplary embodiments of the present application, those skilled in the art can appropriately adjust solvents, equipment and process conditions to easily design the preparation process for other crystal or amorphous forms The following further describes the present application in conjunction with examples. Nevertheless, these examples do not limit the scope of the present disclosure. Unless otherwise stated, all reactants used in the examples were obtained from commercial sources; and the instrumentation and equipment used in the synthesis experiments and product analysis assays were conventional instruments and equipment normally used in organic synthesis.

Example 1: (S)-(2-(6-(2-ethyl-5-fluoro-4-hydroxyphenyl)-1H-indazol-3-yl)-4,6-dihydropyrrolo[3,4-d]imidazol-5-(1H)-yl) (3-hydroxy pyrrolidin-1-yl) ketone (I)

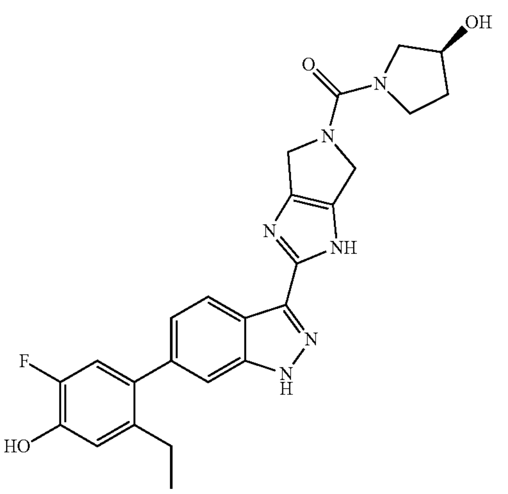

In order to synthesize the compound of formula (I), intermediate 1-1 to intermediate 1-15 were first synthesized, and then the intermediate 1-15 was used as a raw material to synthesize the compound of formula (I).

Unless otherwise specified, the chemical reagents, solvents and reaction equipment used in each chemical reaction of Example 1 were conventional materials and equipment used in chemical synthesis and were readily available through commercial sources.

I. Synthesis of Intermediate 1-6: Tert-butyl 3,4-diaminopyrrolidinyl-1-carboxylate The intermediate 1-6 was synthesized through the following synthetic route.

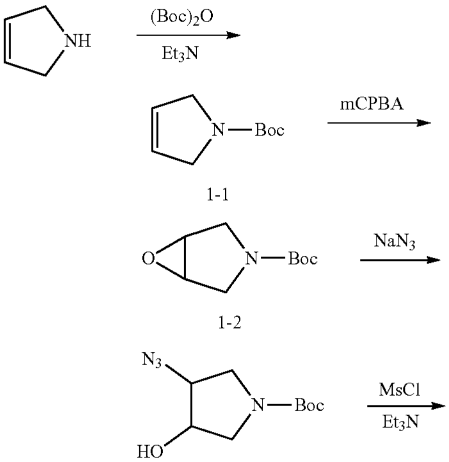

1-1

1-2

1-3

-continued

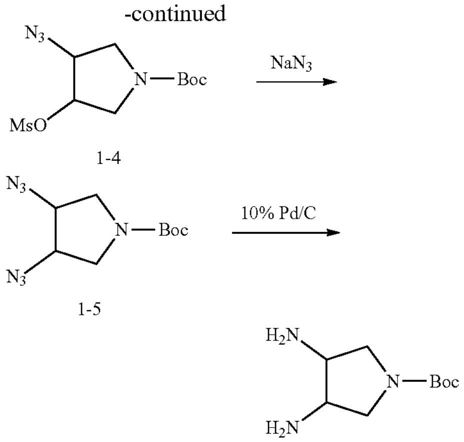

1-4

1-5

1-6

1. Synthesis of Intermediate 1-1: Tert-butyl 2,5-dihydro-1H-pyrrole-1-carboxylate 3-pyrroline (10.0 g, 0.15 mol) was dissolved in 400 ml dichloromethane and triethylamine (40.6 ml, 0.29 mol), and then cooled to 0° C. $(Boc)_2O$ (37.9 g, 0.17 mol) was slowly added. The reaction was carried out at room temperature overnight. Water was added and the mixture was extracted twice with dichloromethane. The organic phases was combined, washed with water three times, washed with saturated brine, dried over anhydrous sodium sulfate, concentrated, and purified by silica gel column to afford Intermediate 1-1 with a yield of 91.0%.

2. Synthesis of Intermediate 1-2: Tert-butyl 6-oxa-3-azabicyclo[3.1.0]hexane-3-carboxylate Intermediate 1-1 (24.5 g, 0.15 mol) was dissolved in 450 ml of dichloromethane, and then cooled to 0° C. M-chloroperoxybenzoic acid (37.5 g, 0.22 mol) was slowly added in batches. The reaction was carried out at room temperature overnight. After that, saturated sodium thiosulfate (40 ml) was added, and then stirred for 30 minutes. The aqueous phase was extracted twice with dichloromethane, washed with saturated potassium carbonate solution, water and saturated brine, dried over anhydrous sodium sulfate, concentrated, and purified by silica gel column to afford Intermediate 1-2 with a yield of 84.9%.

$^1H$ NMR (400 MHz, CDCl3) δ 3.85 (d, J=12.0 Hz, 1H), 3.77 (d, J=12.0 Hz, 1H), 3.69-3.67 (m, 2H), 3.36-3.30 (m, 2H), 1.45 (s, 9H).

3. Synthesis of Intermediate 1-3: Tert-butyl 3-azido-4-hydroxyl pyrrolidinyl-1-carboxylate Intermediate 1-2 (20.8 g, 0.12 mol) was dissolved in 150 ml 1,4-dioxane and 50 ml water, and then sodium azide (24.0 g, 0.37 mol) was added. The mixture was heated to 106° C. and reacted for 18 hours, then cooled to room temperature, followed by adding 100 ml of saturated brine. The resulting mixture was extracted with dichloromethane (250 ml×4), and the organic phases were combined, washed with saturated brine, dried over anhydrous sodium sulfate, and concentrated to afford Intermediate 1-3, with a yield of 100%.

$^1$H NMR (400 MHz, CDCl3) δ 4.27-4.24 (m, 1H), 3.94 (s, 1H), 3.73-3.59 (m, 2H), 3.41-3.36 (m, 2H), 1.47 (s, 9H).

4. Synthesis of Intermediate 1-4: Tert-butyl 3-azido-4-((methanesulfonyl)oxy) pyrrolidinyl-1-carboxylate Intermediate 1-3 (28.0 g, 0.12 mol) was dissolved in 350 ml of dichloromethane and triethylamine (37.3 g, 0.37 mol), and cooled to 0° C., followed by slowly adding methanesulfonyl chloride (16.9 g, 0.15 mol) dropwise. After the addition, the reaction was carried out at room temperature for 2 hours, the reaction was quenched with water, and the resulting mixture was extracted twice with dichloromethane. The organic phases was combined, washed with saturated sodium bicarbonate solution, water and saturated brine, dried over anhydrous sodium sulfate, and concentrated to afford Intermediate 1-4, with a yield of 98.0%.

5. Synthesis of Intermediate 1-5: Tert-butyl 3,4-diazidopyrrolidinyl-1-carboxylate Intermediate 1-4 (36.9 g, 0.12 mol) was dissolved in 250 ml DMF, to which sodium azide (23.5 g, 0.36 mol) was added. The mixture was heated to 90° C., reacted for 2 days, and cooled to room temperature, following by adding 750 ml of water. The resulting mixture was extracted with butyl tert-butyl ether (400 ml*4), and the organic phases were combined, washed with saturated brine, dried with anhydrous sodium sulfate, and purified by silica gel column to afford Intermediate 1-5 with a yield of 62.2%.

6. Synthesis of Intermediate 1-6: Tert-butyl 3,4-diaminopyrrolidinyl-1-carboxylate Intermediate 1-5 (18.9 g, 0.08 mol) was dissolved in 200 ml methanol, and 10% Pd/C was added where the atmosphere was displaced with hydrogen 3 times. The mixture was heated to 40° C., and reacted for 2 days. The resulting mixture was filtered and concentrated to afford Intermediate 1-6, with a yield of 78%.

$^1$H NMR (400 MHz, CDCl3) δ 3.51-3.49 (m, 2H), 3.40-3.36 (m, 2H), 3.21-3.11 (m, 2H), 1.47 (s, 9H).

II. Synthesis of intermediate 1-10:2-(4-(benzyloxy)-2-ethyl-5-fluorophenyl)-4,4,5,5-tetramethyl-1,3,2-dioxaborolane The intermediate 1-10 was synthesized through the following synthetic route.

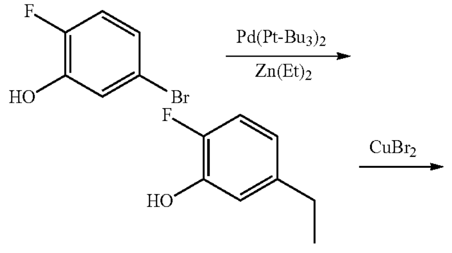

1-7

-continued

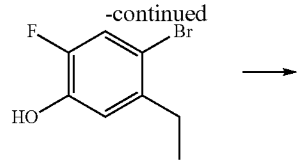

1-8

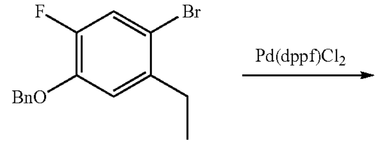

1-9

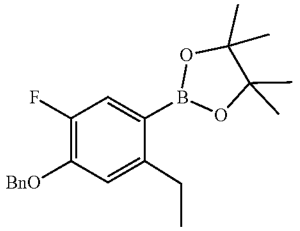

1-10

1. Synthesis of Intermediate 1-7:5-ethyl-2-fluorophenol 5-bromo-2-fluorophenol (200.0 mg, 1.05 mmol) and bis (tri-tert-butylphosphorus) palladium (10.7 mg, 0.02 mmol) were dissolved in 10 ml THF. The atmosphere was displaced with nitrogen, which was repeated 3 times. The temperature was lowered to 10-20° C. 1 mol/L diethyl zinc solution (2.3 ml, 2.30 mmol) was added dropwise slowly. After the addition was completed, the temperature was heated up to 50° C. It was allowed to react overnight, and the temperature was cooled to 0° C. The reaction was quenched with water, and filtered with celite. The celite pad was washed with ethyl acetate. The resulting filtrate was extracted with ethyl acetate, and the organic phases were combined, washed with saturated sodium chloride solution, and dried over anhydrous sodium sulfate. After drying, it was concentrated and separated by column chromatography to afford an oily liquid as intermediate 1-7 with a yield of 65.1%.

$^1$H NMR (400 MHz, $CDCl_3$) δ6.97 (d, J=8.0 Hz, 1H), 6.85 (d, J=12.0 Hz, 1H), 6.69-6.65 (m, 1H), 2.61-2.55 (m, 2H), 1.21 (t, J=8.0 Hz, 3H).

2. Synthesis of Intermediate 1-8:4-bromo-5-ethyl-2-fluorophenol

Intermediate 1-7 (200.1 mg, 1.43 mmol) was dissolved in 6 ml of acetonitrile, to which $CuBr_2$ (957.5 mg, 4.29 mmol) was added. The mixture was stirred at room temperature for 3 hours. The reaction was quenched with water, extracted with ethyl acetate, and the organic phase was washed with saturated sodium chloride solution and dried over anhydrous sodium sulfate. It was concentrated and separated by column chromatography to afford a colorless oil as intermediate 1-8, with a yield of 78.1%.

$^1$H NMR (400 MHz, CDCl3) δ7.25 (d, J=12.0 Hz, 1H), 6.89 (d, J=12.0 Hz, 1H), 2.69-2.63 (m, 2H), 1.19 (t, J=12.0 Hz, 3H).

3. Synthesis of Intermediate 1-9:1-(benzyloxy)-4-bromo-5-ethyl-2-fluorobenzene

Intermediate 1-8 (15.5 g, 70.8 mmol) was dissolved in 200 ml DMF, to which potassium carbonate (19.5 g, 141.5 mmol) and benzyl bromide (14.5 g, 84.9 mmol) were added. The mixture was heated to a temperature of 60° C. for reaction. After the reaction was complete, it was quenched with water, extracted with EA, and the organic phase was washed with saturated sodium chloride solution and dried over anhydrous sodium sulfate. After concentration, column chromatography gave 19.0 g of Intermediate 1-9 with a yield of 86.8%, $^1$H NMR (400 MHz, CDCl3) δ 7.44-7.31 (m, 5H), 7.27 (d, J=8.0 Hz, 1H), 6.87 (d, J=8.0 Hz, 1H), 5.12 (s, 2H), 2.68-2.63 (m, 2H), 1.16 (t, J=8.0 Hz, 3H).

4. Synthesis of Intermediate 1-10:2-(4-(benzyloxy)-2-ethyl-5-fluorophenyl)-4,4,5,5-tetramethyl-1,3,2-dioxaborolane Intermediates 1-9 (1.0 g, 3.23 mmol), pinacol borate (0.82 g, 3.23 mmol), Pd(dppf)Cl2 (0.24 g, 0.32 mmol) and KOAc (0.95 g, 9.70 mmol) were dissolved in 15 ml of 1,4-dioxaborolane where the atmosphere was displaced with nitrogen 3 times. The mixture was heated to 100° C. for reaction. After the reaction was complete, it was quenched with water, extracted with ethyl acetate and the organic phase was washed with saturated sodium chloride solution and dried over anhydrous sodium sulfate. After concentration, column chromatography gave 0.98 g of Intermediate 1-10 with a yield of 85.1%, $^1$H NMR (400 MHz, CDCl3) δ 7.50-7.30 (m, 6H), 7.82 (d, J=8.0 Hz, 1H), 5.16 (s, 2H), 2.87-2.81 (m, 2H), 1.32 (s, 12H), 1.14 (t, J=8.0 Hz, 3H).

III. Synthesis of intermediate 1-15: tert-butyl 2-(6-bromo-1-((2-(trimethylsilyl) ethoxy)methyl)-1H-indazol-3-yl)-1-((2-(trimethylsilyl) ethoxy)methyl)-4,6-dihydropyrrolo[3,4-d]imidazole-5 (1H)-carboxylate Intermediate 1-15 was synthesized through the following synthetic route.

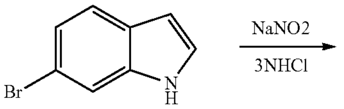

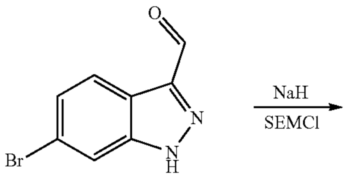

1-11

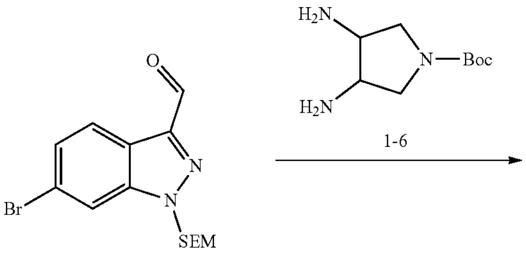

1-6

1-12

-continued

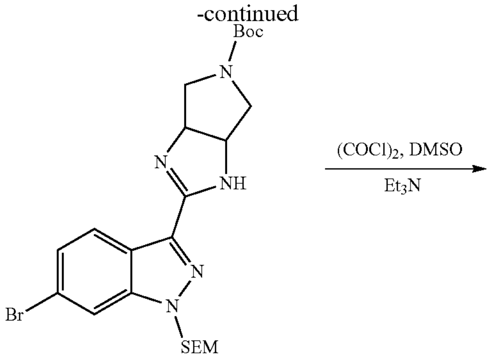

1-13

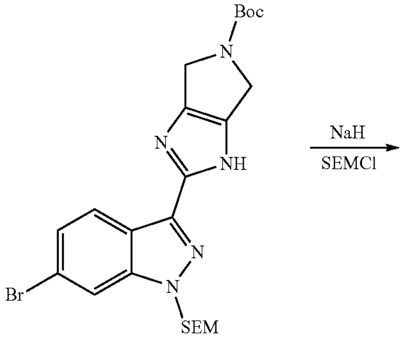

1-14

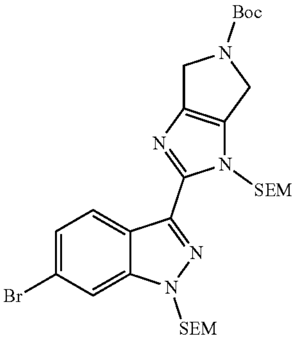

1-15

1. Synthesis of Intermediate 1-11:6-bromo-1H-indazole-3-carbaldehyde

Sodium nitrite (14.00 g, 200 mmol) was dissolved in 75 ml DMF and 100 ml water, and the solution was cooled to 0° C. Under nitrogen protection, 3N HCl (23 ml, 68.9 mmol) was added slowly dropwise and it was allowed to react for 10 min after dropwise addition. At 0° C., 6-bromoindole (5.00 g, 25.5 mmol) in DMF (35 ml) was added to the reaction solution slowly dropwise. After the addition, it was allowed to react at room temperature overnight. The reaction solution was extracted 3 times with ethyl acetate, and the resulting organic phases were combined, washed 3 times with water, and with saturated brine, dried over anhydrous sodium sulfate, and concentrated and purified by silica gel column to give intermediates 1-11 with a yield of 83.6%.

$^1$H NMR (400 MHz, $CDCl_3$) δ 10.29 (s, 1H), 8.24 (d, J=8.0 Hz, 1H), 7.80 (d, J=4.0 Hz, 1H), 7.52 (dd, J=8.0 Hz, J=4.0 Hz, 1H).

2. Synthesis of Intermediate 1-12:6-bromo-1-((2-(trimethylsilyl) ethoxy)methyl)-1H-indazole-3-carbaldehyde Intermediate 1-11 (1.56 g, 6.93 mmol) was dissolved in dry tetrahydrofuran, and the solution was cooled to 0° C., to which sodium hydride (0.33 g, 8.32 mmol) was added dropwise slowly. It was allowed to react at room temperature for 1 hour. The reaction solution was cooled to 0° C., and 2-(trimethylsilyl) ethoxymethyl chloride (1.73 g, 10.40 mmol) was add dropwise slowly. It was allowed to react overnight at room temperature after dropwise addition. The reaction was quenched with water, extracted twice with ethyl acetate, and the resulting organic phases were combined, washed with water and saturated brine, dried over anhydrous sodium sulfate, concentrated and purified by silica gel column to give Intermediates 1-12 with a yield of 49.2%.

$^1$H NMR (400 MHz, $CDCl_3$) δ 10.25 (s, 1H), 8.22 (dd, J=8.0 Hz, J=4.0 Hz 1H), 7.88 (dd, J=4.0 Hz, J=4.0 Hz, 1H), 7.52 (dd, J=4.0 Hz, J=4.0 Hz, 1H), 5.81 (s, 2H), 3.63-3.58 (m, 2H), 0.97-0.93 (m, 2H), 0.04 (s, 9H).

3. Synthesis of Intermediate 1-13: tert-butyl 2-(6-bromo-1-((2-(trimethylsilyl) ethoxy)methyl)-1H-indazol-3-yl)-3,4,6,6a-tetrahydropyrrolo[3,4-d]imidazole-5 (1H)-carboxylate Intermediate 1-12 (1.56 g, 6.93 mmol) and tert-butyl 3,4-diaminopyrroline-1-carboxylate (1.56 g, 6.93 mmol) were dissolved in 5 ml of hexafluoroisopropanol, and the solution was heated to 40° C. and allowed to react for 2 days. The reaction solution was concentrated and purified by silica gel column to give Intermediate 1-13 with a yield of 54.7%.

4. Synthesis of Intermediate 1-14: tert-butyl 2-(6-bromo-1-((2-(trimethylsilyl) ethoxy)methyl)-1H-indazol-3-yl)-4,6-dihydropyrrolo[3,4-d]imidazole-5 (1H)-carboxylate Under nitrogen protection, oxalyl chloride (0.53 g, 4.20 mmol) was dissolved in 15 ml of dry dichloromethane, and the solution was cooled to −78° C., to which DMSO (0.61 g, 7.84 mmol) was added slowly dropwise. After the addition was completed, it was allowed to react for 30 min, to which Intermediate 1-13 (1.00 g, 1.87 mmol) in dichloromethane was added slowly dropwise. After the addition was completed, it was allowed to react for 30 minutes, to which dry triethyl amine (1.89 g, 18.66 mmol) was added slowly dropwise. After the addition was completed, it was allowed to react for 10 minutes. Then, the reaction mixture was slowly increased to room temperature and was allowed to react for 2 h. The reaction was quenched by adding saturated ammonium chloride solution, extracted twice with dichloromethane, and the resulting organic layers were combined, washed with water and saturated brine, dried over anhydrous sodium sulfate, concentrated and purified by silica gel column to give Intermediate 1-14 with a yield of 36.3%.

$^1$H NMR (400 MHz, $CDCl_3$) δ 8.36 (d, J=4.0 Hz, 1H), 7.78 (d, J=4.0 Hz, 1H), 7.44 (dd, J=8.0 Hz, J=4.0 Hz, 1H), 5.69 (s, 2H), 4.64-4.52 (m, 4H), 3.67-3.56 (m, 2H), 1.56 (s, 9H), 0.95-0.89 (m, 2H), 0.03 (s, 9H).

5. Synthesis of Intermediate 1-15: tert-butyl 2-(6-bromo-1-((2-(trimethylsilyl) ethoxy)methyl)-1H-indazol-3-yl)-1-((2-(trimethylsilyl) ethoxy)methyl)-4,6-dihydropyrrolo[3,4-d]imidazole-5 (1H)-carboxylate Intermediate 1-14 (110 mg, 0.21 mmol) was dissolved in dry tetrahydrofuran, and the solution was cooled to 0° C., to which sodium hydride (12.3 mg, 0.31 mmol) was added. It was allowed to react at room temperature for 30 min, and the reaction solution was cooled to 0° C., to which 2-(trimethylsilyl) ethoxymethyl chloride (41.2 mg, 0.25 mmol) was added slowly dropwise, it was allowed to react at room temperature for 4 h. The reaction was quenched by adding water and extracted with ethyl acetate twice and the resulting organic phases were combined, washed with water and saturated brine, dried over anhydrous sodium sulfate, concentrated and purified by silica gel column to give Intermediates 1-15 with a yield of 73.1%.

$^1$H NMR (400 MHz, $CDCl_3$) δ 8.41-8.36 (m, 1H), 7.79 (s, 1H), 7.44 (dd, J=8.0 Hz, J=4.0 Hz, 1H), 5.94 (d, J=12.0 Hz, 2H), 5.73 (s, 2H), 4.65-4.52 (m, 4H), 3.63-3.57 (m, 4H), 1.56 (s, 9H), 0.96-0.91 (m, 4H), 0.03 (s, 18H).

IV. Synthesis of Compound of Formula (I)

The compound of formula (I) was synthesized starting from intermediate 1-15 through the following synthetic route.

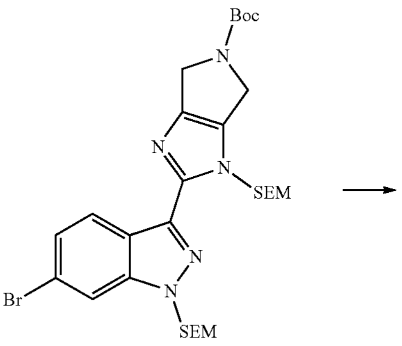

1-15

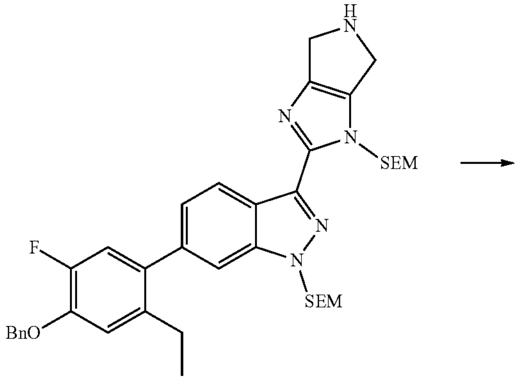

1-16

-continued

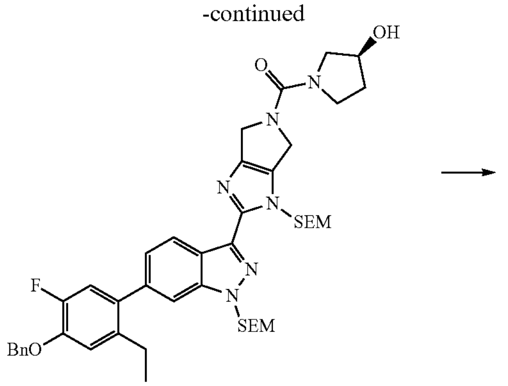

1-17

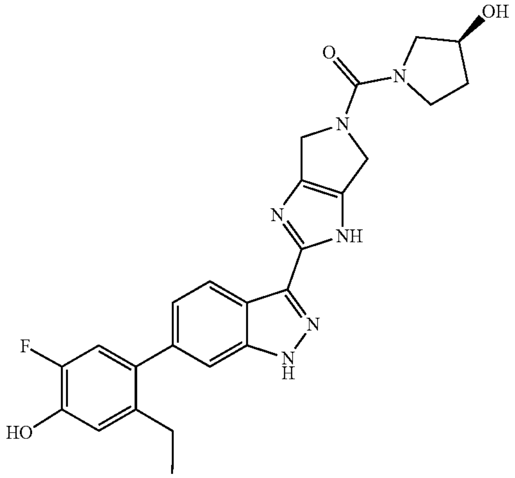

(I)

1. Synthesis of Intermediate 1-16:6-(4-(benzyloxy)-2-ethyl-5-fluorophenyl)-1-((2-(trimethylsilyl) ethoxy)methyl)-3-(1-((2-(trimethylsilyl) ethoxy) methyl)-1,4,5,6-tetrahydropyrrolo[3,4-d]imidazol-2-yl)-1H-indazole Tert-butyl 2-(6-bromo-1-((2-(trimethylsilyl) ethoxy) methyl)-1H-indol-3-yl)-1-((2-(trimethylsilyl) ethoxy) methyl)-4,6-dihydropyrrolo[3,4-d]imidazole-5 (1H)-carboxylate (500 mg, 0.75 mmol), 2-(4-(benzyloxy)-2-ethyl-5-fluorophenyl)-4,4,5,5-tetramethyl-1,3,2-dioxaborolane (401 mg, 1.13 mmol), Pd(dppf)Cl2 (75 mg, 0.075 mmol) and potassium phosphate (495 mg, 2.25 mmol) were dissolved in 1,4-dioxaborolane (30 ml) and water (6 ml), where the atmosphere was displaced with nitrogen 3 times, and the solution was heated to 100° C. It was allowed to react for 16 h. The reaction was cooled to room temperature and quenched with water and extracted with ethyl acetate twice. The resulting organic phases were combined, washed with water and saturated brine, dried over anhydrous sodium sulfate, concentrated, and purified on silica gel column. The purified product was dissolved in 25 ml of dichloromethane, to which 5 ml of trifluoroacetic acid was added dropwise, and the mixture was stirred for 30 min at room temperature, and concentrated to give a residue. The residue was dissolved in dichloromethane and concentrated to dryness (to remove trifluoroacetic acid), which was repeated 3 times. The resulting product was purified by silica gel column to afford intermediate 1-16, totaling 210 mg with a yield of 39.2%.

$^1$H NMR (400 MHz, $CDCl_3$) δ 8.48 (d, J=8.3 Hz, 1H), 7.52 (d, J=7.4 Hz, 1H), 7.49-7.37 (m, 5H), 7.25 (d, J=8.4 Hz, 1H), 7.23-6.96 (m, 2H), 5.93 (s, 2H), 5.77 (s, 2H), 5.23 (s, 2H), 4.21 (d, J=35.1 Hz, 4H), 3.66-3.52 (m, 4H), 2.54 (q, J=7.6 Hz, 2H), 1.05 (t, J=7.5 Hz, 3H), 0.95-0.89 (m, 4H) 0.89 (m, 4H), 0.02 (s, 9H), −0.05 (d, J=3.4 Hz, 9H).

2. Synthesis of Intermediate 1-17: (S)-(2-(6-(4-(benzyloxy)-2-ethyl-5-fluorophenyl)-1-((2-(trimethylsilyl) ethoxy)methyl)-1H-indazol-3-yl)-1-((2-(trimethylsilyl) ethoxy)methyl)-4,6-dihydropyrrolo [3,4-d]imidazol-5-(1H)-yl) (3-hydroxy pyrrolidin-1-yl) ketone Triphosgene (91.5 mg, 0.31 mmol) was dissolved in 10 ml of dry dichloromethane and the intermediate 6-(4-(benzyloxy)-2-ethyl-5-fluorophenyl)-1-((2-(trimethylsilyl) ethoxy) methyl)-3-(1-((2-(trimethylsilyl) ethoxy)methyl)-1-1,4,5,6-tetrahydropyrrolo[3,4-d]imidazole (220.0 mg, 0.31 mmol) in dichloromethane (5 ml) was added dropwise at 0° C. Then dry triethylamine (312.2 mg, 3.09 mmol) was added slowly dropwise. The resulting mixture was stirred at room temperature for 10 min, and was monitored by TLC until the raw material was fully consumed. (S)-pyrrolidin-3-ol (40.3 mg, 0.46 mmol) in dichloromethane (5 ml) was added at room temperature. The reaction solution was stirred at room temperature for 20 min, quenched with water, and extracted twice with dichloromethane, and the resulting organic phases were combined, washed with saturated brine, dried over anhydrous sodium sulfate, concentrated and purified by silica gel column to give 192 mg of Intermediate 1-17 with a yield of 75.3%.

$^1$H NMR (400 MHz, CDCl3) δ 8.47 (d, J=8.3 Hz, 1H), 7.53-7.51 (m, 2H), 7.47-7.35 (m, 4H), 7.25 (d, J=8.4 Hz, 1H), 7.06-6.96 (m, 2H), 5.96 (s, 2H), 5.78 (s, 2H), 5.23 (s, 2H), 4.79-4.56 (m, 4H), 4.49-4.45 (m, 1H), 3.81-3.72 (m, 2H), 3.68-3.58 (m, 5H), 3.46-3.43 (m, 1H), 2.56 (q, J=7.6 Hz, 2H), 2.09-1.96 (m, 2H), 1.16 (t, J=7.5 Hz, 3H), 0.99-0.89 (m, 4H), 0.02 (s, 9H), −0.05 (s, 9H).

3. Synthesis of compound of formula (I): (S)-(2-(6-(2-ethyl-5-fluoro-4-hydroxyphenyl)-1H-indazol-3-yl)-4,6-dihydropyrrolo[3,4-d]imidazol-5-(1H)-yl) (3-hydroxypyrrolidin-1-yl) ketone Intermediate 1-17 (22.00 g, 26.60 mmol, 1.00 eq) was added to a three neck flask having a volume of 1 L, followed by DCM (330 mL, 15 V). After Intermediate 1-17 was dissolved, the solution was cooled to −70° C. to −60° C. and stirred magnetically. The atmosphere was displaced three times with $N_2$. To the reaction solution, $BCl_3$ (133 mL, 132.99 mmol, 5.00 eq, 1 N in DCM) was added in 15 min, during which, the inner temperature was kept not greater than −55° C. After the addition was completed, the mixture was further stirred at −70° C. to −60° C. for 1h. 50 mL of methanol was added to the reaction system slowly dropwise to quench the reaction, during which the quenching temperature should not exceed −50° C., and the dropwise addition was completed in about 15 min. Then the reaction system was naturally warmed up to 15-20° C., and the reaction solution was concentrated under vacuum at 38° C. To the resulting residue, 200 mL of methanol and ammonia were added, and the mixture was stirred at 40° C. for 30 min and then subjected to rotary evaporation to remove methanol. A large amount of light yellow solid was precipitated from the system (aqueous phase), which was filtered to give a solid, which was dried to give a crude product (15.00 g).

The crude product was purified by Prep-HPLC (normal phase, 0.1% ammonia alkaline system, ethanol system), and the resulting fraction was concentrated to 200 mL at 40° C. with a large amount of solid precipitation, followed by filtration to give 5.90 g of a light yellow solid powder, which is the compound of formula (I).

$^1$H NMR (400 MHz, DMSO-d6) δ 13.25 (s, 1H), 12.69 (s, 1H), 9.84 (s, 1H), 8.32 (d, J=8.4 Hz, 1H), 7.39 (s, 1H), 7.11 (d, J=9.2 Hz, 1H), 7.03 (d, J=12 Hz, 1H), 6.92 (d, J=9.2 Hz, 1H), J=9.2 Hz, 1H), 4.92 (s, 1H), 4.74-4.53 (m, 2H), 4.51-4.35 (m, 2H), 4.27 (s, 1H), 3.58-3.49 (m, 2H), 3.45-3.37 (m, 1H), 3.23 (m, 1H), 2.49-2.45 (m, 2H, partially obscured by the solvent peak of DMSO-d6, 1.92-1.71 (m, 2H), 1.02 (t, J=7.6 Hz, 3H), 2.49-2.45 (m, 2H, partially obscured by the solvent peak of DMSO-d6)

LC-MS: $C_{25}H_{26}FN_6O_3$ $[M+H]^+$ m/z calculated as 477.2, and detected as 477.1.

Example 2: Evaluation of Pharmacological Activity of Compound of Formula (I)-I 1. Experimental Principle A drug screening system based on kinases JAK1, JAK2, JAK3, and TYK2 was used to detect the inhibitory ability of compounds on kinase activity. A kinase undergoes an enzymatic reaction with its substrates IRS1, IGF1Rtide, and Poly (4:1 Glu, Tyr), consuming ATP to produce ADP, wherein the ADP-Glo reagent and luminescence method can be used to detect the amount of the product to reflect the activity of the kinase.

2. Experimental Scheme 2.1 Experimental Materials and Instruments

| Item | Name | Source/Supplier | Catalogue No. |
|---|---|---|---|
| 1 | HEPES | Life Technologies | 15630-080 |
| 2 | BRU 35 detergent (10%) | Merck | 1018940100 |
| 3 | MgCl2 | Sigma | M1028 |
| 4 | EGTA | Sigma | E3889 |
| 5 | ADP-Glo Kinase Assay | Promega | V9101 |
| 6 | JAK1 | Carna | PV4774 |
| 7 | JAK2 | Carna | PV4210 |
| 8 | JAK3 | Carna | PV3855 |
| 9 | TYK2 | Carna | PV4790 |
| 10 | ATP | Promega | V915B |
| 11 | IRS1 | Signalchem | 140-58-1000 |
| 12 | IGF1Rtide | Signalchem | 115-58 |
| 13 | Poly (4:1 Glu, Tyr) | Sigma | P0275 |
| 15 | 384 polystyrene shallow flat white | Greiner | 784075 |
| 16 | 384-Well Polypropylene microplate | Labcyte | PP-0200 |
| 17 | Biotek Enzyme Labeler | Biotek | Synergy 4 |
| 18 | Microplate low-speed centrifuge | Xiang Zhi | TD5B |

2.2 Experimental Methods 2.2.1 Kinase Reaction Reagent Formulation 2.2.1.1 1× Kinase Reaction Buffer (400 mL)

| Name | Stock Concentration | Volume | Final Concentration |
|---|---|---|---|
| HEPES | 1M (20X) | 20 mL | 50 mM |
| $MgCl_2$ | 1M (100X) | 4 mL | 10 mM |
| BRIJ-35 | 10% (1000X) | 400 μL | 0.01% |
| EGTA | Powder | 152 mg | 1 mM |
| ddH2O | | 375.6 mL | |

2 mM DTT, Ready to Use 2.2.1.2 2× Kinase Formulation

| Name | Stock concentration | Volume | 2X Final Concentration | Final Concentration |
|---|---|---|---|---|
| JAK1 kinase solution | | | | |
| JAK1 | 3225 nM (884X) | 5.21 μL | 40 nM | 20 nM |
| 1X Kinase Reaction Buffer | | 414.79 μL | | |
| JAK2 kinase solution | | | | |
| JAK2 | 4256 nM (4955X) | 0.2 μL | 2 nM | 1 nM |
| 1X Kinase Reaction Buffer | | 419.8 μL | | |
| JAK3 kinase solution | | | | |
| JAK3 | 3195 nM (5341.2X) | 0.5 μL | 4 nM | 2 nM |
| 1X Kinase Reaction Buffer | | 419.5 μL | | |
| TYK2 kinase solution | | | | |
| TYK2 | 3174 nM (763X) | 2.65 μL | 20 nM | 10 nM |
| 1X Kinase Reaction Buffer | | 417.35 μL | | |

2.2.1.3 4× Substrate Mixture Formulation

| Name | Stock concentration | Volume | 2X Final Concentration | Final Concentration |
|---|---|---|---|---|
| JAK1 substrate mixture solution | | | | |
| ATP | 10 mM (125X) | 2.4 μL | 80 μM | 20 μM |
| IRS1 | 1 mg/mL (5X) | 60 μL | 0.2 mg/mL | 0.05 mg/mL |
| 1X Kinase Reaction Buffer | | 237.6 μL | | |

-continued

| Name | Stock concentration | Volume | 2X Final Concentration | Final Concentration |
|---|---|---|---|---|
| JAK2 substrate mixture solution | | | | |
| ATP | 10 mM (500X) | 6 μL | 20 μM | 5 μM |
| IGF1Rtide | 1 mg/mL (25X) | 12 μL | 0.04 mg/mL | 0.01 mg/mL |
| 1X Kinase Reaction Buffer | | 287.4 μL | | |
| JAK3 substrate mixture solution | | | | |
| ATP | 10 mM (250X) | 1.2 μL | 40 μM | 10 μM |
| Poly (4:1 Glu, Tyr) Peptide | 5 mg/mL (41.6X) | 6 μL | 0.12 mg/mL | 0.03 mg/mL |
| 1X Kinase Reaction Buffer | | 292.8 μL | | |
| TYK2 substrate mixture solution | | | | |
| ATP | 10 mM (250X) | 1.2 μL | 40 μM | 10 μM |
| IRS1 | 1 mg/mL (5X) | 60 μL | 0.08 mg/mL | 0.02 mg/mL |
| 1X Kinase Reaction Buffer | | 238.8 μL | | |

2.2.1.4 Compounds to be Tested

| Name | Mass/mg | Molecular weight | Concentration/ mM |
|---|---|---|---|
| Filgotinib | 5.0 | 420.5 | 10 |
| Compound of formula (I) | 1.5 | 476.51 | 10 |

2.2.2 Kinase Reaction Experiment Procedure 2.2.2.1 JAK1 & JAK2 Kinase Reaction Experimental Procedure a) Diluting a compound solution to be tested by 5 times with 100% DMSO. Then, using 100% DMSO as diluent, performing a series of dilutions at a ratio of 1:3 for Filgotinib (10 mM stock solution) and the compound solution to be tested in a 96-well dilution plate. Taking out 1 μL of the compound solution and adding it to 49 μL of kinase reaction buffer, and shaking the resulting mixture on a microplate shaker for 20 minutes.

b) Transferring 2 μL of kinase (prepared according to 2.2.1.2) to a 384-well reaction plate, adding 1 μL of the compound solution to be tested (prepared in step a) to the 384-well reaction plate (Greiner, 784075), centrifuging it at 1000 rpm/min for 1 min and incubating it at 25° C. for 10 min.

c) Transferring 1 μL of the substrate mixture (prepared according to 2.2.1.3) to the 384-well reaction plate, centrifuging it at 1000 rpm/min for 1 min, and incubating it at 25° C. for 60 min. In the reaction system, the final concentrations of Filgotinib are 50, 12.5, 3.125, 0.7812, 0.1953, 0.0488, 0.0122, 0.003, 0.00076, 0.00019, and 0.000047 μM. The final concentrations of the compound to be tested are: 10, 2.5, 0.625, 0.15625, 0.039, 0.0097, 0.0024, 0.0006, 0.0015, 0.000038, and 0.0000095 μM. The final concentration of DMSO is 0.5%.

d) Transferring 4 μL of ADP-Glo to the 384-well reaction plate, centrifuging it at 1000 rpm/min for 1 min, and incubating it at 25° C. for 40 min.

e) Transferring 8 μL of Detection solution to the 384-well reaction plate, centrifuging it at 1000 rpm/min for 1 min, and incubating it at 25° C. for 40 min.

f) Using Biotek multi-function plate reader to read the RLU (Relative luminescence unit) signal. The signal intensity is used to characterize the degree of kinase activity.

2.2.2.2 JAK3 & TYK2 Kinase Reaction Experimental Procedure a) Diluting a compound solution to be tested by 5 times with 100% DMSO. Then, using 100% DMSO as diluent, performing a series of dilutions at a ratio of 1:3 for Filgotinib (10 mM stock solution) and the compound solution to be tested in a 96-well dilution plate. Taking out 1 μL of the compound solution and adding it to 49 μL of kinase reaction buffer, and shaking the resulting mixture on a microplate shaker for 20 minutes.

b) Transferring 2 μL of kinase (prepared according to 2.2.1.2) to a 384-well reaction plate, and adding 1 μL of the compound solution to be tested (prepared in step a) to the 384-well reaction plate (Greiner, 784075), centrifuging it at 1000 rpm/min for 1 min and incubating it at 25° C. for 10 min.

c) Transferring 1 μL of the substrate mixture (prepared according to 2.2.1.3) to the 384-well reaction plate, centrifuging it at 1000 rpm/min for 1 min, and incubating it at 25° C. for 60 min. In the reaction system, the final concentrations of Filgotinib are 50, 16.67, 5.555, 1.851, 0.617, 0.205, 0.0686, 0.0228, 0.00762, and 0.0025 μM. The final concentrations of the compound to be tested are 10, 3.33, 1.11, 0.37, 0.12, 0.04, 0.014, 0.0046, 0.0015, and 0.0005 μM. The final concentration of DMSO is 0.5%.

d) Transferring 4 μL of ADP-Glo to the 384-well reaction plate, centrifuging it at 1000 rpm/min for 1 min, and incubating it at 25° C. for 40 min.

e) Transferring 8 μL of Detection solution to the 384-well reaction plate, centrifuging it at 1000 rpm/min for 1 min, and incubating it at 25° C. for 40 min.

f) Using Biotek multi-function plate reader to read the RLU (Relative luminescence unit) signal. The signal intensity is used to characterize the degree of kinase activity.

2.2.3 Experimental Data Processing Method

Compound inhibition rate (% inh)=(negative control−compound)/(negative control−positive control)*100%

Negative control: DMSO

Positive control: 10 μM/100 μM/30 μM Filgotinib

IC50 (half inhibitory concentration) of the compound can be obtained using the following nonlinear fitting formula:

$$Y=\text{Bottom}+(\text{Top}-\text{Bottom})/(1+10\hat{}((\text{Log IC50}-X)*\text{HillSlope}))$$

X: log value of the compound concentration

Y: Compound inhibition rate (% inh)

Z' factor calculation equation:

$$Z'=1-3(SDmin+SDmax)/(AVEmax-AVEmin)$$

in which:

Min is the RLU value of the positive control 10 μM/100 μM/30 μM Filgotinib, and Max is the RLU value of the negative control DMSO; and SD is the standard error, and AVE is the average value of RLU.

3. Results

The results of the compound assays are shown in the following table.

| Assays | Compound | IC50 (nM) |
|---|---|---|
| JAK1 assay | Filgotinib | 88 |
| | Compound of formula (I) | 0.134 |
| JAK2 assay | Filgotinib | 71 |
| | Compound of formula (I) | 0.233 |
| JAK3 assay | Filgotinib | 1463 |
| | Compound of formula (I) | 0.247 |
| TYK2 assay | Filgotinib | 532 |
| | Compound of formula (I) | 1.62 |

The test results show that the inhibitory activity of the compound of formula (I) obtained in Example 1 is much higher than that of Filgotinib, in particular by more than two orders of magnitude, and can effectively inhibit JAK1, JAK2, JAK3 and TYK2 at very low concentrations.

Example 3: Evaluation of Pharmacological Activity of Compound of Formula (I)-II 1. Experimental Principle The purpose of this example is to assay the activity of the compound in the JAK cell activity assay-human T cell proliferation assay.

2. Experimental Scheme 2.1 Experimental Materials and Instruments

| Item | Name | Source/Supplier | Catalogue No. |
|---|---|---|---|
| 1 | Human PBMC Cryopreserved | TPCS | PB050C |
| 2 | RPMI Medium 1640 | Invitrogen | A10491-01 |
| 3 | Fetal bovine serum | Invitrogen | 10099-141 |
| 4 | Penicillin-streptomycin | Invitrogen | 15140-122 |
| 5 | DMSO | MP | 196055 |
| 6 | Pan T Cell Isolation Kit, human | Miltenyi Biotech | 130-096-535 |
| 7 | Recombinant Human IL-2 Protein | R&D | 202-IL-010 |
| 8 | anti-CD3 human OKT3 | eBioscience | EB16-0037-85 |
| 9 | CD28 Monoclonal Antibody (CD28.2), Functional Grade | eBioscience | 16-0289-85 |
| 10 | Tofacitinib | Selleck | S2789 |
| 11 | Celltiter Glo assay kit | Promega | G7573 |
| 12 | 384 well plate | Corning | 3764 |
| 13 | 6 well plate | Corning | 3516 |
| 15 | Plate Reader | PerkinElmer | Envision 2104 |
| 16 | Centrifuge | Eppendorf | 5810R |
| 17 | Echo 550 | PerkinElmer | 6008280 |

2.2 Experimental Methods 2.2.1 Formulation of the Compound Stocks to be Tested

Formulation of compound stocks

| Compound | Molecular weight | Weighing mass (mg) | Volume of DMSO added (μL) | DMSO stock concentration (mM) |
|---|---|---|---|---|
| Tofacitinib | 312.37 | 5.00 | 1600.70 | 10 |
| Compound of formula (I) | 476.51 | 1.7 | 342.49 | 10 |

2.2.2 Experimental Steps of Kinase Reaction a) Isolating T cells from human PBMC using the Human Pan T Cell Isolation Kit according to the manual.

b) Stimulating the T cells with anti-CD3 antibody and anti-CD28 antibody and incubating them for 72 h at 37° C. in a 5% $CO_2$ incubator.

c) Collecting T cells and washing the cells with PBS.

d) Transferring 40 nL of the diluted compound solution to be tested to a 384-well plate using Echo 550.

e) Inoculating the T cells (prepared in step c) into the 384-well reaction plate (prepared in step d) in an amount of 35 μL/well, centrifuging at 1000 rpm for 1 min, and incubating at 37° C. with 5% $CO_2$.

f) Adding 5 μL/well of human recombinant IL-2 protein at a final concentration of 10 ng/ml, then centrifuging at 1000 rpm for 1 min, and incubating for 72 h at 37° C. with 5% $CO_2$.

g) Adding 20 μL Celltiter Glo buffer per well, centrifuging at 1000 rpm for 1 min, mixing at 350 g for 2 min, and incubating at room temperature for 30 min.

h) Reading the lumilencence signal values on the EnVision multifunctional plate reader.

2.2.3 Experimental Data Processing Method

Compound inhibition rate (% inh)=(negative control−compound)/(negative control−positive control)*100%

Negative control: DMSO

Positive control: 10 μM Tofacitinib

IC50 (half inhibitory concentration) of the compound can be obtained using the following nonlinear fitting formula:

$$Y=Bottom+(Top-Bottom)/(1+10^{\wedge}((Log\ IC50-X)*HillSlope))$$

X: log value of the compound concentration

Y: Compound inhibition rate (% inh)

3. Results

The results of the compound assays are shown in the following table.

| Compound | IC50 (nM) |
|---|---|
| Tofacitinib | 21.74 |
| Compound of formula (I) | 13.01 |

The test results show that the compound of formula (I) exhibits superior activity over Tofacitinib in IL-2 induced human T cell proliferation assay.

Example 4: Study on Crystal Forms of Compound of Formula (I)

The polymorphism phenomenon of the compound of formula (I) in Example 1 (sometimes referred to as "the free base" because of its basic nature) was investigated by varying crystallization methods, and the various crystal forms were characterized and identified by X-ray powder diffraction (XRPD), thermogravimetric analysis (TGA), differential scanning calorimetry (DSC), nuclear magnetic resonance hydrogen spectroscopy ($^1$H NMR) and other methods in order to provide a basis for the production and formulation of pharmaceutical preparations.

I. Instruments and Measurement Methods

1) X-Ray Powder Diffraction (XRPD)

XRPD patterns were collected on a PANalytical X-ray powder diffraction analyzer using the scanning parameters shown in the table below.

TABLE 1 parameters of XRPD

| Parameter | XRPD (reflection mode) | XRPD (Variable temperature mode) | XRPD (reflection mode) |
|---|---|---|---|
| Model | Empyrean | Empyrean | X'Pert$^3$ |
| X-Ray | Cu, kα, Kα1 (Å): 1.540598; Kα2 (Å): 1.544426; Kα2/Kα1 intensity ratio: 0.50 | Cu, kα, Kα1 (Å): 1.540598; Kα2 (Å): 1.544426; Kα2/Kα1 intensity ratio: 0.50 | Cu, kα, Kα1 (Å): 1.540598; Kα2 (Å): 1.544426; Kα2/Kα1 intensity ratio: 0.50 |
| X-ray light tube setting | 45 kV, 40 mA | 45 kV, 40 mA | 45 kV, 40 mA |
| Divergence slit | fixed 1/8° | fixed 1/8° | fixed 1/8° |
| Scanning mode | continuous | continuous | continuous |
| Scanning range(°2Theta) | 3-40 | 3-40 | 3-40 |
| Scanning time per step (s) | 17.8 | 33.0 | 46.7 |
| Scan step (°2Theta) | 0.0167 | 0.0167 | 0.0263 |
| Test time(min) | 5 | 10 | 5 |

2) Thermogravimetric Analysis (TGA) and Differential Scanning Calorimetry (DSC)

TGA and DSC curves were acquired on a TA Discovery TGA 5500 thermogravimetric analyzer and a TA Q2000/Discovery DSC 2500 differential scanning calorimeter, respectively using the test parameters listed in the table below.

TABLE 2 parameters of TGA and DSC

| Parameters | TGA | DSC |
|---|---|---|
| Method | Linear ramp-up | Linear ramp-up |
| Sample tray | Aluminum tray, open | Aluminum tray, glanded/unglanded |
| Temperature range | Room temperature-set endpoint temperature | Room temperature/25° C.-set endpoint temperature |
| Scanning rate(° C./min) | 10 | 10 |
| Protective gas | Nitrogen | Nitrogen |

3) Liquid-State NMR ($^1$H NMR)

The liquid NMR spectra were acquired on a Bruker 400M NMR instrument with DMSO-d6 as a solvent.

II. Specific Experimental Procedures and Results

1. Preparation and Characterization of Crystal Form A 5.00 g of the compound of formula (I) obtained in Example 1 was added to a three-neck flask, to which 100 mL of methanol was added, and was warmed up to 50-55° C. with stirring. The system became viscous, to which another 50 mL of methanol was added, and the stirring was continued for 5 h. The product was filtered and the filter cake was rinsed with 20 mL of methanol and dried under vacuum at 45° C. for 8 h, to finally afford 3.7 g of a crystal of the compound of formula (I), named as crystal form A.

The XRPD test results of the crystal form A are shown in FIG. 1, and the specific data are as follows.

TABLE 3

XRPD data of free base crystal form A

| Pos. [°2θ] | Height [cts] | FWHM Left [°2θ] | d-spacing [Å] | Rel. Int. [%] |
|---|---|---|---|---|
| 7.70 | 231.11 | 0.1535 | 11.48 | 9.32 |
| 8.67 | 2478.64 | 0.1279 | 10.20 | 100.00 |
| 11.53 | 321.20 | 0.1279 | 7.67 | 12.96 |
| 13.39 | 1541.20 | 0.1535 | 6.62 | 62.18 |
| 15.05 | 725.49 | 0.1535 | 5.89 | 29.27 |
| 15.47 | 196.40 | 0.1535 | 5.73 | 7.92 |
| 16.76 | 171.36 | 0.1535 | 5.29 | 6.91 |
| 17.38 | 706.55 | 0.1023 | 5.10 | 28.51 |
| 18.06 | 190.71 | 0.1535 | 4.91 | 7.69 |
| 19.34 | 134.29 | 0.2047 | 4.59 | 5.42 |
| 20.02 | 240.26 | 0.1023 | 4.44 | 9.69 |
| 21.24 | 1011.93 | 0.1535 | 4.18 | 40.83 |
| 21.63 | 268.58 | 0.2047 | 4.11 | 10.84 |
| 22.19 | 357.79 | 0.1023 | 4.01 | 14.43 |
| 22.86 | 702.79 | 0.1791 | 3.89 | 28.35 |
| 23.43 | 393.24 | 0.1279 | 3.80 | 15.87 |
| 24.89 | 717.43 | 0.2047 | 3.58 | 28.94 |
| 26.10 | 182.91 | 0.2558 | 3.41 | 7.38 |
| 26.44 | 229.98 | 0.1535 | 3.37 | 9.28 |
| 28.56 | 169.66 | 0.2558 | 3.13 | 6.84 |
| 28.94 | 235.38 | 0.2047 | 3.08 | 9.50 |
| 29.64 | 136.03 | 0.2047 | 3.01 | 5.49 |
| 32.78 | 67.79 | 0.1535 | 2.73 | 2.74 |

Figure 2:
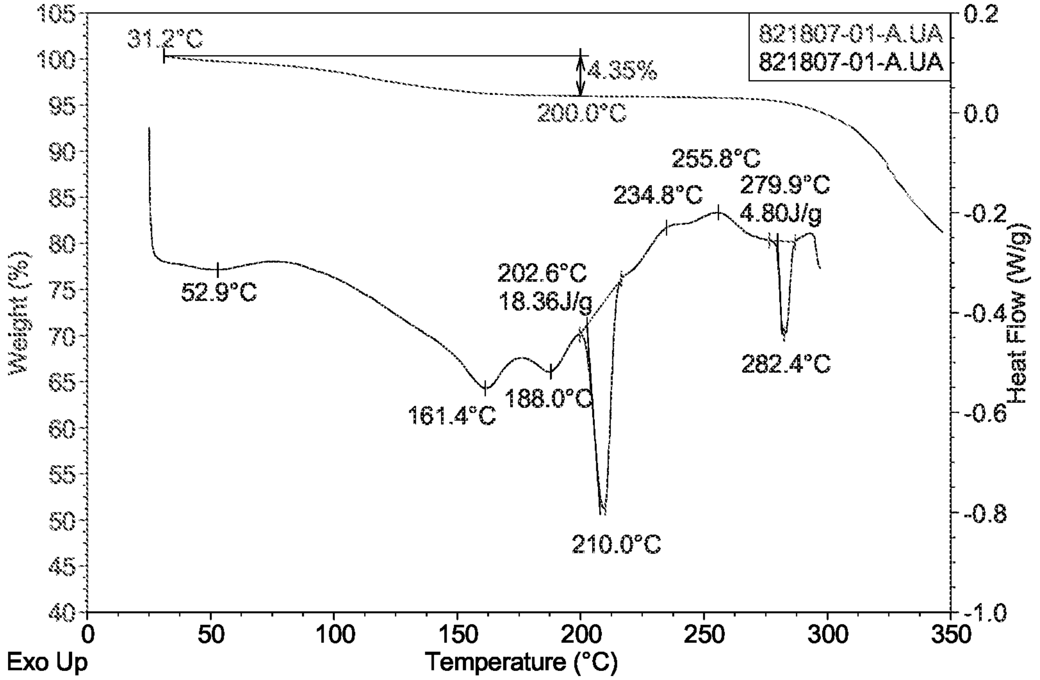
FIG. 2 illustrates TGA/DSC curves for crystal form A of compound of formula (I).

The TGA/DSC test results of the crystal form A are shown in FIG. 2, from which 4.4% weight loss from the crystal form A by heating to 200° C. could be seen, which is presumed to be caused by the removal of solvent or water from the sample, and multiple thermal signals could be observed in the range of 50-290° C.

No corresponding solvent MeOH residue is observed in $^1H$ NMR of the crystal from A, showing that the 4.4% weight loss in TGA is attributed to the removal of water, and indicating that the crystal from A may be a hydrate.

Figure 3:
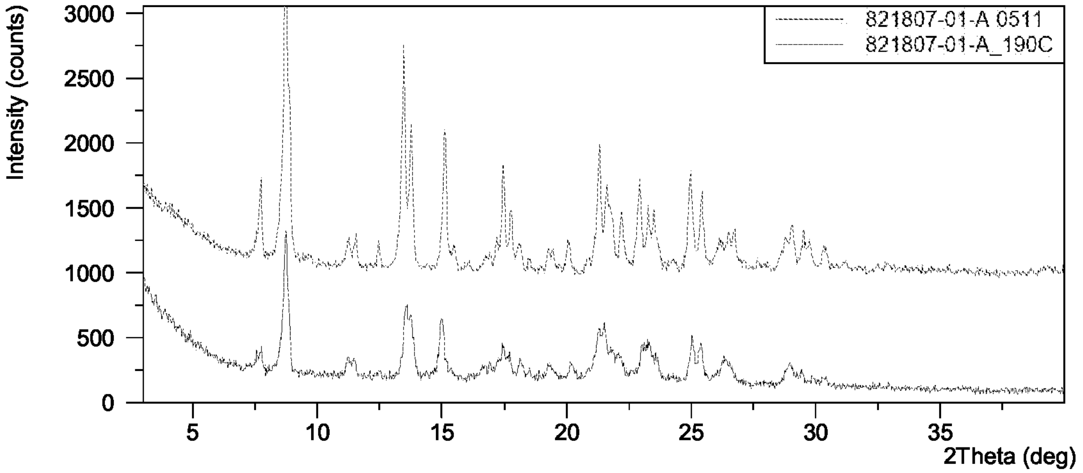
FIG. 3 illustrates a comparative diagram of XRPDs for crystal form A of compound of formula (I) before and after heating.

In order to investigate properties of the crystal from A, heating experiments were carried out on the crystal form A. After the crystal form A was heated to 190° C. and lowered to room temperature under nitrogen protection, the sample was taken out and exposed to air for XRPD. The test results are shown in FIG. 3, showing that crystal form of the sample remained unchanged, while a decrease in relative intensity of some diffraction peaks could be observed. Combined with the results of TGA/NMR, it is presumed that the change in crystallinity after heating was caused by the removal of water, and the crystal form A may be a hydrate.

Figure 4:
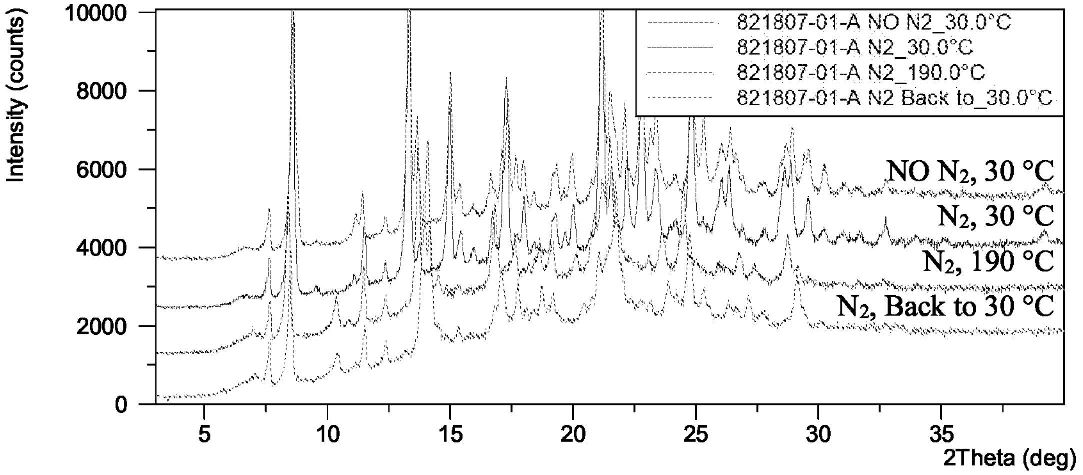
FIG. 4 illustrates a variable temperature XRPD diagram for crystal form A of compound of formula (I).

To further determine properties of the crystal form A, a variable temperature XRPD test was carried out on the crystal form A. The results are shown in FIG. 4, showing that after the sample was purged with nitrogen for 20 min at 30° C., its crystal form remained unchanged; and after the sample was heated to 190° C. and then cooled to 30° C. under nitrogen purging, an anhydrous crystal form D was obtained only under the protection of nitrogen (the shift of diffraction peaks at different temperatures may be related to lattice expansion caused by high temperature). Combined with the above TGA/DSC/NMR results of the crystal form A, it can be concluded that change of the crystal form A after heating to 190° C. is caused by the removal of water from the sample, and crystal form A is a hydrate.

2. Preparation and Characterization of Crystal Form B

The crystal form A was suspended and stirred in EtOH at room temperature for three days, and then centrifuged for isolation and the solid was dried under vacuum at room temperature for about two hours to give a crystal, named as crystal form B.

Figure 5:
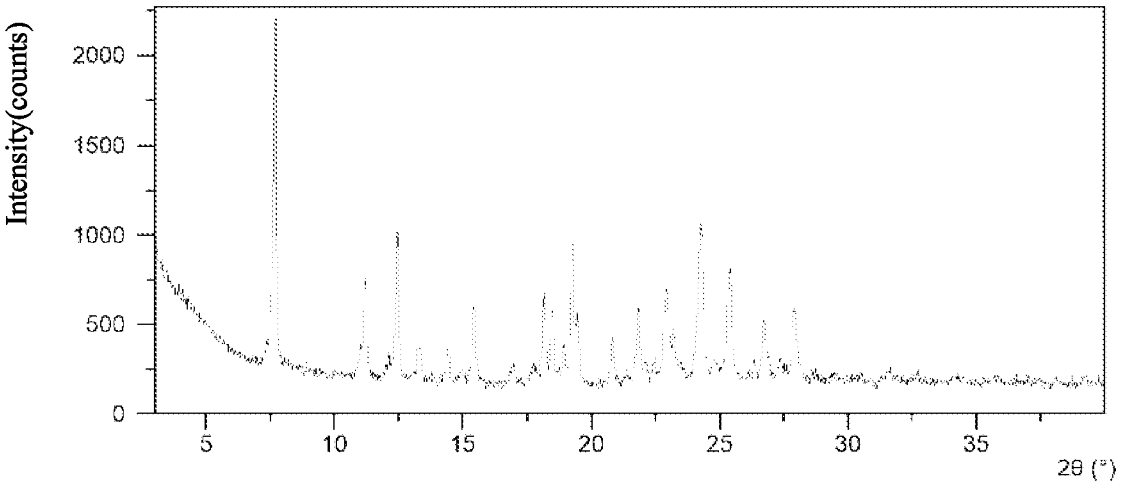
FIG. 5 illustrates an XRPD diagram for crystal form B of compound of formula (I).

The XRPD results of the crystal form B are shown in FIG. 5, and the specific data are as follows.

TABLE 4

XRPD data of free base crystal form B

| Pos. [°2θ] | Height [cts] | FWHM Left [°2θ] | d-spacing [Å] | Rel. Int. [%] |
|---|---|---|---|---|
| 7.70 | 1811.17 | 0.1279 | 11.48 | 100.00 |
| 11.20 | 536.39 | 0.1023 | 7.90 | 29.62 |
| 12.46 | 762.12 | 0.1023 | 7.11 | 42.08 |
| 13.29 | 173.38 | 0.1535 | 6.66 | 9.57 |
| 14.42 | 166.09 | 0.1279 | 6.14 | 9.17 |
| 14.95 | 63.15 | 0.1535 | 5.92 | 3.49 |
| 15.44 | 418.37 | 0.1535 | 5.74 | 23.10 |
| 16.96 | 108.45 | 0.1279 | 5.23 | 5.99 |
| 17.78 | 95.98 | 0.1535 | 4.99 | 5.30 |
| 18.17 | 492.76 | 0.1023 | 4.88 | 27.21 |
| 18.48 | 405.52 | 0.1279 | 4.80 | 22.39 |
| 18.93 | 225.59 | 0.1023 | 4.69 | 12.46 |
| 19.27 | 776.14 | 0.1023 | 4.61 | 42.85 |
| 19.50 | 334.26 | 0.1023 | 4.55 | 18.46 |
| 20.83 | 261.34 | 0.1023 | 4.26 | 14.43 |
| 21.84 | 414.04 | 0.1023 | 4.07 | 22.86 |
| 22.46 | 129.37 | 0.1023 | 3.96 | 7.14 |
| 22.94 | 565.17 | 0.1279 | 3.88 | 31.20 |
| 23.22 | 277.27 | 0.1279 | 3.83 | 15.31 |
| 24.29 | 870.32 | 0.1791 | 3.67 | 48.05 |
| 24.79 | 128.86 | 0.1535 | 3.59 | 7.11 |
| 25.40 | 612.31 | 0.1791 | 3.51 | 33.81 |
| 26.37 | 118.84 | 0.1023 | 3.38 | 6.56 |
| 26.74 | 333.95 | 0.1279 | 3.33 | 18.44 |
| 27.38 | 117.14 | 0.1535 | 3.26 | 6.47 |
| 27.92 | 389.74 | 0.1535 | 3.20 | 21.52 |
| 31.57 | 49.89 | 0.4093 | 2.83 | 2.75 |

TABLE 4-continued

XRPD data of free base crystal form B

| Pos. [°2θ] | Height [cts] | FWHM Left [°2θ] | d-spacing [Å] | Rel. Int. [%] |
|---|---|---|---|---|
| 32.64 | 35.47 | 0.3070 | 2.74 | 1.96 |
| 34.32 | 21.92 | 0.6140 | 2.61 | 1.21 |

Figure 6:
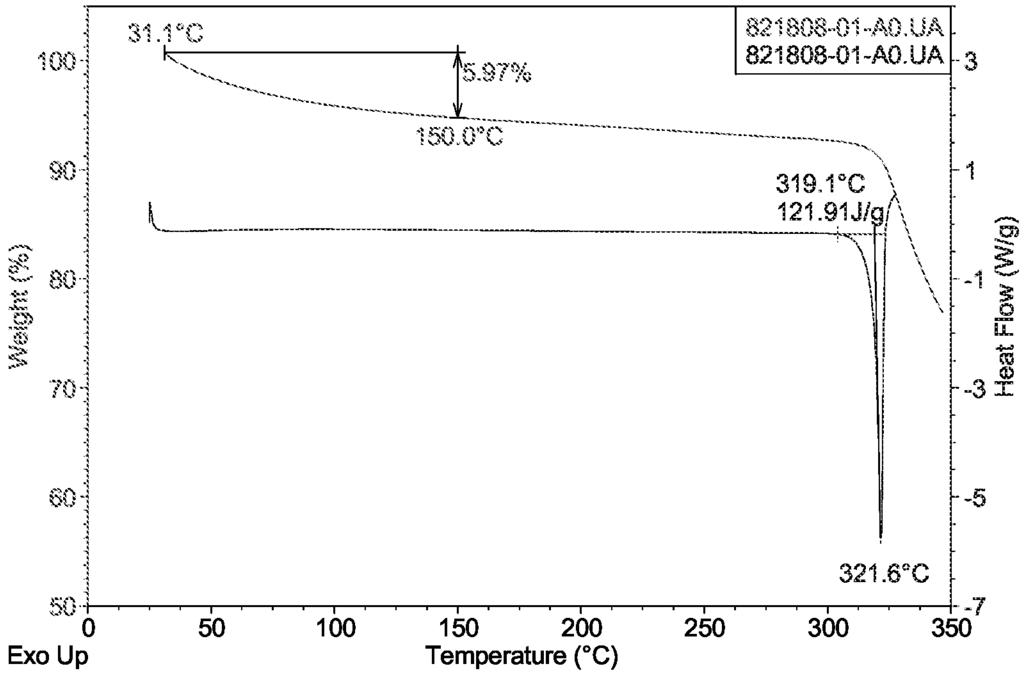
FIG. 6 illustrates TGA/DSC curves for crystal form B of compound of formula (I).

The TGA/DSC results of the crystal form B are shown in FIG. 6, from which 6.0% weight loss from the crystal form B by heating to 150° C. could be seen, which is presumed to be caused by the removal of solvent or water from the sample, and one heat absorption signal could be observed at 319.1° C. (onset temperature), which is presumed to come from melting of the sample.

$^1H$ NMR of the crystal form B shows that in the crystal form B, a molar ratio of EtOH to compound (I) is 0.12:1.00 (1.1 wt %).

Figure 7:
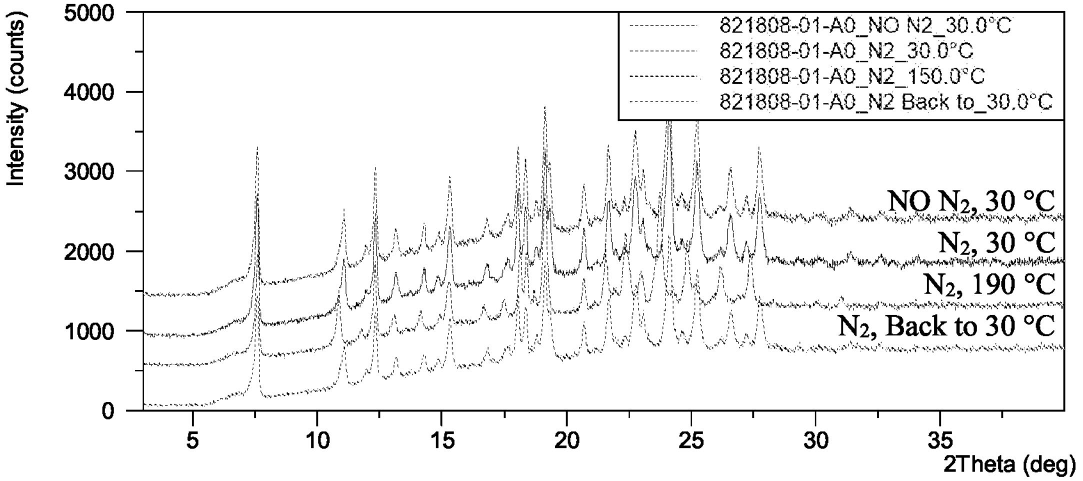
FIG. 7 illustrates a variable temperature XRPD diagram for crystal form B of compound of formula (I).

To investigate properties of the crystal form B, a variable temperature XRPD test was carried out on the crystal from B. The results are shown in FIG. 7. After the sample was purged under nitrogen for 20 min, the crystal form remained unchanged; when the sample was heated to 150° C. under nitrogen purging, the diffraction peaks were slightly shifted compared with those of original crystal form B, which is presumed to be related to lattice expansion at high temperature; after the sample was cooled back to 30° C., the positions of the diffraction peaks of the sample were the same as those of original crystal form B, and the diffraction peak shift disappeared. Combined with the TGA/DSC results, it is presumed that the TGA weight loss came from moisture or solvent residue on the sample surface, and the crystal form B is determined to be an anhydrous crystal form.

3. Preparation and Characterization of Crystal Form C

The hydrate crystal form A was suspended and stirred for three days at room temperature in acetone/$H_2O$ (v/v, 19:1) system containing L-ascorbic acid, and centrifuged for isolation. The solid was dried under vacuum at room temperature for about two hours to give a crystal, named as crystal form C.

Figure 8:
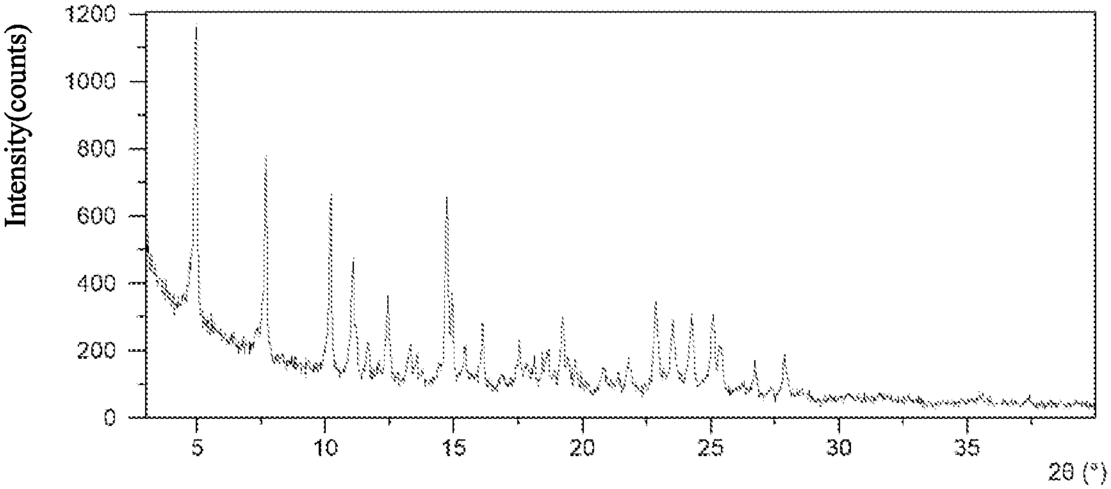
FIG. 8 illustrates an XRPD diagram for crystal form C of compound of formula (I).

The XRPD results for the crystal form C are shown in FIG. 8, with the following data.

TABLE 5

XRPD data of free base crystal form C

| Pos. [°2θ] | Height [cts] | FWHM Left [°2θ] | d-spacing [Å] | Rel. Int. [%] |
|---|---|---|---|---|
| 4.96 | 863.50 | 0.1023 | 17.82 | 100.00 |
| 7.66 | 443.56 | 0.1535 | 11.55 | 51.37 |
| 10.18 | 454.74 | 0.1535 | 8.69 | 52.66 |
| 11.07 | 286.10 | 0.2047 | 8.00 | 33.13 |
| 12.43 | 219.87 | 0.1279 | 7.12 | 25.46 |
| 13.28 | 92.21 | 0.1535 | 6.67 | 10.68 |
| 14.73 | 516.50 | 0.1023 | 6.01 | 59.81 |
| 15.42 | 103.56 | 0.1535 | 5.75 | 11.99 |
| 16.10 | 180.10 | 0.1535 | 5.50 | 20.86 |
| 17.54 | 107.03 | 0.1535 | 5.06 | 12.40 |
| 18.64 | 102.06 | 0.3070 | 4.76 | 11.82 |
| 19.24 | 204.00 | 0.1023 | 4.61 | 23.62 |
| 20.86 | 54.09 | 0.3070 | 4.26 | 6.26 |
| 21.82 | 78.62 | 0.1535 | 4.07 | 9.10 |
| 22.87 | 268.31 | 0.1791 | 3.89 | 31.07 |
| 23.52 | 217.75 | 0.1535 | 3.78 | 25.22 |
| 24.27 | 233.60 | 0.1279 | 3.67 | 27.05 |
| 25.09 | 232.35 | 0.1791 | 3.55 | 26.91 |
| 26.74 | 85.57 | 0.1535 | 3.33 | 9.91 |
| 27.88 | 118.37 | 0.2047 | 3.20 | 13.71 |

Figure 9:
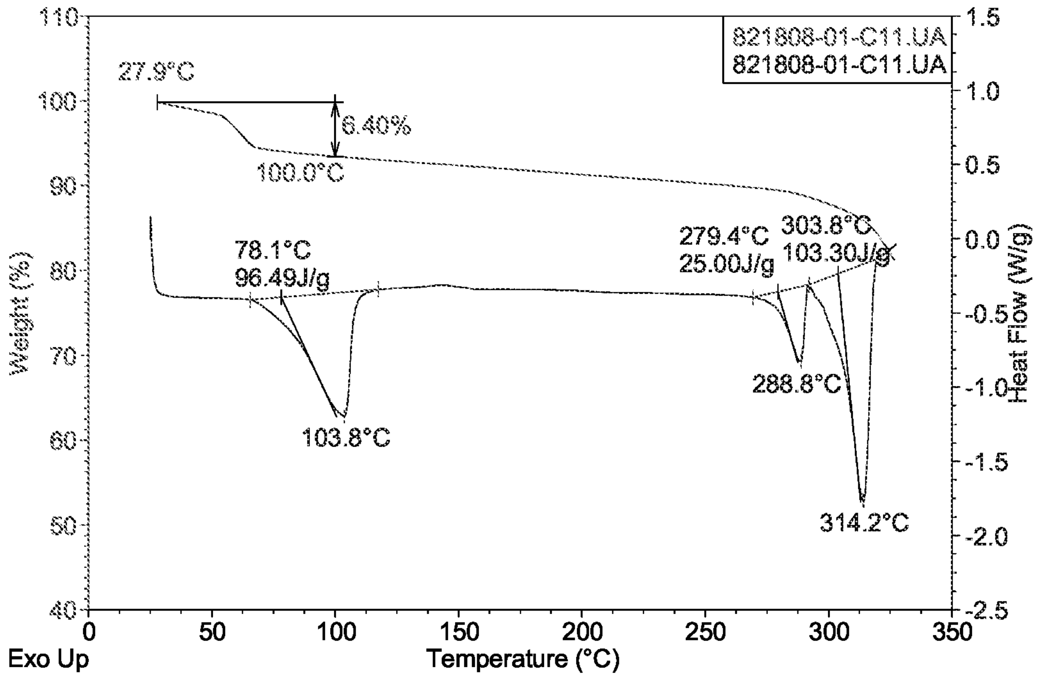
FIG. 9 illustrates TGA/DSC curves for crystal form C of compound of formula (I).

The TGA/DSC results of the crystal form C are shown in FIG. 9, from which it can be seen that, when the sample was heated to 100° C., it had a weight loss of 6.4%, and a thermal signal could be observed at 78.1° C. (onset temperature), which is presumed to come from removal of solvent or water from the sample; and some overlapped thermal signals could be observed at 279.4 and 303.8° C. (onset temperature).

$^1$H NMR data of crystal form C show that in the crystal form C, a molar ratio of acetone to compound (I) is 0.06:1.00 (0.7 wt %). Combined with the TGA results, it is speculated that the 6.4% weight loss in TGA is essentially from removal of water and thus the crystal form C might be a hydrate.

Figure 10:
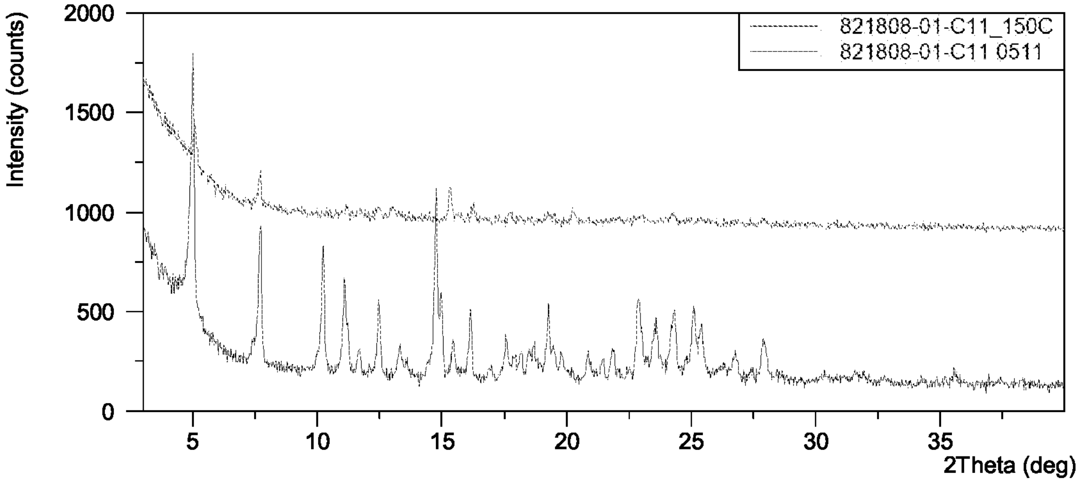
FIG. 10 illustrates a comparative diagram of XRPDs for crystal form C of compound of formula (I) before and after heating.

In order to investigate properties of the crystal form C, heating experiments were carried out on the crystal form C. After heating the crystal form C to 150° C. under nitrogen protection and cooling it back to room temperature, the sample was taken out and exposed to air for XRPD. The results are shown in FIG. 10, which show that crystallinity of the sample decreased significantly after heating. Combined with the NMR and TGA results, it is speculated that the decrease in crystallinity after heating was caused by the removal of water, and the crystal form C is determined to be a hydrate.

4. Preparation and Characterization of Crystal Form D

Figure 11:
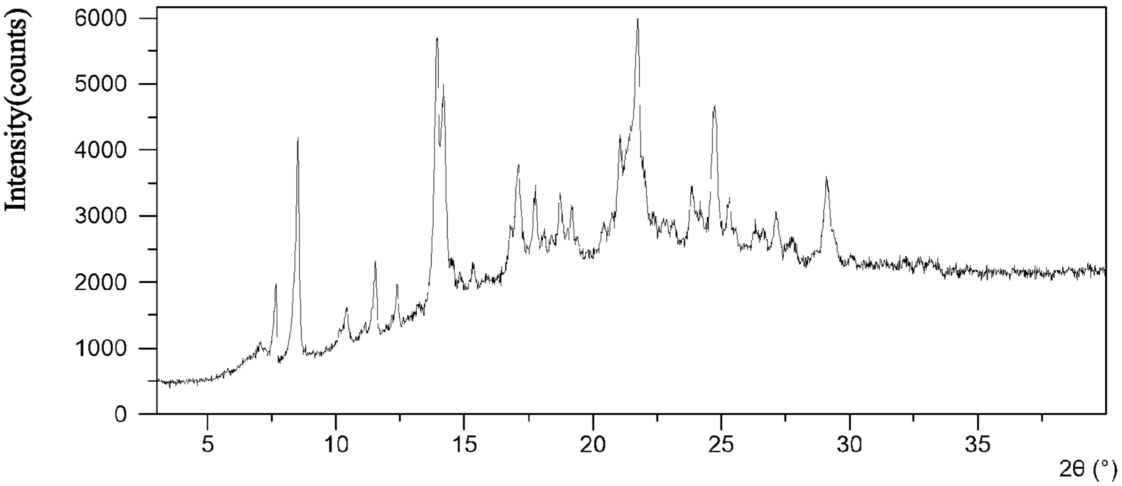
FIG. 11 illustrates an XRPD diagram for crystal form D of compound of formula (I).

Crystal form D was obtained by heating the crystal form A to 190° C. and lowering the temperature to 30° C. under nitrogen protection, and the XRPD results are shown in FIG. 11.

Figure 12:
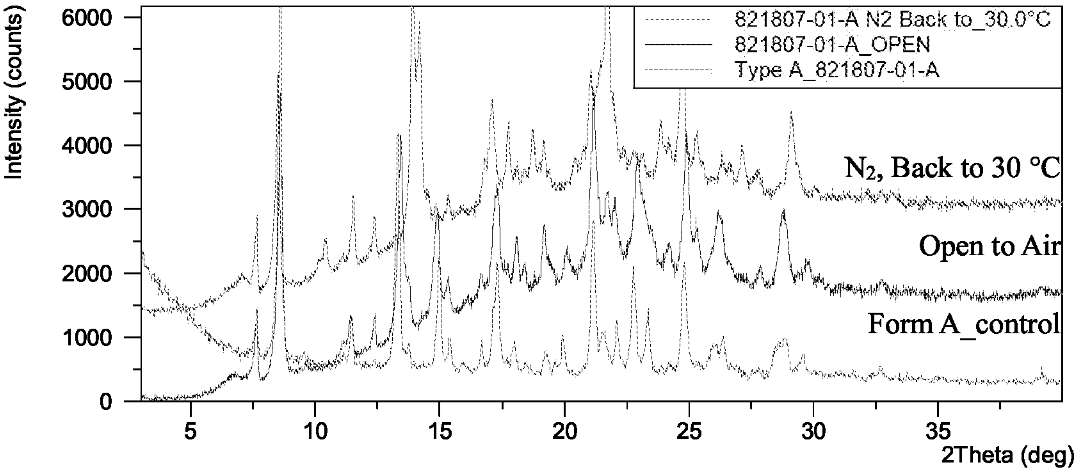
FIG. 12 illustrates a comparative diagram of XRPDs for crystal form D of compound of formula (I).

The crystal form D was exposed to air for about 2 hours and then was subjected to XRPD. The results in FIG. 12 show that the crystal form D transformed into the crystal form A. It is assumed that the crystal form D could only exist under nitrogen protection and would rapidly absorb water from the environment and transform into the crystal form A when it is exposed to air. No further studies are conducted because of instability of the crystal form D.

5. Preparation and Characterization of Crystal Form E

The hydrate crystal form A was suspended and stirred in EtOH at 50° C. for one day, then centrifuged for isolation. The solid was allowed to stand at room temperature and dried overnight in air, thereby giving a crystal, named as crystal form E.

Figure 13:
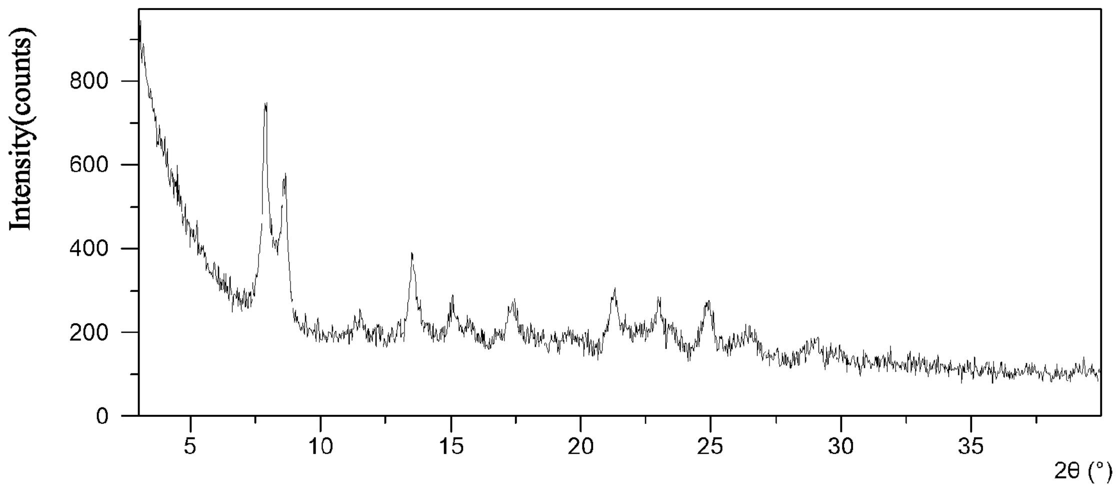
FIG. 13 illustrates an XRPD diagram for crystal form E of compound of formula (I).

The XRPD results of the crystal form E are shown in FIG. 13, and the specific data are as follows.

TABLE 6

XRPD data of free base crystal form E

| Pos. [°2θ] | Height [cts] | FWHM Left [°2θ] | d-spacing [Å] | Rel. Int. [%] |
|---|---|---|---|---|
| 7.89 | 480.69 | 0.1279 | 11.21 | 100.00 |
| 8.62 | 304.79 | 0.1535 | 10.25 | 63.41 |
| 11.42 | 31.32 | 0.6140 | 7.75 | 6.52 |
| 13.54 | 193.16 | 0.2047 | 6.54 | 40.18 |
| 15.10 | 79.05 | 0.3070 | 5.87 | 16.45 |
| 17.40 | 78.19 | 0.3582 | 5.10 | 16.27 |
| 21.27 | 131.10 | 0.2047 | 4.18 | 27.27 |
| 23.02 | 88.62 | 0.6140 | 3.86 | 18.44 |
| 24.87 | 114.93 | 0.4093 | 3.58 | 23.91 |
| 26.48 | 52.95 | 0.6140 | 3.37 | 11.02 |
| 28.86 | 33.53 | 0.6140 | 3.09 | 6.97 |

Figure 14:
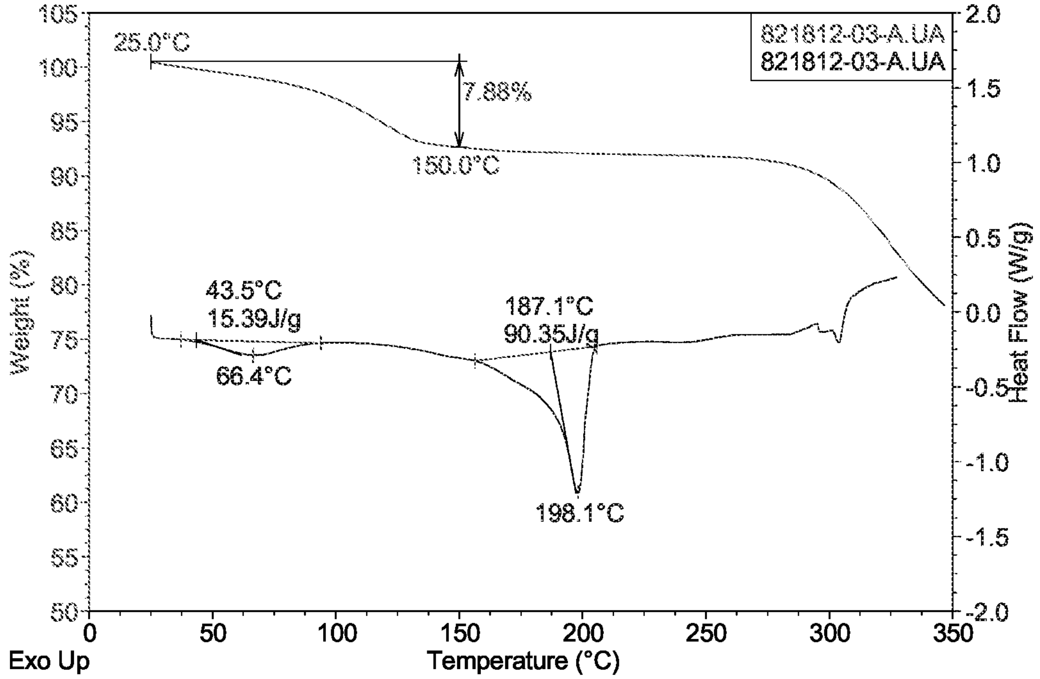
FIG. 14 illustrates TGA/DSC curves for crystal form E of compound of formula (I).

The TGA/DSC results of the crystal form E are shown in FIG. 14, from which it can be seen that when the sample was heated to 150° C., it had a weight loss of 7.9% and a thermal signal could be observed at 43.5° C. (onset temperature), which is presumed to come from the removal of solvent or water from the sample; and that a heat absorption signal could be observed at 187.1° C. (onset temperature).

The $^1$H NMR data of the crystal form E show that a molar ratio of EtOH to compound (I) is 0.62:1.00 (5.7 wt %). Combined with the TGA results, it is presumed that the weight loss in TGA came from the removal of EtOH and water.

Figure 15:
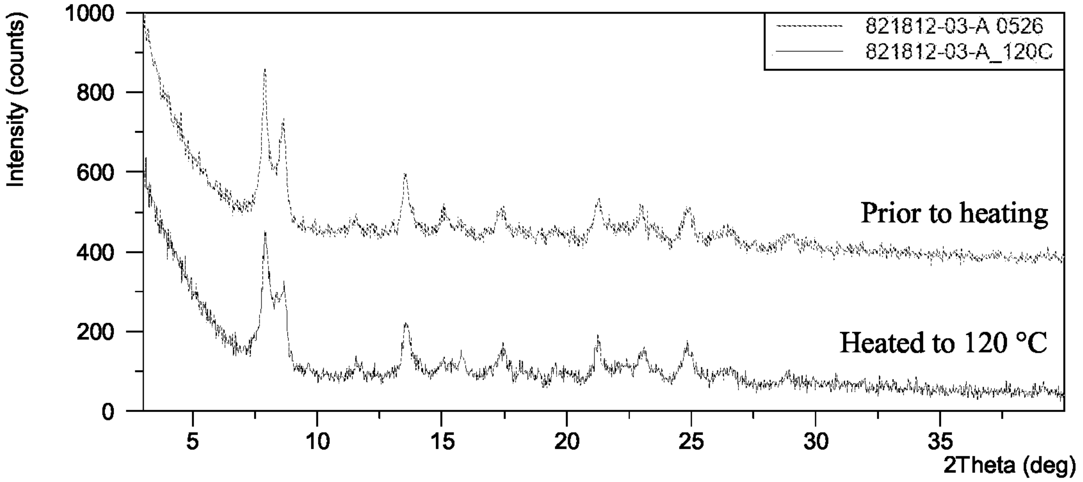
FIG. 15 illustrates a comparative diagram of XRPDs for crystal form E of compound of formula (I) before and after heating.

In order to investigate properties of the crystal form E, heating experiments were carried out on the crystal form E. After the crystal form E was heated to 120° C. under nitrogen protection and lowered to room temperature, the sample was taken out and exposed to air for XRPD. The results are shown in FIG. 15, which show that crystal form of the sample remained unchanged. The NMR results show that a molar ratio of EtOH to compound (I) in the sample after heating is 0.65:1.00 (5.7 wt %).

Figure 16:
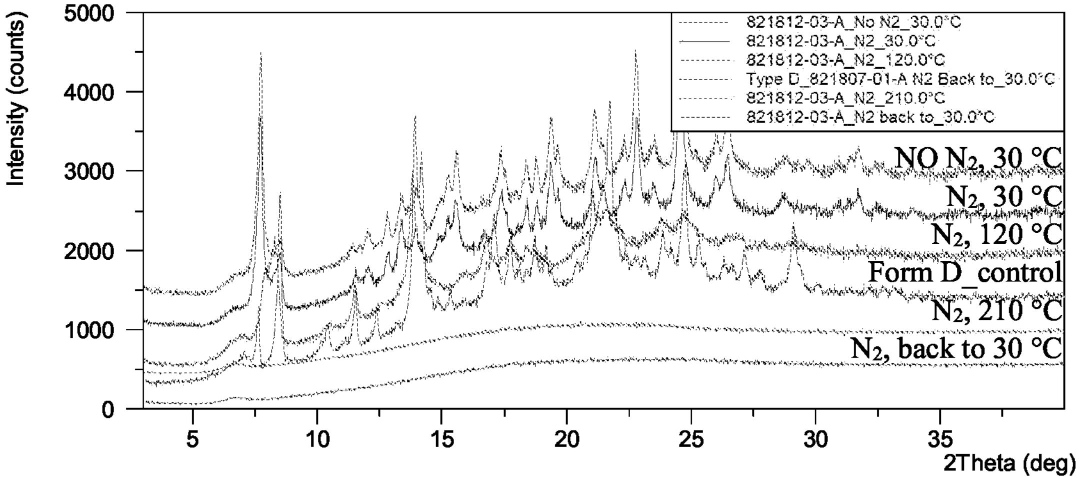
FIG. 16 illustrates a variable temperature XRPD diagram for crystal form E of compound of formula (I).

To further investigate properties of the crystal form E, a variable temperature XRPD test was carried out on the crystal form E. The results are shown in FIG. 16, from which it can be seen that when the sample was purged under nitrogen for 20 min, crystal form of the sample remained unchanged; when the sample was heated to 120° C. under nitrogen purging, the sample had transformed into an anhydrous crystal form D which could only exist under the protection of nitrogen (the positions of a few diffraction peaks are shifted compared with the crystal form D, which might be related to different degrees of expansion of each lattice at different temperatures, wherein the XRPD pattern of the control crystal form D was measured at 30° C.); when the sample was continued to be heated to 210° C., the sample had transformed into an amorphous form; when the sample was lowered to 30° C., the sample was still amorphous and was observed to become gelatinous, and it is presumed that the sample had melted. Compared with the result in which when the crystal form E was heated to 120° C. and exposed to air, the crystal form remained unchanged, the result of the experiment in which the sample was heated to 120° C. under nitrogen purging was different. It is speculated that the difference between these two heating results is related to whether the sample was exposed to air after heating. That is, an anhydrous crystal form D could quickly adsorb water in the environment and turn into a crystal form E after being exposed to air and heated, and thus it is speculated that water molecules are involved in the lattice composition of crystal form E.

6. Preparation and Characterization of Crystal Form F

The hydrate crystal form A and the anhydrous crystal form B, used as the crystal seeds, were suspended and stirred in acetone at 50° C. for one day, then centrifuged for insolation. The solid was allowed to stand in air at room temperature overnight, giving a crystal, named as crystal form F.

Figure 17:
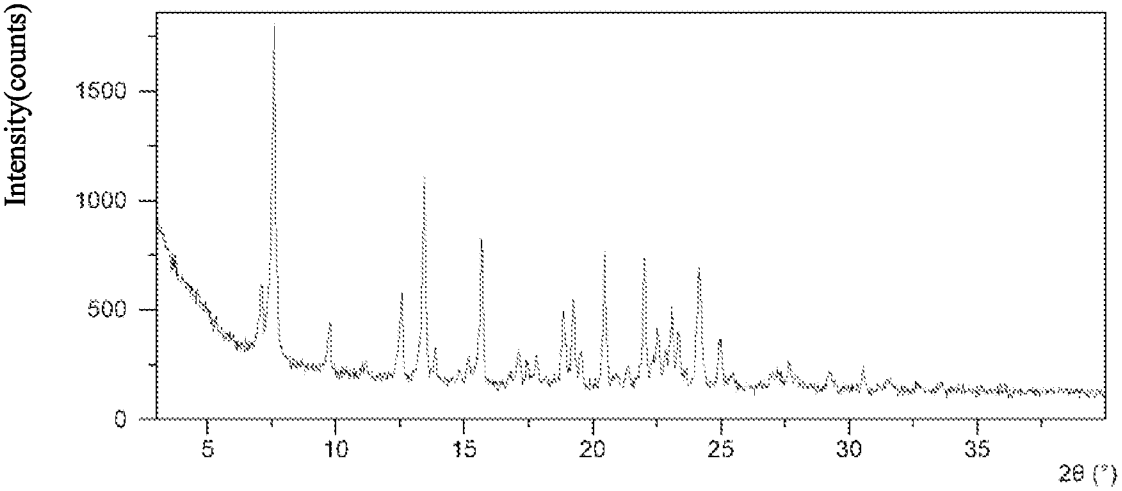
FIG. 17 illustrates an XRPD diagram for crystal form F of compound of formula (I).

The XRPD results of the crystal form F are shown in FIG. 17, and the specific data are as follows.

TABLE 7

XRPD data of free base crystal form F

| Pos. [°2θ] | Height [cts] | FWHM Left [°2θ] | d-spacing [Å] | Rel. Int. [%] |
|---|---|---|---|---|
| 7.09 | 307.77 | 0.1023 | 12.47 | 20.28 |
| 7.59 | 1517.86 | 0.1023 | 11.65 | 100.00 |
| 9.75 | 203.19 | 0.1023 | 9.07 | 13.39 |
| 12.55 | 375.34 | 0.1023 | 7.05 | 24.73 |
| 13.44 | 928.11 | 0.1279 | 6.59 | 61.15 |
| 13.87 | 148.21 | 0.1279 | 6.38 | 9.76 |

TABLE 7-continued

| XRPD data of free base crystal form F | | | | |
|---|---|---|---|---|
| Pos. [°2θ] | Height [cts] | FWHM Left [°2θ] | d-spacing [Å] | Rel. Int. [%] |
| 15.18 | 110.10 | 0.1535 | 5.84 | 7.25 |
| 15.67 | 655.40 | 0.1023 | 5.65 | 43.18 |
| 17.12 | 157.39 | 0.1023 | 5.18 | 10.37 |
| 17.83 | 131.61 | 0.1023 | 4.98 | 8.67 |
| 18.87 | 351.05 | 0.1535 | 4.70 | 23.13 |
| 19.26 | 388.28 | 0.1023 | 4.61 | 25.58 |
| 19.53 | 147.45 | 0.1023 | 4.55 | 9.71 |
| 20.47 | 598.82 | 0.1279 | 4.34 | 39.45 |
| 21.38 | 91.65 | 0.1535 | 4.16 | 6.04 |
| 22.02 | 588.87 | 0.1279 | 4.04 | 38.80 |
| 22.54 | 252.16 | 0.1279 | 3.94 | 16.61 |
| 23.09 | 338.36 | 0.1023 | 3.85 | 22.29 |
| 23.36 | 251.34 | 0.1279 | 3.81 | 16.56 |
| 24.16 | 549.29 | 0.1791 | 3.68 | 36.19 |
| 24.97 | 209.03 | 0.1535 | 3.57 | 13.77 |
| 27.12 | 61.16 | 0.3070 | 3.29 | 4.03 |
| 27.66 | 120.71 | 0.1023 | 3.23 | 7.95 |
| 29.24 | 85.23 | 0.1535 | 3.05 | 5.62 |
| 30.54 | 103.20 | 0.1023 | 2.93 | 6.80 |
| 31.56 | 41.63 | 0.4093 | 2.83 | 2.74 |

Figure 18:
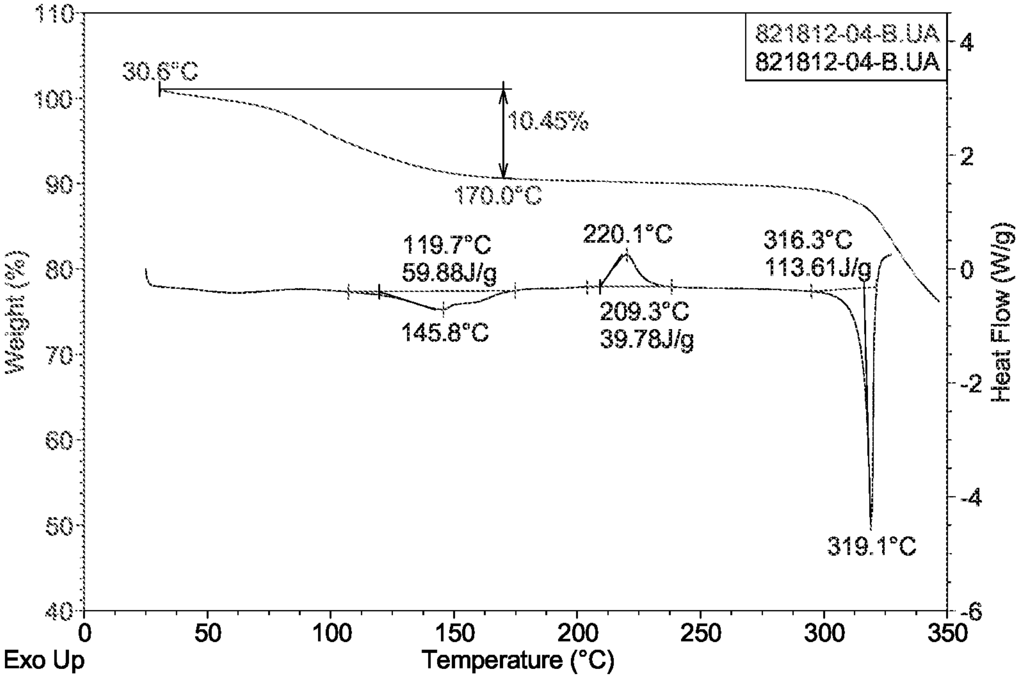
FIG. 18 illustrates TGA/DSC curves for crystal form F of compound of formula (I).

The TGA/DSC results of the crystal form F (FIG. 18) show that when the sample was heated to 170° C., it had a weight loss of 10.5%, and a thermal signal was observed at 119.7° C. (onset temperature), which is presumed to come from the removal of solvent or water from the sample; and that two thermal signals are observed at 209.3 and 316.3° C. (onset temperature). The $^{1}$H NMR data of the crystal form F show that a molar ratio of acetone to compound (I) in crystal form F is 0.68:1.00 (7.7 wt %). Combined with the TGA results, it is assumed that most of the weight loss in TGA came from the removal of acetone.

Figure 19:
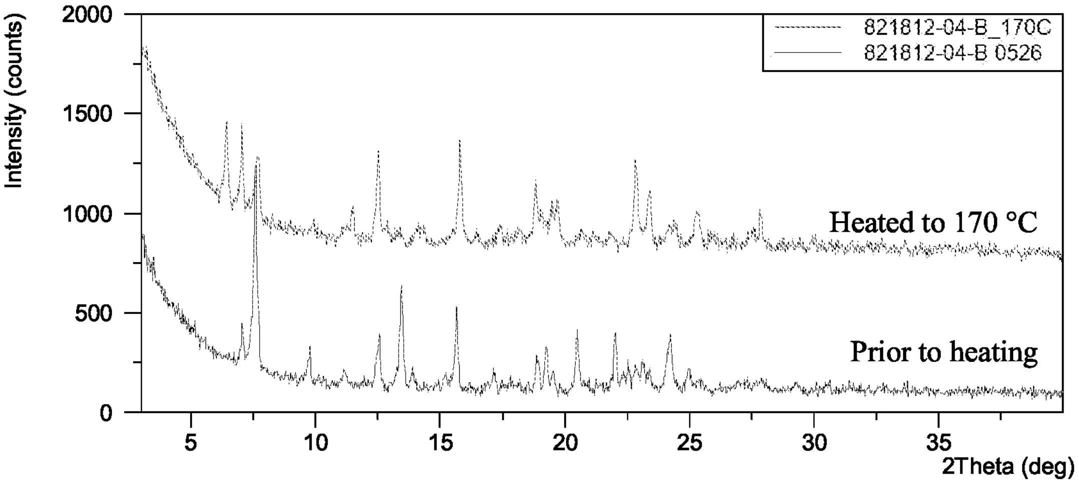
FIG. 19 illustrates a comparative diagram of XRPDs for crystal form F of compound of formula (I) before and after heating.

In order to investigate properties of the crystal form F and to study possible source of the thermal signals in DSC, heating experiments were carried out on crystal form F. After heating the crystal form F to 170° C. under nitrogen protection and lowering it to room temperature, the sample was taken out and exposed to air for XRPD. The results (FIG. 19) show that the sample was converted to hydrate crystal form G. The NMR results show that no significant acetone residues could be observed in the heated sample. Combined with the results before and after heating, the change of the crystal form observed in XRPD, and that the component removed after heating was mainly acetone as shown by TGA/NMR, it is concluded that the conversion of the crystal form F to crystal form G after heating may be caused by the removal of acetone, and that the crystal form F is determined to be probably an acetone solvate.

7. Preparation and Characterization of Crystal Form G

The acetone solvate crystal form F was heated to 170° C. under nitrogen protection and lowered to room temperature, and then the sample was taken out and exposed to air to obtain a crystal, named as crystal form G.

Figure 20:
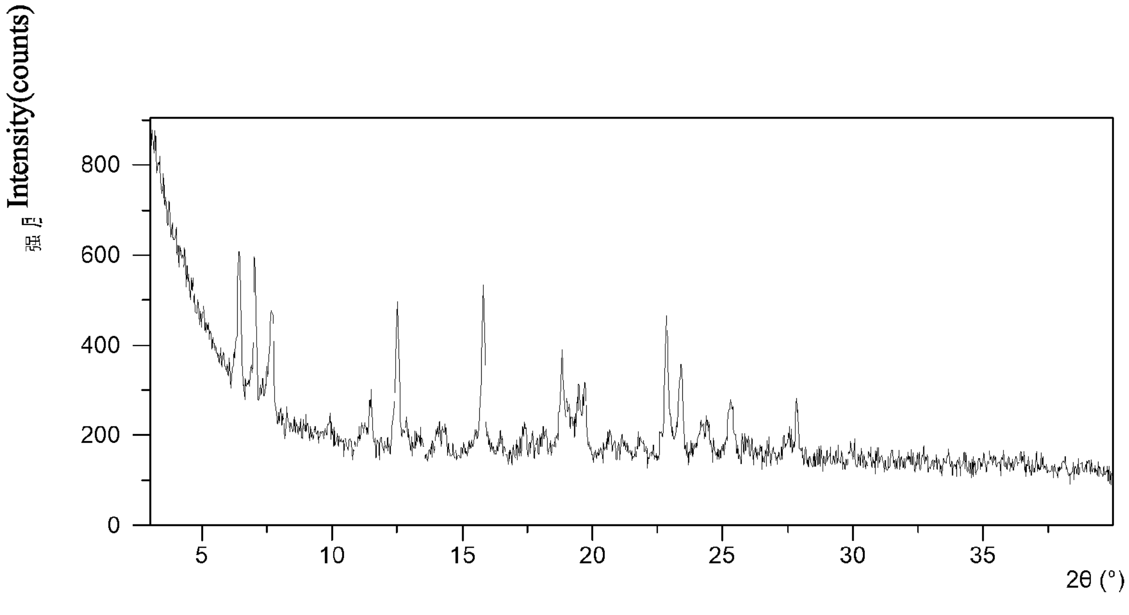
FIG. 20 illustrates an XRPD diagram for crystal form G of compound of formula (I).

The XRPD results of the crystal form G are shown in FIG. 20, and the specific data are as follows.

TABLE 8

| XRPD data of free base crystal form G | | | | |
|---|---|---|---|---|
| Pos. [°2θ] | Height [cts] | FWHM Left [°2θ] | d-spacing [Å] | Rel. Int. [%] |
| 6.42 | 255.58 | 0.1535 | 13.77 | 69.78 |
| 7.04 | 285.52 | 0.1023 | 12.55 | 77.95 |
| 7.69 | 209.14 | 0.1535 | 11.50 | 57.10 |
| 11.48 | 112.32 | 0.1023 | 7.71 | 30.67 |
| 12.52 | 300.94 | 0.1279 | 7.07 | 82.16 |
| 14.19 | 40.94 | 0.5117 | 6.24 | 11.18 |
| 15.81 | 366.28 | 0.1023 | 5.61 | 100.00 |
| 17.42 | 47.96 | 0.3070 | 5.09 | 13.09 |
| 18.83 | 220.00 | 0.1023 | 4.71 | 60.06 |
| 19.58 | 111.35 | 0.3070 | 4.53 | 30.40 |
| 22.85 | 294.49 | 0.1279 | 3.89 | 80.40 |
| 23.40 | 204.33 | 0.1535 | 3.80 | 55.79 |
| 24.30 | 62.63 | 0.5117 | 3.66 | 17.10 |
| 25.31 | 119.65 | 0.2047 | 3.52 | 32.67 |
| 27.85 | 114.33 | 0.1279 | 3.20 | 31.21 |

Figure 21:
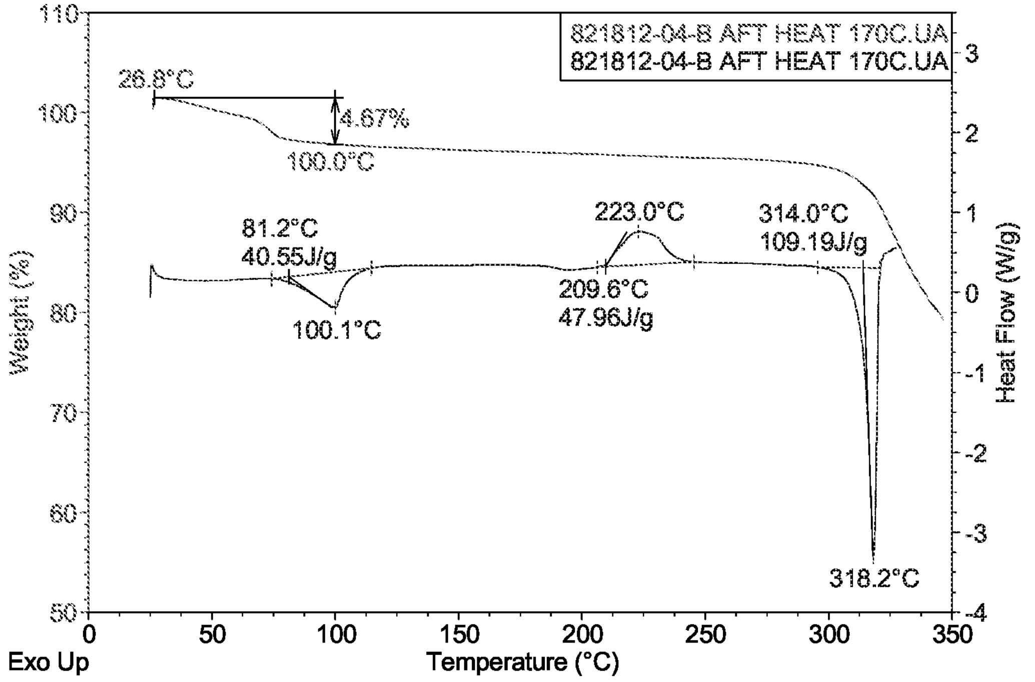
FIG. 21 illustrates TGA/DSC curves for crystal form G of compound of formula (I).

The TGA/DSC results of the crystal form G (FIG. 21) show that when the crystal form G was heated to 100° C., it had a weight loss of 4.7% and one thermal signal could be observed at 81.2° C. (onset temperature), which is presumed to come from the removal of solvent or water from the sample; and that two thermal signals could be observed at 209.6 and 314.0° C. (onset temperature). The NMR results of the crystal form G show that no significant acetone residue could be observed in the sample, and thus the crystal form G may be a hydrate or an anhydrous crystal form.

Figure 22:
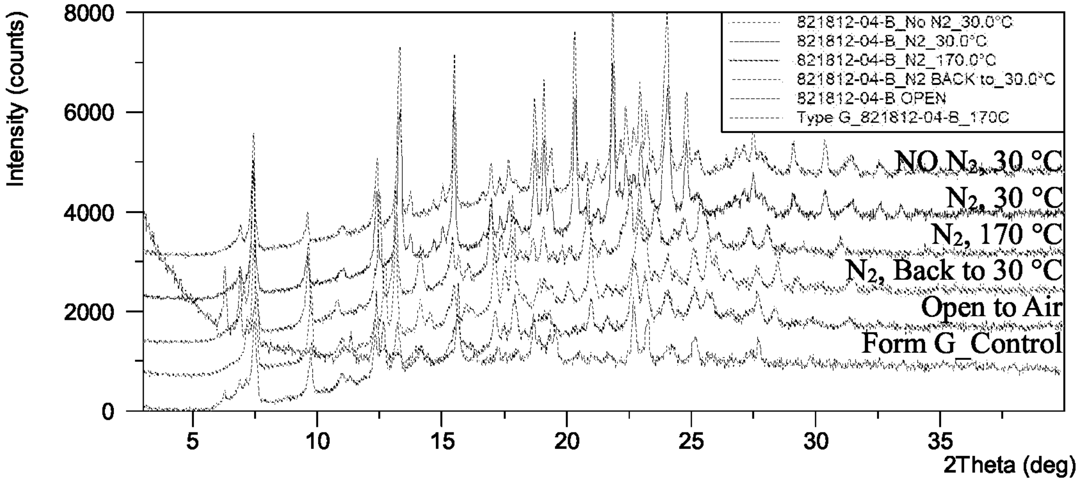
FIG. 22 illustrates a variable temperature XRPD pattern for crystal form G of compound of formula (I).

A further study on the crystal form G was carried out by a variable temperature XRPD in which the crystal form F was used as a starting material. The results of FIG. 22 show that when the crystal form F was purged under nitrogen for 20 min, the crystal form remained unchanged; when the crystal form F was heated to 170° C. under nitrogen purging, it transformed into an anhydrous crystal form J that existed only under nitrogen protection; and when it was cooled down to 30° C. and exposed to air with the lid open to test XRPD, the results show that it transformed into the crystal form G. It is assumed that the crystal form J would absorb moisture from the environment after it is exposed to air and change to the crystal form G, and that the crystal form G is a hydrate.

8. Preparation and Characterization of Crystal Form J

Figure 23:
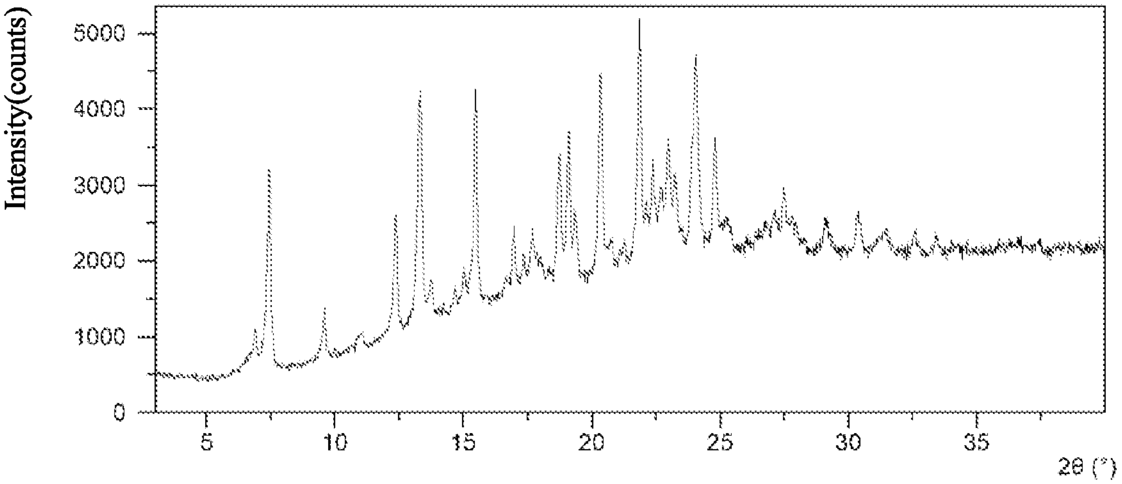
FIG. 23 illustrates an XRPD diagram for crystal form J of compound of formula (I).

A crystal form was obtained by heating the acetone solvate compound crystal form F to 170° C. under nitrogen protection and lowering it to 30° C., named as crystal form J. The XRPD results of the crystal form J are shown in FIG. 23.

Figure 24:
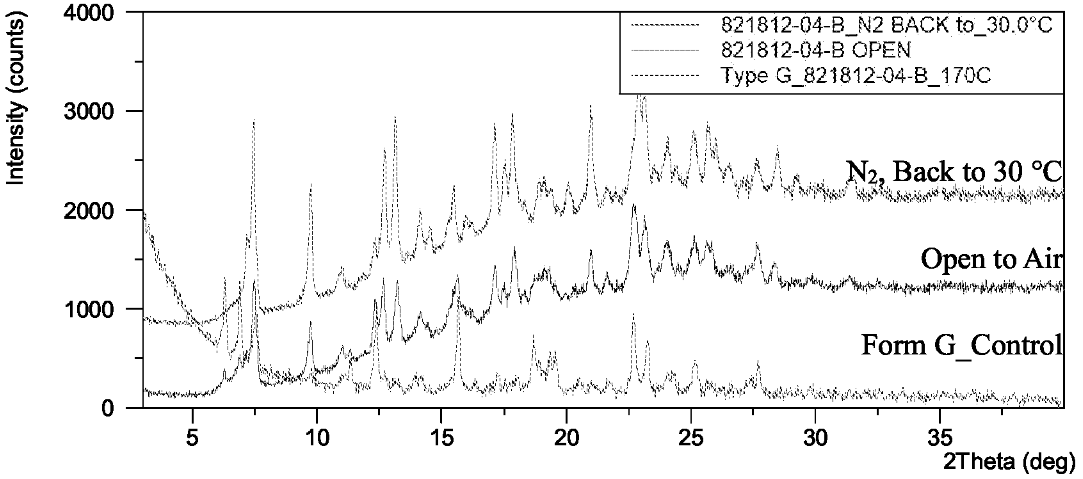
FIG. 24 illustrates a comparative diagram of XRPDs for crystal form J of compound of formula (I).

The XRPD of the crystal from J was tested again after it was exposed to air, and the results (FIG. 24) show that it transformed into the hydrate crystal form G. It is assumed that the crystal form J could only exist under nitrogen protection, and it would rapidly absorb moisture from the environment to shift into the crystal form G when it was exposure to air. Further studies were not carried out because of the instability of the crystal form J.

9. Preparation and Characterization of Crystal Form H

Figure 25:
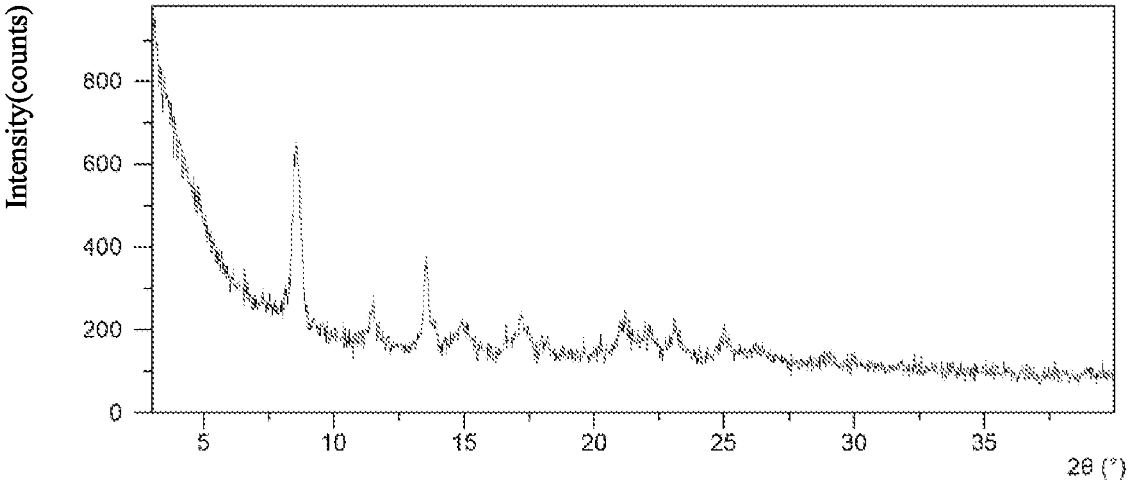
FIG. 25 illustrates an XRPD diagram for crystal form H of compound of formula (I).

The crystal form E was heated to 150° C. under nitrogen protection and lowered to room temperature, then the sample was taken out and exposed to air to give a crystal, named as crystal form H. The XRPD results are shown in FIG. 25.

10. Preparation and Characterization of Crystal Form I

Figure 26:
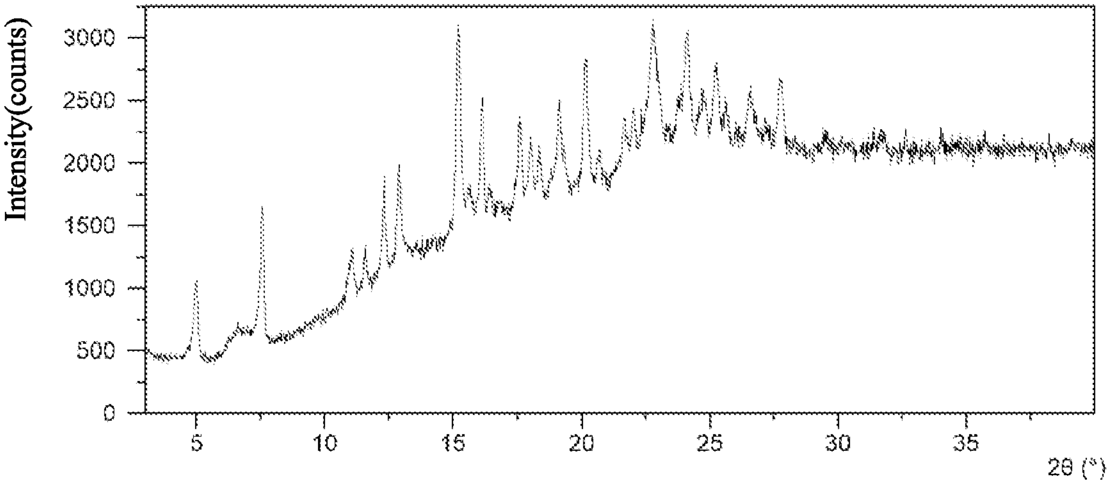
FIG. 26 illustrates an XRPD diagram for crystal form I of compound of formula (I).

The hydrate crystal form C was heated to 150° C. under nitrogen protection and lowered to room temperature by a variable temperature XRPD to give a crystal, named as crystal form I. The XRPD results are shown in FIG. 26.

Example 5: Study of Salts of the Compound of Formula (I)

The compound of formula (I) obtained in Example 1 was used as a starting material, different acids were selected for the study of salt forms, crystallization was carried out under different conditions to study polymorphism phenomenon of each salt, and the various crystal forms were characterized and identified by X-ray powder diffraction (XRPD), thermogravimetric analysis (TGA), differential scanning calorimetry (DSC), nuclear magnetic resonance hydrogen spectroscopy ($^1H$ NMR), high performance liquid chromatography/ion chromatography (HPLC/IC) in order to provide a basis for the production and formulation of pharmaceutical preparations.

I. Main Reagents, Instruments and Measurement Methods Used in the Study

1. The Names and Abbreviations of the Main Solvents Used in the Experiments are Shown in the Table Below.

TABLE 9

Names and abbreviations of the solvents used in the tests

| Abbreviation | Name | Abbreviation | Name |
|---|---|---|---|
| MeOH | Methanol | MTBE | Methyl tert-butyl ether |
| EtOH | Ethanol | Anisole | Methyl anisole |
| IPA | Isopropyl alcohol | n-Heptane | n-Heptane |
| Acetone | Acetone | Toluene | Toluene |
| MIBK | Methyl isobutyl ketone | DCM | Dichloromethane |
| EtOAc | Ethyl acetate | ACN | Acetonitrile |
| IPAc | Isopropyl acetate | DMSO | Dimethyl sulfoxide |
| THF | Tetrahydrofuran | $CHCl_3$ | Chloroform |
| 2-MeTHF | 2-Methyltetrahydrofuran | DMF | N,N-dimethylformamide |
| 1,4-Dioxane | 1,4-Dioxane | $H_2O$ | Water |

2. X-Ray Powder Diffraction (XRPD)

XRPD patterns were collected on a PANalytical X-ray powder diffraction analyzer, and the scanning parameters are shown in the table below.

TABLE 10 parameters of XRPD

| Parameter | XRPD (reflection mode) | XRPD (reflection mode) |
|---|---|---|
| Model | Empyrean | X'Pert³ |
| X-Ray | Cu, kα, Kα1 (Å): 1.540598; Kα2 (Å): 1.544426; Kα2/Kα1 intensity ratio: 0.50 | Cu, kα, Kα1 (Å): 1.540598; Kα2 (Å): 1.544426; Kα2/Kα1 intensity ratio: 0.50 |
| X-ray light tube setting | 45 kV, 40 mA | 45 kV, 40 mA |
| Divergence slit | fixed 1/8° | fixed 1/8° |
| Scanning mode | continuous | continuous |
| Scanning range(°2Theta) | 3-40 | 3-40 |
| Scanning time per step (s) | 17.8 | 46.7 |
| Scan step (°2Theta) | 0.0167 | 0.0263 |
| Test time (min) | 5 | 5 |

3. Thermogravimetric Analysis (TGA) and Differential Scanning Calorimetry (DSC)

TGA and DSC curves were acquired on a TA Q5000/Discovery TGA 5500 thermogravimetric analyzer and a TA Discovery DSC 2500 differential scanning calorimeter, respectively, and the test parameters are listed in the table below.

TABLE 11

Parameters of TGA and DSC

| Parameters | TGA | DSC |
|---|---|---|
| Method | Linear ramp-up | Linear ramp-up |
| Sample tray | Aluminum tray, open | Aluminum tray, glanded/unglanded |
| Temperature range | Room temperature-set endpoint temperature | Room temperature/25° C.-set endpoint temperature |
| Scanning rate (° C./min) | 10 | 10 |
| Protective gas | Nitrogen | Nitrogen |

4. Dynamic Moisture Sorption (DVS)

Dynamic moisture sorption (DVS) curves were collected on the DVS Intrinsic from SMS (Surface Measurement Systems). The relative humidity at 25° C. was calibrated with deliquescence points of LiCl, $Mg(NO_3)_2$ and KCl. Parameters for the DVS test are listed in Table 12.

TABLE 12

Parameters of DVS

| Parameters | Settings |
|---|---|
| Temperature | 25° C. |
| Sample volume | 10-20 mg |
| Protective gas and flow rate | $N_2$, 200 mL/min |
| dm/dt | 0.002%/min |
| Min. dm/dt equilibrium time | 10 min |
| Max. equilibrium time | 180 min |
| RH range | 0% RH-95% RH-0% RH |
| RH gradient | 10% (0% RH-90% RH, 90% RH-0% RH)<br>5% (90% RH-95% RH, 95% RH-90% RH) |

5. Liquid-State NMR ($^1H$ NMR)

The liquid NMR spectra were acquired on a Bruker 400M NMR instrument with DMSO-d6 as a solvent.

6. pH Meter (pH)

The pH was collected by Sartorius PB-10 PH meter.

7. High Performance Liquid Chromatography (HPLC) and Ion Chromatography (IC)

The sample purity and solubility were obtained by HPLC, and the molar ratio of salt-based samples of inorganic acid systems were obtained by HPLC and ion chromatography, with HPLC being collected on an Agilent 1290 HPL and ion chromatography being collected on a Thermo ICS1100. The specific instrumentation and testing parameters are shown in Table 13 and Table 14.

TABLE 13

Parameters of HPLC for solubility, molar ratio and purity

| Parameters | Settings |
|---|---|
| Chromatographic column | Waters Acquity UPLC BCH C18, 50 × 2.1 mm, 1.7 μm |
| Mobile phases | A: $H_2O$ with 0.1% TFA<br>B: ACN with 0.1% TFA |

TABLE 13-continued

| Parameters of HPLC for solubility, molar ratio and purity | | |
|---|---|---|
| Parameters | Settings | |
| Gradients | Time (min) | % mobile phase B |
| | 0.0 | 5 |
| | 6.0 | 80 |
| | 8.0 | 80 |
| | 8.1 | 5 |
| | 10.0 | 5 |
| Time | 10 minutes | |
| Flow rate | 1.0 ml/min | |
| Injection volume | 10 microliter | |
| Detection wavelength | 254 nm | |
| Column temperature | 30° C. | |
| Diluent | ACN/$H_2O$ (1:1, v:v)* | |

*Sulfuric acid is added to help dissolve when formulating.

TABLE 14

| parameters of IC | |
|---|---|
| Parameters | Settings |
| Chromatographic column | IonPac AS18 Analytical Column (4 × 250 mm) |
| Mobile phase | 20 mM sodium hydroxide |
| Injection volume | 25 μL |
| Flow rate | 1.0 ml/min |
| Sample chamber temperature | 35° C. |
| Column temperature | 35° C. |
| Current | 80 mA |
| Run time | 40 minutes |

II. Preparation and Characterization of Salts

1. Preparation and Characterization of Phosphate Crystal Form A

The hydrate crystal form A of compound of formula (I) was used a starting material to prepare the phosphate and the specific steps for preparation are as follows:

1) 24 μL of concentrated phosphoric acid (about 85%) was charged into a 20 mL glass vial.

2) About 200 mg of the hydrate crystal form A of compound of formula (I) was weighed and charged into a 20 mL glass vial to which 10 mL Acetone/$H_2O$ (v/v, 19:1) was added.

(3) After dispersing and stirring at 25° C. for about 3 days, a milky white suspension was obtained, and a solid was obtained by filtration at room temperature under reduced pressure. The solid was dried at room temperature under vacuum for 3 h to give a white powdered sample. The XRPD results showed that the sample was a crystal, while the HPLC/IC results showed that a molar ratio of compound of formula (I) to phosphate was 1.00:1.25, which was presumed that the high phosphate content might be caused by unreacted phosphoric acid residue.

(4) To remove the possible residual phosphoric acid, a total of 2 mL EtOAc was added to the sample obtained in step 3 at room temperature for suspension and stirring for about 5 h. The solid was separated by centrifugation and transferred to room temperature and dried under vacuum for about 13 h to give the phosphate crystal form A.

Figure 27:
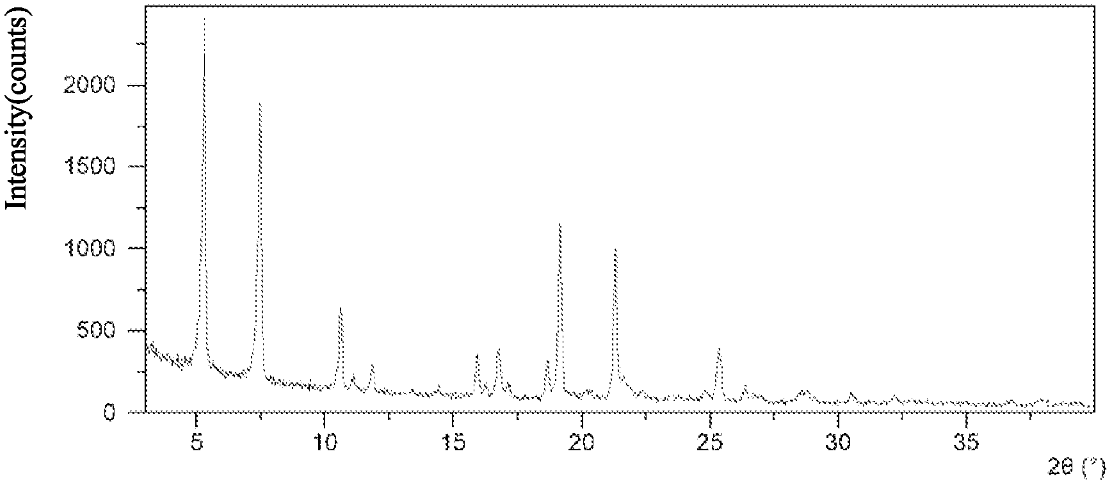
FIG. 27 illustrates an XRPD diagram for phosphate crystal form A of compound of formula (I).

The XRPD diagram of phosphate crystal form A is shown in FIG. 27, and the specific data are presented in the following table.

TABLE 15

| XRPD data of phosphate crystal form A | | | | |
|---|---|---|---|---|
| Pos. [°2θ] | Height [cts] | FWHM Left [°2θ] | d-spacing [Å] | Rel. Int. [%] |
| 5.29 | 2079.47 | 0.1023 | 16.71 | 100.00 |
| 7.47 | 1638.65 | 0.1279 | 11.84 | 78.80 |
| 10.61 | 491.52 | 0.1023 | 8.34 | 23.64 |
| 11.09 | 78.10 | 0.1535 | 7.98 | 3.76 |
| 11.85 | 162.84 | 0.1023 | 7.47 | 7.83 |
| 13.35 | 21.64 | 0.3070 | 6.63 | 1.04 |
| 14.39 | 33.02 | 0.3070 | 6.15 | 1.59 |
| 15.94 | 243.17 | 0.1023 | 5.56 | 11.69 |
| 16.26 | 91.84 | 0.1279 | 5.45 | 4.42 |
| 16.77 | 296.35 | 0.1535 | 5.29 | 14.25 |
| 17.13 | 97.51 | 0.1279 | 5.18 | 4.69 |
| 18.68 | 228.59 | 0.1279 | 4.75 | 10.99 |
| 19.16 | 1063.18 | 0.1279 | 4.63 | 51.13 |
| 20.24 | 48.60 | 0.3070 | 4.39 | 2.34 |
| 21.32 | 921.24 | 0.1023 | 4.17 | 44.30 |
| 22.34 | 55.08 | 0.1535 | 3.98 | 2.65 |
| 24.85 | 69.00 | 0.1535 | 3.58 | 3.32 |
| 25.36 | 318.30 | 0.1791 | 3.51 | 15.31 |
| 26.39 | 100.25 | 0.1023 | 3.38 | 4.82 |
| 28.66 | 56.73 | 0.6140 | 3.11 | 2.73 |
| 30.53 | 50.27 | 0.1535 | 2.93 | 2.42 |
| 32.21 | 48.13 | 0.1535 | 2.78 | 2.31 |
| 36.77 | 28.97 | 0.2047 | 2.44 | 1.39 |
| 37.94 | 32.30 | 0.4605 | 2.37 | 1.55 |

Figure 28:
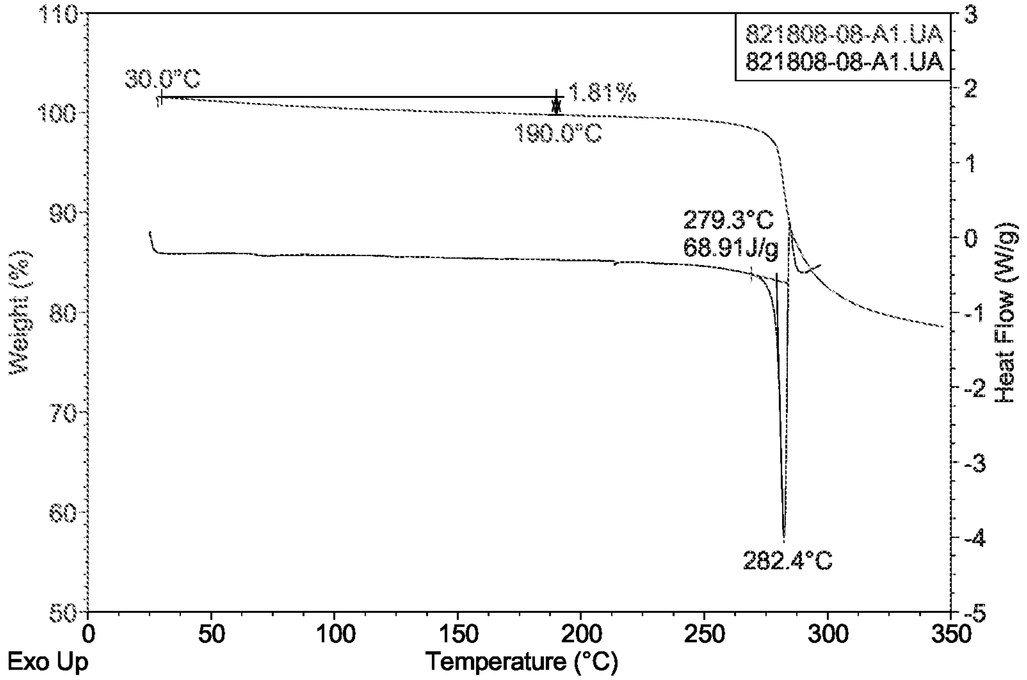
FIG. 28 illustrates TGA/DSC curves for phosphate crystal form A of compound of formula (I).

The TGA/DSC results of the phosphate crystal form A are shown in FIG. 28 from which it can be seen that a weight loss of 1.8% occurred when the sample was heated to 190° C., presumably from the removal of water or solvent from the sample, and that a sharp heat absorption peak could be observed at 279.3° C. (onset temperature), presumably from the sample melting. Based on the fact that a small amount of weight loss occurred before sample melting in TGA and only a single melt heat absorption peak is present in DSC, the phosphate crystal form A is determined to be probably an anhydrous crystal form. The HPLC/IC results show that a molar ratio of compound of formula (I) to phosphate in the sample is 1:1.

2. Preparation and Characterization of Maleate Crystal Form A

The hydrate crystal form A of compound of formula (I) was used a starting material to prepare the maleate and the specific steps for preparation are as follows:

1) About 200 mg of compound hydrate crystal form A of formula (I) was weighed and charged into a 20 mL glass vial.

(2) 53 mg of maleic acid and 10 mL of Acetone/$H_2O$ (v/v, 19:1) were added to the 20 mL glass vial.

(3) After dispersing and stirring at 25° C. for about 3 days, a milky white suspension was obtained, and a solid was obtained by filtration at room temperature under reduced pressure. The solid was dried at room temperature under vacuum for 3 h to give a white powdered sample. The XRPD results showed that the sample was a crystal, while the NMR results showed that a molar ratio of compound of formula (I) to maleic acid in the sample was 1.00:0.86, which was presumed that there was a small amount of unreacted compound of formula (I) in the sample and the salt formation of the sample might not be sufficient.

(4) To promote the salt formation of the sample fully, 10 mg of maleic acid was added to 163 mg of the sample obtained in step 3. After the mixture was stirred at 50° C. for about 14 h in 2 mL EtOAc, the solid was transferred to dry at room temperature under vacuum for about 2 h. After drying, a crystal was obtained and named as maleate crystal form A. XRPD and NMR tests were performed.

Figure 29:
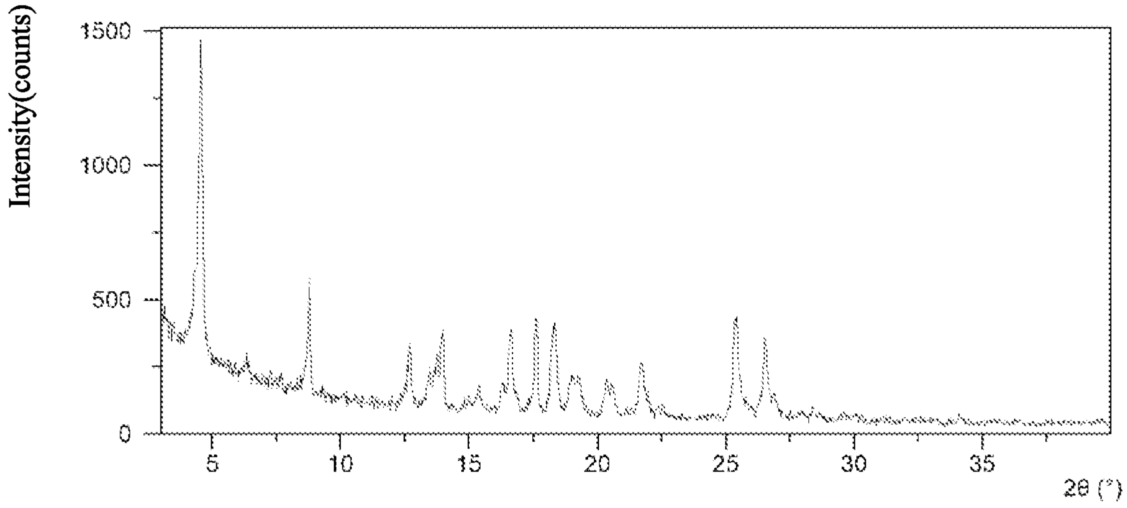
FIG. 29 illustrates an XRPD diagram for maleate crystal form A of compound of formula (I).

The XRPD results of the maleate crystal form A are shown in FIG. 29, and the specific data are as follows.

TABLE 16

XRPD data of maleate crystal form A

| Pos. [°2θ] | Height [cts] | FWHM Left [°2θ] | d-spacing [Å] | Rel. Int. [%] |
|---|---|---|---|---|
| 4.55 | 1141.77 | 0.1279 | 19.40 | 100.00 |
| 6.27 | 37.47 | 0.3070 | 14.09 | 3.28 |
| 8.78 | 418.96 | 0.1023 | 10.08 | 36.69 |
| 12.69 | 230.85 | 0.1023 | 6.98 | 20.22 |
| 13.46 | 117.71 | 0.1279 | 6.58 | 10.31 |
| 13.74 | 195.15 | 0.1023 | 6.45 | 17.09 |
| 13.96 | 262.37 | 0.1023 | 6.34 | 22.98 |
| 15.37 | 85.66 | 0.1535 | 5.77 | 7.50 |
| 16.31 | 104.44 | 0.1023 | 5.43 | 9.15 |
| 16.62 | 299.52 | 0.1535 | 5.33 | 26.23 |
| 17.61 | 354.03 | 0.1023 | 5.04 | 31.01 |
| 18.32 | 319.41 | 0.2303 | 4.84 | 27.97 |
| 19.02 | 133.11 | 0.2047 | 4.66 | 11.66 |
| 19.28 | 139.17 | 0.1279 | 4.60 | 12.19 |
| 20.36 | 127.13 | 0.1791 | 4.36 | 11.13 |
| 20.58 | 112.11 | 0.1279 | 4.31 | 9.82 |
| 21.72 | 201.85 | 0.1791 | 4.09 | 17.68 |
| 25.39 | 368.95 | 0.1791 | 3.51 | 32.31 |
| 26.53 | 301.33 | 0.1535 | 3.36 | 26.39 |

The NMR results show that a molar ratio of compound of formula (I) to maleic acid is 1:1.

Figure 30:
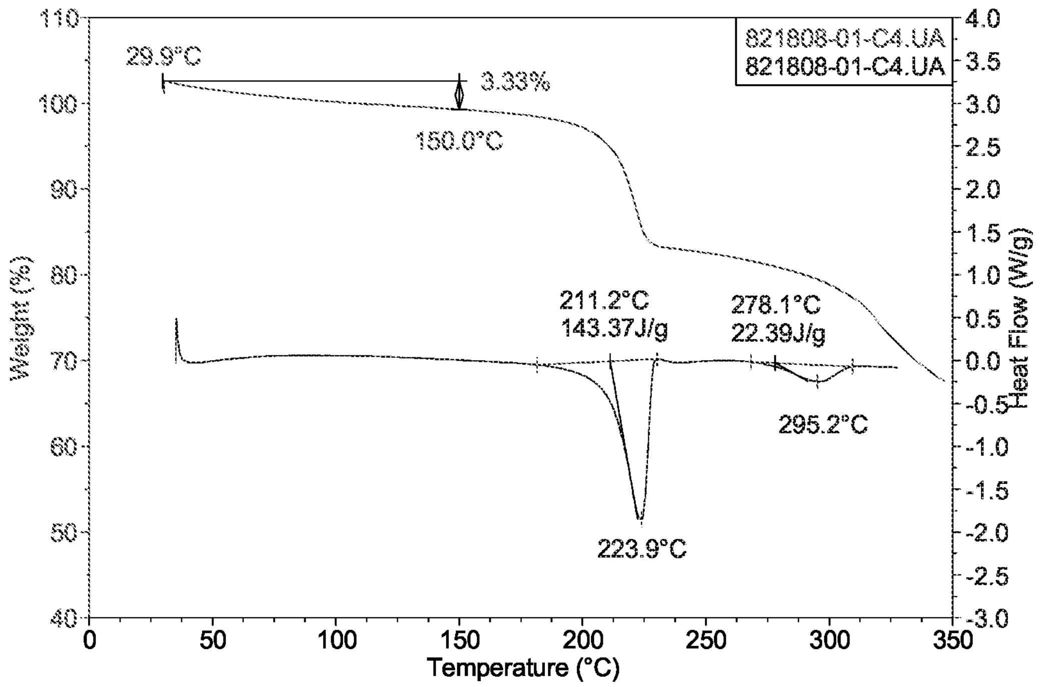
FIG. 30 illustrates TGA/DSC curves for maleate crystal form A of compound of formula (I).

The TGA/DSC results of the maleate crystal form A are shown in FIG. 30, and the results show that a weight loss of 3.3% occurred when the sample was heated to 150° C. and that two thermal signals could be observed at 211.2 and 278.1° C. (onset temperature).

3. Preparation and Characterization of Methanesulfonate Crystal Form B

The hydrate crystal form A of compound of formula (I) was used a starting material to prepare the methanesulfonate and the specific steps for preparation are as follows:

1) About 200 mg of the hydrate crystal form A of compound of formula (I) was weighed and charged into a 20 mL glass vial.

2) 54 mg of methanesulfonic acid and 10 mL of EtOAc were added to a 20 mL glass vial.

3) After dispersing and stirring at 25° C. for about 3 days, a milky white suspension was obtained, and a solid was obtained by filtration at room temperature under reduced pressure. The solid was dried at room temperature under vacuum for 3 h to give a white powdered sample, i.e., methanesulfonate crystal form B.

Figure 31:
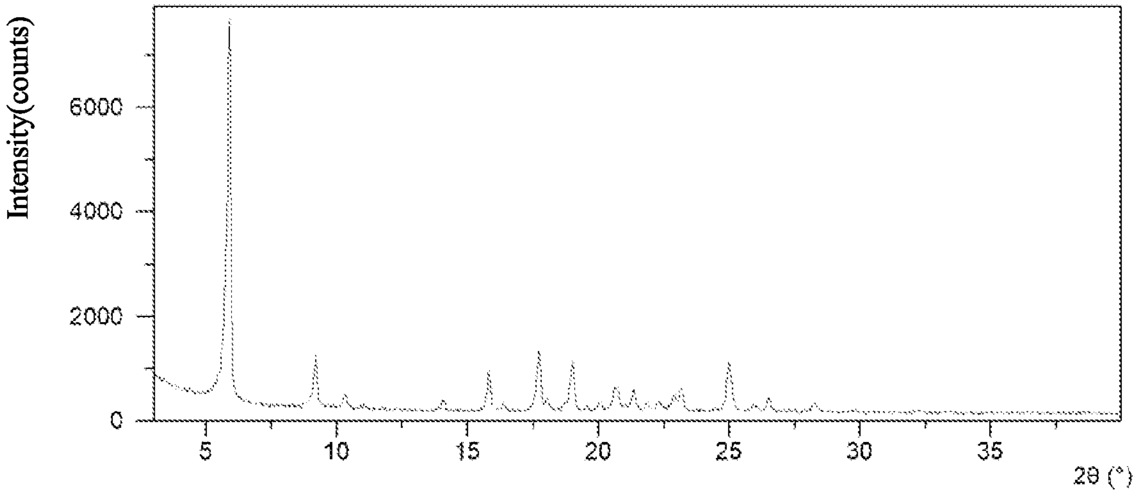
FIG. 31 illustrates an XRPD diagram for methanesulfonate crystal form B of compound of formula (I).

The XRPD results of the resulting methanesulfonate crystal form B are shown in FIG. 31, and the specific data are as follows.

TABLE 17

XRPD data of methanesulfonate crystal form B

| Pos. [°2θ] | Height [cts] | FWHM Left [°2θ] | d-spacing [Å] | Rel. Int. [%] |
|---|---|---|---|---|
| 5.91 | 7126.77 | 0.1023 | 14.96 | 100.00 |
| 9.22 | 957.46 | 0.1023 | 9.60 | 13.43 |
| 10.33 | 252.21 | 0.1023 | 8.56 | 3.54 |
| 14.10 | 206.38 | 0.1279 | 6.28 | 2.90 |
| 15.83 | 761.22 | 0.1023 | 5.60 | 10.68 |
| 16.39 | 179.87 | 0.1023 | 5.41 | 2.52 |
| 17.73 | 1149.72 | 0.1535 | 5.00 | 16.13 |
| 18.05 | 250.09 | 0.1023 | 4.91 | 3.51 |
| 19.02 | 983.65 | 0.1535 | 4.67 | 13.80 |
| 19.57 | 109.14 | 0.1535 | 4.54 | 1.53 |
| 20.08 | 185.91 | 0.1279 | 4.42 | 2.61 |
| 20.61 | 459.42 | 0.1279 | 4.31 | 6.45 |
| 21.36 | 423.87 | 0.1279 | 4.16 | 5.95 |
| 21.90 | 167.00 | 0.1535 | 4.06 | 2.34 |
| 22.31 | 177.61 | 0.1535 | 3.98 | 2.49 |
| 22.90 | 319.35 | 0.1279 | 3.88 | 4.48 |
| 23.18 | 424.35 | 0.1279 | 3.84 | 5.95 |
| 25.01 | 980.92 | 0.1535 | 3.56 | 13.76 |
| 25.98 | 105.69 | 0.2047 | 3.43 | 1.48 |
| 26.54 | 279.95 | 0.1279 | 3.36 | 3.93 |
| 28.26 | 185.42 | 0.1535 | 3.16 | 2.60 |

The NMR results of the methanesulfonate crystal form B show that a molar ratio between the compound of formula (I) and methanesulfonic acid in the sample is 1:1.

Figure 32:
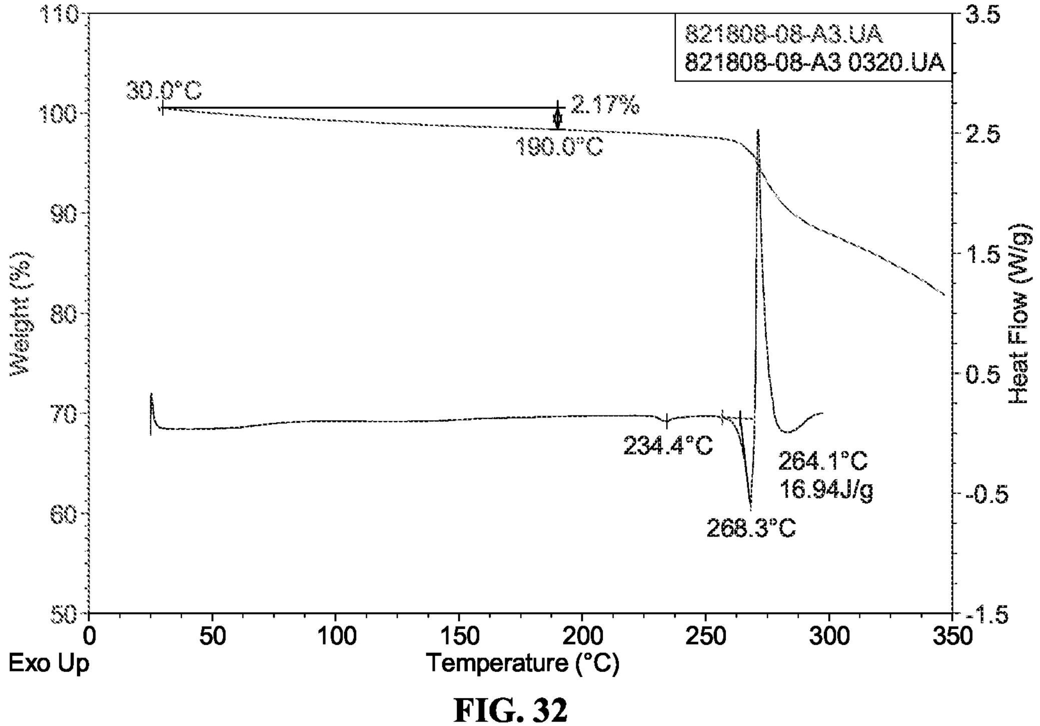
FIG. 32 illustrates TGA/DSC curves for methanesulfonate crystal form B of compound of formula (I).

The TGA/DSC results of the methanesulfonate crystal form B are shown in FIG. 32. A weight loss of 2.2% occurred when the sample was heated to 190° C., presumably from the removal of water or solvent from the sample, and two heat absorption signals could be observed at 234.4° C. (peak temperature) and 264.1° C. (onset temperature). Based on the fact that a small amount of slow weight loss occurred before sample decomposition in TGA and a smoother curve is showed before 190° C. in DSC, it is assumed that the methanesulfonate crystal form B is an anhydrous crystal form.

4. Preparation and Characterization of Hydrochloride Crystal Form A

The hydrochloride was prepared from the hydrate crystal form A of compound of formula (I) by dispersing and stirring the hydrate crystal form A with hydrochloric acid at a molar ratio of 1:1 in EtOAc for about 3 days, and then followed by centrifugation for isolation. The solid was transferred to dry at room temperature under vacuum for 2 hours to give the hydrochloride crystal form A.

Figure 33:
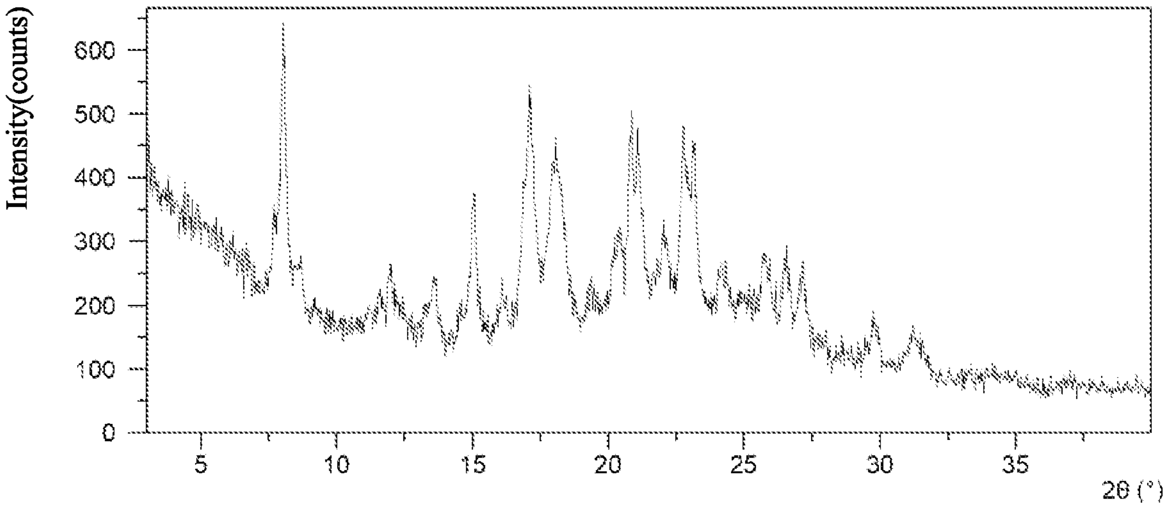
FIG. 33 illustrates an XRPD diagram of hydrochloride crystal form A of compound of formula (I).

The XRPD results of the hydrochloride crystal form A are shown in FIG. 33, and the specific data are as follows.

TABLE 18

XRPD data of hydrochloride crystal form A

| Pos. [°2θ] | Height [cts] | FWHM Left [°2θ] | d-spacing [Å] | Rel. Int. [%] |
|---|---|---|---|---|
| 8.05 | 374.07 | 0.1279 | 10.99 | 100.00 |
| 8.62 | 62.21 | 0.2047 | 10.26 | 16.63 |
| 11.96 | 101.32 | 0.1279 | 7.40 | 27.09 |
| 13.59 | 89.51 | 0.1535 | 6.52 | 23.93 |
| 15.04 | 213.26 | 0.1535 | 5.89 | 57.01 |
| 16.12 | 72.53 | 0.2047 | 5.50 | 19.39 |
| 17.11 | 351.01 | 0.1279 | 5.18 | 93.84 |
| 18.02 | 293.56 | 0.4093 | 4.92 | 78.48 |
| 19.39 | 90.52 | 0.2558 | 4.58 | 24.20 |
| 20.44 | 190.64 | 0.1791 | 4.35 | 50.96 |
| 20.84 | 367.93 | 0.1535 | 4.26 | 98.36 |
| 21.09 | 338.82 | 0.1023 | 4.21 | 90.58 |

TABLE 18-continued

| XRPD data of hydrochloride crystal form A | | | | |
|---|---|---|---|---|
| Pos. [°2θ] | Height [cts] | FWHM Left [°2θ] | d-spacing [Å] | Rel. Int. [%] |
| 22.07 | 185.11 | 0.1535 | 4.03 | 49.49 |
| 22.77 | 354.47 | 0.1279 | 3.91 | 94.76 |
| 23.14 | 329.71 | 0.1023 | 3.84 | 88.14 |
| 24.22 | 135.59 | 0.3070 | 3.67 | 36.25 |
| 25.73 | 170.19 | 0.1535 | 3.46 | 45.50 |
| 26.55 | 155.10 | 0.2558 | 3.36 | 41.46 |
| 27.14 | 138.13 | 0.3070 | 3.29 | 36.93 |
| 29.79 | 81.46 | 0.3070 | 3.00 | 21.78 |
| 31.27 | 60.27 | 0.7164 | 2.86 | 16.11 |

Figure 34:
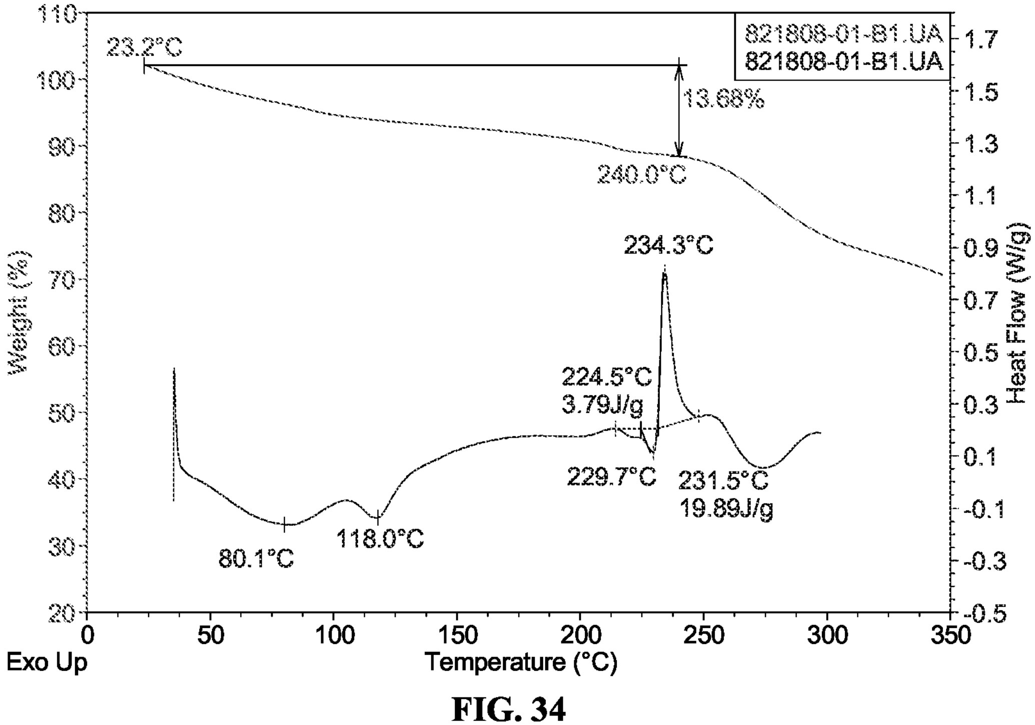
FIG. 34 illustrates TGA/DSC curves for hydrochloride crystal form A of compound of formula (I).

The TGA/DSC results of the hydrochloride crystal form A are shown in FIG. 34. The results show that a weight loss of 13.7% occurred when the sample was heated to 240° C., and three heat absorption peaks could be observed at 80.1, 118.0° C. (peak temperature) and 224.5° C. (onset temperature), and an exothermic signal could be observed at 231.5° C. (onset temperature). The HPLC/IC results show that a molar ratio of the compound of formula (I) to chloride ion in the hydrochloride crystal form A is 1:0.7. Presumably, the sample may not be sufficiently salt-forming.

5. Preparation and Characterization of Tartrate Crystal Form A

The tartrate was prepared from the hydrate crystal form A of compound of formula (I) by dispersing and stirring the hydrate crystal form A with tartaric acid at a molar ratio of 1:1 in EtOAc for about 3 days, and then followed by centrifugation for isolation. The solid was transferred to dry at room temperature under vacuum for 2 hours to give the tartrate crystal form A.

Figure 35:
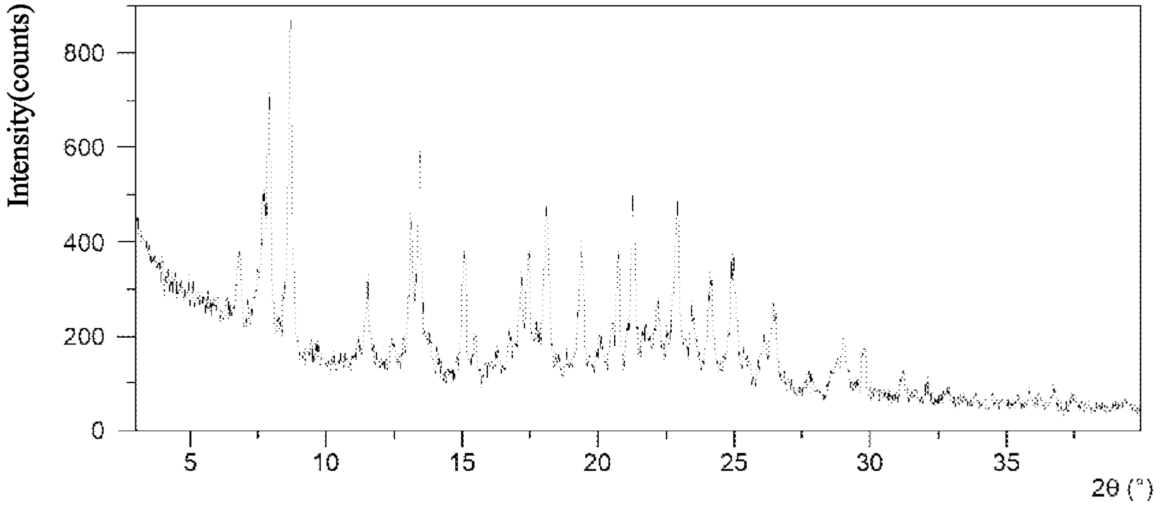
FIG. 35 illustrates an XRPD diagram for tartrate crystal form A of compound of formula (I).

The XRPD results of the tartrate crystal form A are shown in FIG. 35, and the specific data are as follows.

TABLE 19

| XRPD data of tartrate crystal form A | | | | |
|---|---|---|---|---|
| Pos. [°2θ] | Height [cts] | FWHM Left [°2θ] | d-spacing [Å] | Rel. Int. [%] |
| 6.81 | 140.12 | 0.1791 | 12.98 | 20.44 |
| 7.90 | 511.71 | 0.1023 | 11.19 | 74.64 |
| 8.69 | 685.59 | 0.1279 | 10.18 | 100.00 |
| 11.51 | 181.99 | 0.1023 | 7.69 | 26.55 |
| 12.45 | 53.09 | 0.1535 | 7.11 | 7.74 |
| 13.12 | 319.94 | 0.1279 | 6.75 | 46.67 |
| 13.43 | 461.11 | 0.1023 | 6.59 | 67.26 |
| 15.08 | 248.99 | 0.1535 | 5.88 | 36.32 |
| 15.48 | 76.83 | 0.1023 | 5.73 | 11.21 |
| 16.74 | 91.52 | 0.1023 | 5.30 | 13.35 |
| 17.17 | 215.38 | 0.1279 | 5.16 | 31.42 |
| 17.44 | 253.58 | 0.1023 | 5.09 | 36.99 |
| 18.11 | 345.76 | 0.1535 | 4.90 | 50.43 |
| 19.40 | 277.33 | 0.1535 | 4.58 | 40.45 |
| 20.08 | 89.85 | 0.2047 | 4.42 | 13.11 |
| 20.74 | 270.23 | 0.1023 | 4.28 | 39.42 |
| 21.28 | 396.79 | 0.1535 | 4.17 | 57.88 |
| 21.75 | 114.73 | 0.1535 | 4.09 | 16.74 |
| 22.18 | 177.45 | 0.1279 | 4.01 | 25.88 |
| 22.90 | 370.86 | 0.1279 | 3.88 | 54.09 |
| 23.46 | 173.98 | 0.1279 | 3.79 | 25.38 |
| 24.15 | 218.34 | 0.2047 | 3.69 | 31.85 |
| 24.95 | 259.68 | 0.1023 | 3.57 | 37.88 |
| 26.10 | 107.77 | 0.2047 | 3.41 | 15.72 |
| 26.47 | 176.90 | 0.1535 | 3.37 | 25.80 |
| 27.76 | 28.93 | 0.4093 | 3.21 | 4.22 |
| 29.04 | 112.83 | 0.1535 | 3.08 | 16.46 |
| 29.78 | 100.89 | 0.1535 | 3.00 | 14.72 |
| 31.19 | 53.57 | 0.2047 | 2.87 | 7.81 |

TABLE 19-continued

| XRPD data of tartrate crystal form A | | | | |
|---|---|---|---|---|
| Pos. [°2θ] | Height [cts] | FWHM Left [°2θ] | d-spacing [Å] | Rel. Int. [%] |
| 32.08 | 24.10 | 0.1535 | 2.79 | 3.51 |
| 32.85 | 24.85 | 0.1535 | 2.73 | 3.62 |
| 35.87 | 29.61 | 0.1535 | 2.50 | 4.32 |
| 36.76 | 37.65 | 0.1535 | 2.44 | 5.49 |
| 37.47 | 25.85 | 0.1535 | 2.40 | 3.77 |

Figure 36:
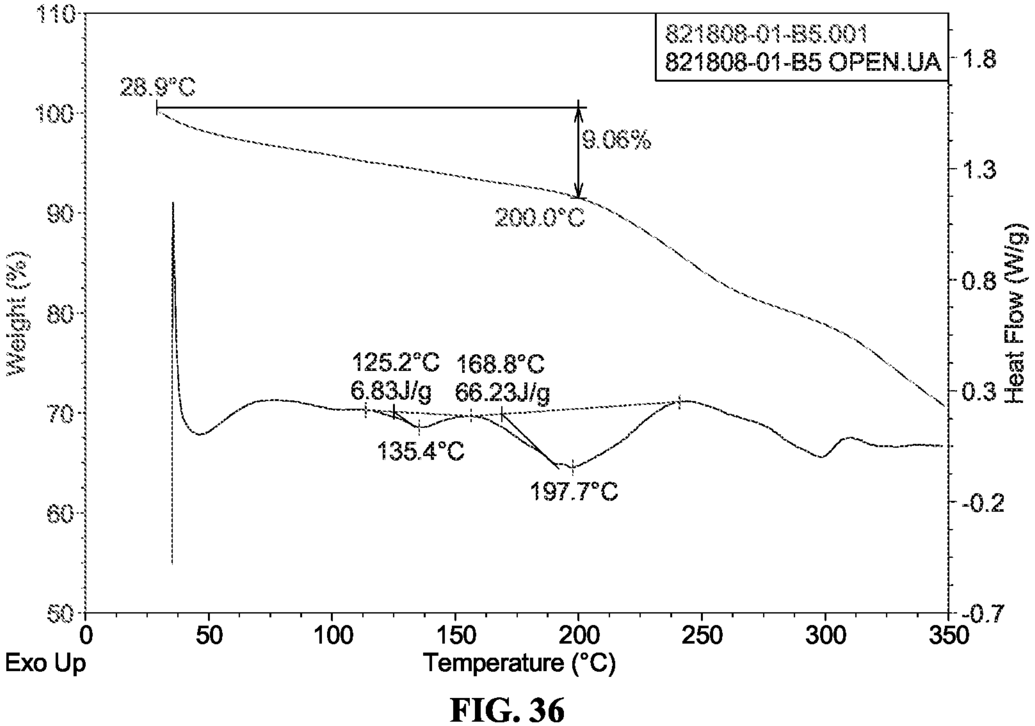
FIG. 36 illustrates TGA/DSC curves for tartrate crystal form A of compound of formula (I).

The TGA/DSC results of tartrate crystal form A are shown in FIG. 36. The results show that a weight loss of 9.1% occurred when the sample was heated to 200° C., and two thermal signals were observed at 125.2 and 168.8° C. (onset temperature). The $^1H$ NMR results show that a molar ratio of compound of formula (I) to tartrate in the tartrate crystal form A is 1:1, in which the 5 Hs overlapping with compound of formula (I) have been subtracted.

6. Preparation and Characterization of Fumarate Crystal Form A

The fumarate was prepared from the hydrate crystal form A of compound of formula (I) by dispersing and stirring the hydrate crystal form A with fumaric acid at a molar ratio of 1:1 in Acetone/H2O (19:1, v/v) for about 3 days, and then followed by centrifugation for isolation. The solid was transferred to dry at room temperature under vacuum for 2 hours to give the fumarate crystal form A.

Figure 37:
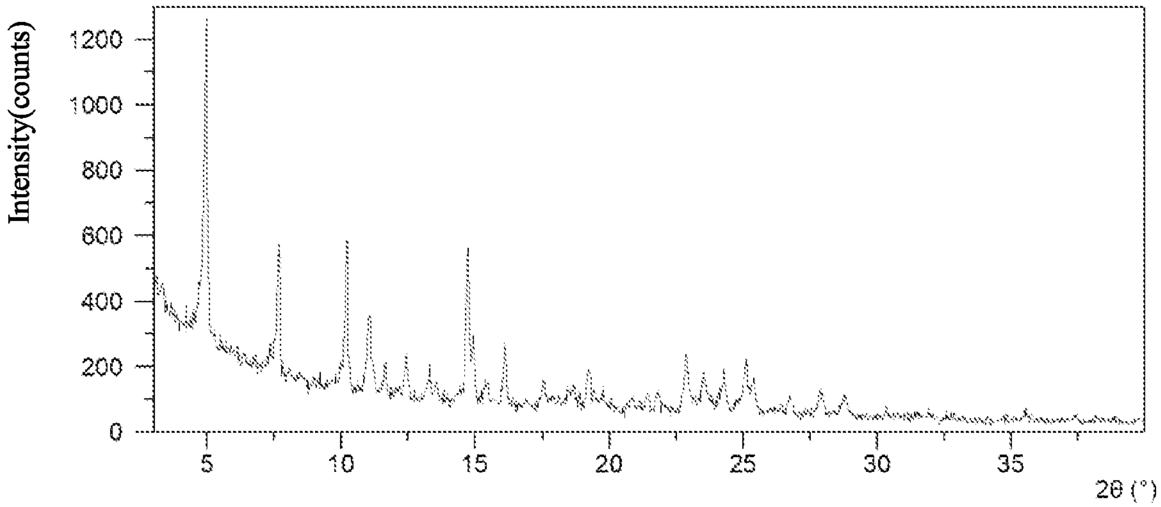
FIG. 37 illustrates an XRPD diagram for fumarate crystal form A of compound of formula (I).

The XRPD results of the fumarate crystal form A are shown in FIG. 37, and the specific data are as follows.

TABLE 20

| XRPD data of fumarate crystal form A | | | | |
|---|---|---|---|---|
| Pos. [°2θ] | Height [cts] | FWHM Left [°2θ] | d-spacing [Å] | Rel. Int. [%] |
| 4.96 | 930.36 | 0.1023 | 17.81 | 100.00 |
| 7.66 | 292.75 | 0.1535 | 11.55 | 31.47 |
| 10.21 | 451.68 | 0.1023 | 8.66 | 48.55 |
| 11.06 | 231.20 | 0.1023 | 8.00 | 24.85 |
| 11.63 | 79.49 | 0.1023 | 7.61 | 8.54 |
| 12.44 | 125.56 | 0.1279 | 7.12 | 13.50 |
| 13.28 | 70.20 | 0.1535 | 6.67 | 7.55 |
| 14.74 | 470.60 | 0.1023 | 6.01 | 50.58 |
| 15.41 | 56.68 | 0.1535 | 5.75 | 6.09 |
| 16.11 | 182.51 | 0.1023 | 5.50 | 19.62 |
| 17.57 | 75.40 | 0.1023 | 5.05 | 8.10 |
| 18.62 | 50.66 | 0.2047 | 4.77 | 5.44 |
| 19.25 | 105.37 | 0.1023 | 4.61 | 11.33 |
| 19.76 | 28.60 | 0.1535 | 4.49 | 3.07 |
| 20.86 | 32.62 | 0.1535 | 4.26 | 3.51 |
| 21.44 | 47.89 | 0.1023 | 4.14 | 5.15 |
| 21.83 | 59.37 | 0.1535 | 4.07 | 6.38 |
| 22.87 | 164.30 | 0.1535 | 3.89 | 17.66 |
| 23.54 | 128.06 | 0.1023 | 3.78 | 13.76 |
| 24.27 | 113.63 | 0.2047 | 3.67 | 12.21 |
| 25.10 | 153.17 | 0.1023 | 3.55 | 16.46 |
| 25.37 | 94.34 | 0.1535 | 3.51 | 10.14 |
| 26.75 | 45.70 | 0.2047 | 3.33 | 4.91 |
| 27.87 | 76.72 | 0.1279 | 3.20 | 8.25 |
| 28.79 | 54.95 | 0.2558 | 3.10 | 5.91 |
| 35.54 | 23.54 | 0.3070 | 2.53 | 2.53 |
| 37.33 | 11.51 | 0.3070 | 2.41 | 1.24 |

Figure 38:
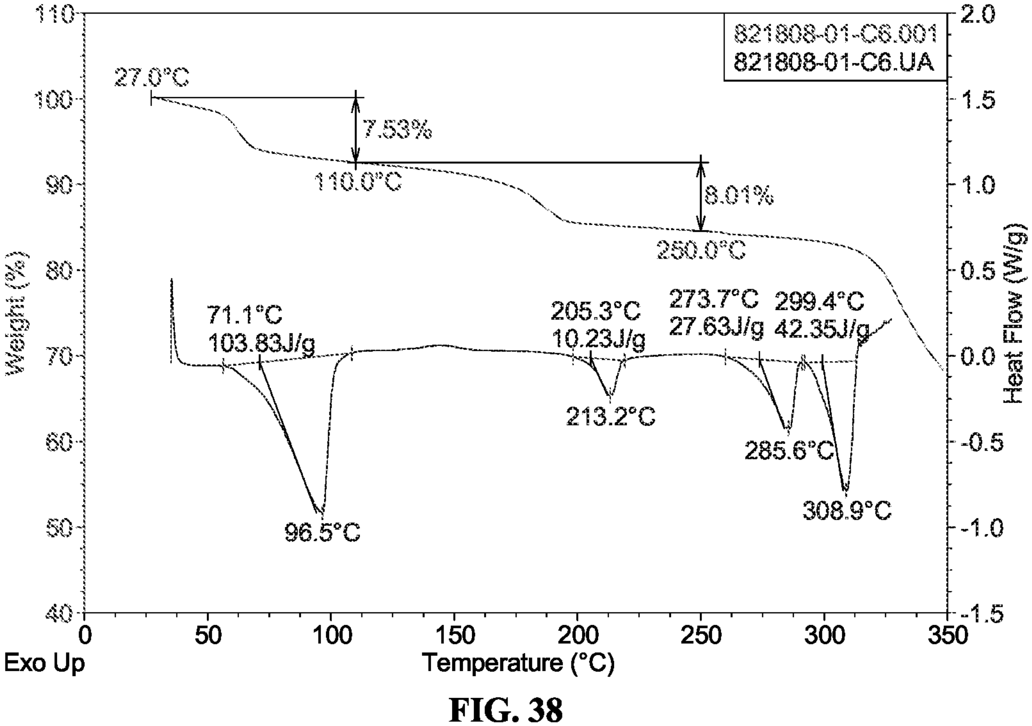
FIG. 38 illustrates TGA/DSC curves for fumarate crystal form A of compound of formula (I).

The TGA/DSC results of fumarate crystal form A are shown in FIG. 38, and the results show that a weight loss of 7.5% occurred when the sample was heated to 110° C. and a weight loss of 8.0% occurred when the heating continued to 250° C.; and that multiple thermal signals could be observed at 71.1, 205.3, 273.7 and 299.4° C. (onset temperature). The $^1$H NMR results show that a molar ratio of compound of formula (I) to fumaric acid in the fumarate crystal form type A is 1:0.6.

7. Preparation and Characterization of Muconate Crystal Form A

The muconate was prepared from the hydrate crystal form A of compound of formula (I) by dispersing and stirring the hydrate crystal form A with muconic acid at a molar ratio of 1:1 in Acetone/$H_2O$ (19:1, v/v) for about 3 days, and then followed by centrifugation for isolation. The solid was transferred to dry at room temperature under vacuum for 2 hours to give the fumarate crystal form A.

Figure 39:
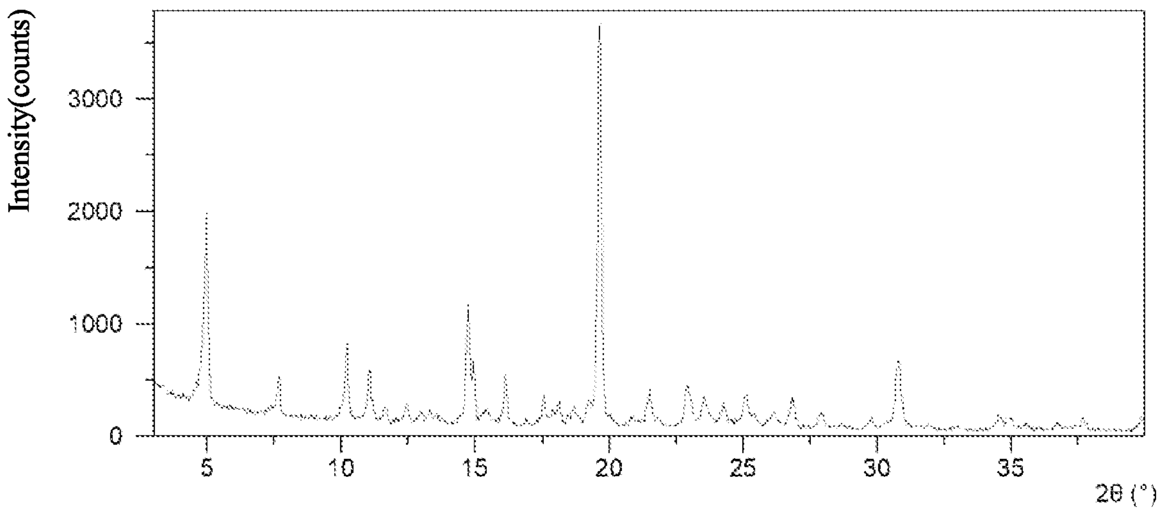
FIG. 39 illustrates an XRPD diagram for fumarate crystal form A of compound of formula (I).

The XRPD results of the muconate crystal form A are shown in FIG. 39, and the specific data are as follows.

TABLE 21

XRPD data of muconate crystal form A

| Pos. [°2θ] | Height [cts] | FWHM Left [°2θ] | d-spacing [Å] | Rel. Int. [%] |
|---|---|---|---|---|
| 4.98 | 1650.53 | 0.1279 | 17.76 | 46.31 |
| 7.69 | 335.69 | 0.1023 | 11.50 | 9.42 |
| 10.22 | 668.21 | 0.1023 | 8.66 | 18.75 |
| 11.07 | 446.78 | 0.1023 | 7.99 | 12.54 |
| 11.66 | 130.25 | 0.1023 | 7.59 | 3.65 |
| 12.45 | 147.00 | 0.1023 | 7.11 | 4.12 |
| 12.99 | 73.25 | 0.1279 | 6.82 | 2.06 |
| 13.32 | 105.10 | 0.1023 | 6.65 | 2.95 |
| 14.75 | 1014.64 | 0.1023 | 6.01 | 28.47 |
| 14.94 | 505.66 | 0.1023 | 5.93 | 14.19 |
| 15.39 | 109.53 | 0.2047 | 5.76 | 3.07 |
| 16.13 | 440.06 | 0.1023 | 5.50 | 12.35 |
| 16.90 | 26.41 | 0.1535 | 5.25 | 0.74 |
| 17.57 | 241.45 | 0.1023 | 5.05 | 6.78 |
| 18.14 | 193.57 | 0.1023 | 4.89 | 5.43 |
| 18.68 | 148.10 | 0.1023 | 4.75 | 4.16 |
| 19.24 | 199.65 | 0.1023 | 4.61 | 5.60 |
| 19.65 | 3563.86 | 0.1279 | 4.52 | 100.00 |
| 20.89 | 71.17 | 0.1535 | 4.25 | 2.00 |
| 21.51 | 325.98 | 0.1791 | 4.13 | 9.15 |
| 21.82 | 84.90 | 0.1279 | 4.07 | 2.38 |
| 22.92 | 353.76 | 0.2047 | 3.88 | 9.93 |
| 23.55 | 264.42 | 0.1535 | 3.78 | 7.42 |
| 24.27 | 184.25 | 0.1279 | 3.67 | 5.17 |
| 25.11 | 273.05 | 0.1535 | 3.55 | 7.66 |
| 25.39 | 116.44 | 0.1791 | 3.51 | 3.27 |
| 26.12 | 136.85 | 0.1535 | 3.41 | 3.84 |
| 26.83 | 272.89 | 0.1791 | 3.32 | 7.66 |
| 27.92 | 121.15 | 0.2047 | 3.20 | 3.40 |
| 28.64 | 28.19 | 0.4093 | 3.12 | 0.79 |
| 29.79 | 97.27 | 0.1279 | 3.00 | 2.73 |
| 30.79 | 610.36 | 0.1791 | 2.90 | 17.13 |
| 33.05 | 26.68 | 0.3582 | 2.71 | 0.75 |
| 34.56 | 141.47 | 0.1279 | 2.60 | 3.97 |
| 34.94 | 102.94 | 0.1535 | 2.57 | 2.89 |
| 35.54 | 49.32 | 0.1535 | 2.53 | 1.38 |
| 36.75 | 62.83 | 0.1535 | 2.45 | 1.76 |
| 37.67 | 109.70 | 0.1023 | 2.39 | 3.08 |

Figure 40:
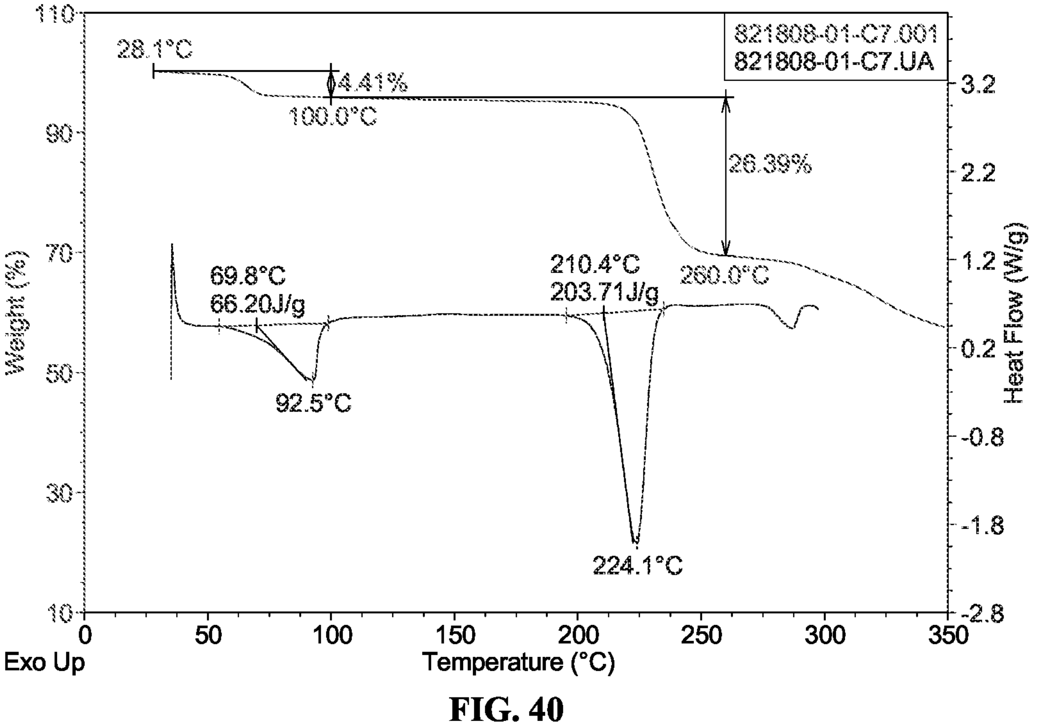
FIG. 40 illustrates TGA/DSC curves for fumarate crystal form A of compound of formula (I).

The TGA/DSC results of the muconate crystal form A are shown in FIG. 40. The results show that a weight loss of 4.4% occurred when the sample was heated to 100° C. and a weight loss of 26.4% occurred when the heating continued to 260° C. and that two thermal signals could be observed at 69.8 and 210.4° C. (onset temperature). The $^1$H NMR results show that a molar ratio of compound of formula (I) to muconic acid in the muconate crystal form A is 1:1.4.

8. Preparation and Characterization of Citrate Crystal Forms A and B

The citrate was prepared from the hydrate crystal form A of compound of formula (I) by dispersing and stirring the hydrate crystal form A with citric acid at a molar ratio of 1:1 in EtOAc or Acetone/$H_2O$ (19:1, v/v) for about 3 days, and then followed by centrifugation for isolation. The solid was transferred to dry at room temperature under vacuum for 2 hours to give the citrate crystal form A or B.

Figure 41:
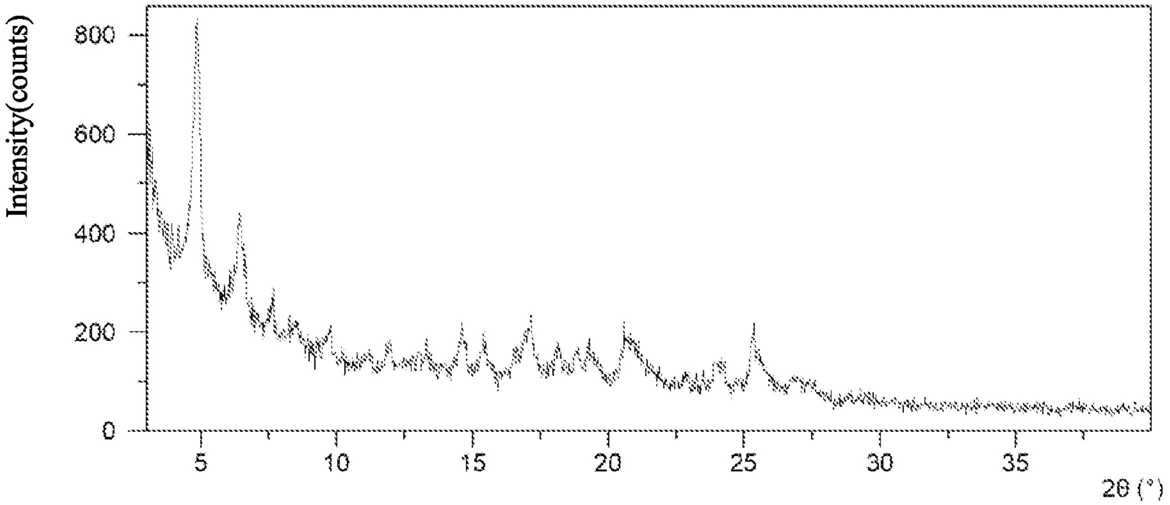
FIG. 41 illustrates an XRPD diagram for citrate crystal form A of compound of formula (I)

The XRPD results of the citrate crystal form A are shown in FIG. 41, and the specific data are as follows.

TABLE 22

XRPD data of citrate crystal form A

| Pos. [°2θ] | Height [cts] | FWHM Left [°2θ] | d-spacing [Å] | Rel. Int. [%] |
|---|---|---|---|---|
| 4.85 | 487.06 | 0.2047 | 18.23 | 100.00 |
| 6.42 | 178.00 | 0.1279 | 13.77 | 36.55 |
| 7.64 | 56.51 | 0.1279 | 11.57 | 11.60 |
| 8.43 | 26.81 | 0.3070 | 10.49 | 5.51 |
| 9.70 | 46.39 | 0.2558 | 9.12 | 9.53 |
| 11.91 | 37.86 | 0.1535 | 7.43 | 7.77 |
| 14.63 | 83.89 | 0.2047 | 6.06 | 17.22 |
| 15.40 | 60.64 | 0.1535 | 5.75 | 12.45 |
| 17.12 | 108.74 | 0.1535 | 5.18 | 22.33 |
| 18.12 | 52.95 | 0.3070 | 4.89 | 10.87 |
| 18.84 | 51.07 | 0.1535 | 4.71 | 10.48 |
| 19.37 | 55.03 | 0.3070 | 4.58 | 11.30 |
| 20.75 | 83.48 | 0.6140 | 4.28 | 17.14 |
| 24.09 | 38.54 | 0.3070 | 3.69 | 7.91 |
| 25.34 | 109.26 | 0.1535 | 3.51 | 22.43 |

Figure 42:
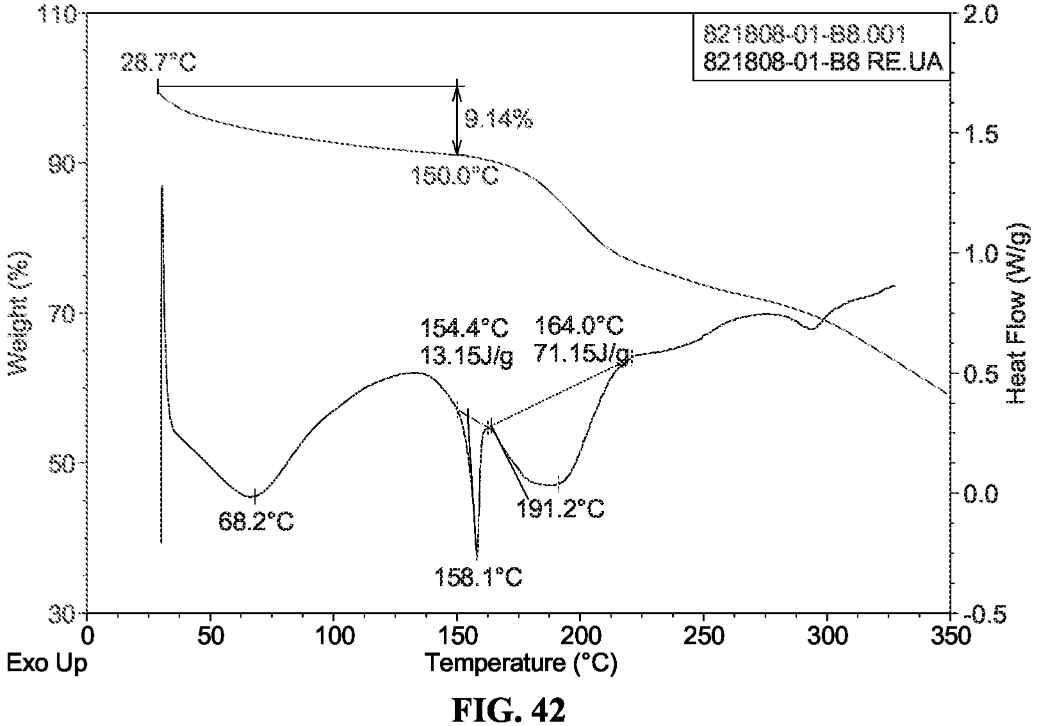
FIG. 42 illustrates TGA/DSC curves for citrate crystal form A of compound of formula (I)

The TGA/DSC results of the citrate crystal form A are shown in FIG. 42. The results show that a weight loss of 9.1% occurred when the sample was heated to 150° C., and three heat absorption peaks could be observed at 68.2° C. (peak temperature), 154.4 and 164.0° C. (onset temperature). The $^1$H NMR results show that a molar ratio of compound of formula (I) to citric acid in the citrate crystal form A was 1:0.5.

Figure 43:
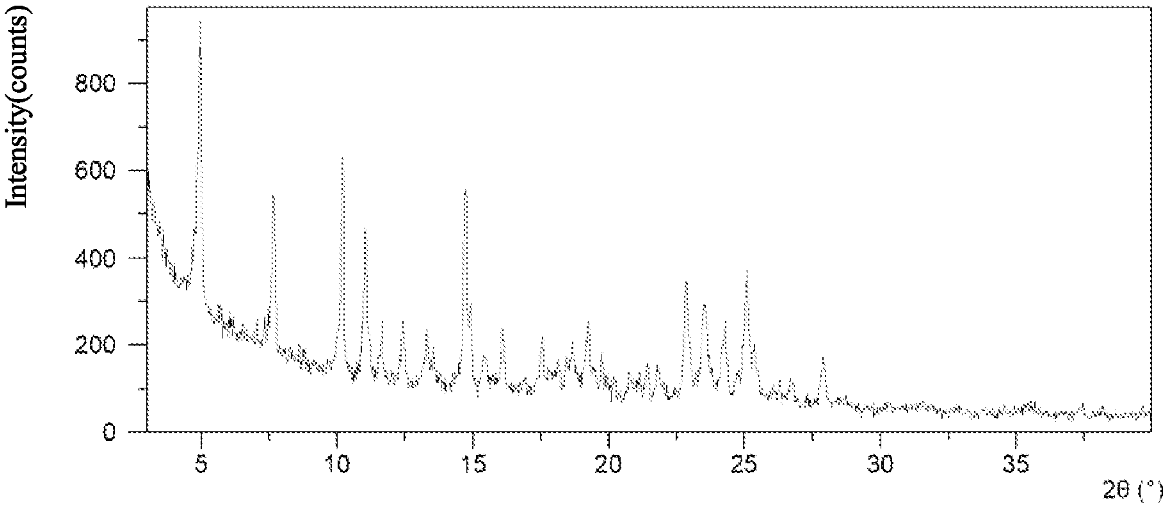
FIG. 43 illustrates an XRPD diagram for citrate crystal form B of compound of formula (I).

The XRPD results of the citrate crystal form B are shown in FIG. 43, and the specific data are as follows.

TABLE 23

XRPD data of citrate crystal form B

| Pos. [°2θ] | Height [cts] | FWHM Left [°2θ] | d-spacing [Å] | Rel. Int. [%] |
|---|---|---|---|---|
| 4.96 | 628.39 | 0.1023 | 17.83 | 100.00 |
| 7.67 | 351.33 | 0.1023 | 11.53 | 55.91 |
| 10.20 | 489.58 | 0.1023 | 8.67 | 77.91 |
| 11.04 | 291.58 | 0.1535 | 8.01 | 46.40 |
| 11.63 | 95.00 | 0.2047 | 7.61 | 15.12 |
| 12.42 | 130.76 | 0.1279 | 7.13 | 20.81 |
| 13.29 | 94.61 | 0.1535 | 6.66 | 15.06 |
| 14.73 | 447.41 | 0.1023 | 6.02 | 71.20 |
| 15.44 | 70.54 | 0.1279 | 5.74 | 11.23 |

TABLE 23-continued

| XRPD data of citrate crystal form B | | | | |
|---|---|---|---|---|
| Pos. [°2θ] | Height [cts] | FWHM Left [°2θ] | d-spacing [Å] | Rel. Int. [%] |
| 16.09 | 137.39 | 0.1279 | 5.51 | 21.86 |
| 17.55 | 116.50 | 0.1023 | 5.05 | 18.54 |
| 18.10 | 50.66 | 0.1535 | 4.90 | 8.06 |
| 18.66 | 95.28 | 0.1535 | 4.76 | 15.16 |
| 19.23 | 155.98 | 0.1023 | 4.61 | 24.82 |
| 20.80 | 42.52 | 0.1535 | 4.27 | 6.77 |
| 21.41 | 65.32 | 0.1023 | 4.15 | 10.39 |
| 21.81 | 63.44 | 0.1535 | 4.08 | 10.10 |
| 22.86 | 265.57 | 0.1279 | 3.89 | 42.26 |
| 23.54 | 216.99 | 0.1535 | 3.78 | 34.53 |
| 24.28 | 174.36 | 0.1279 | 3.67 | 27.75 |
| 25.08 | 287.37 | 0.1023 | 3.55 | 45.73 |
| 26.76 | 57.71 | 0.2047 | 3.33 | 9.18 |
| 27.91 | 113.41 | 0.1279 | 3.20 | 18.05 |

Figure 44:
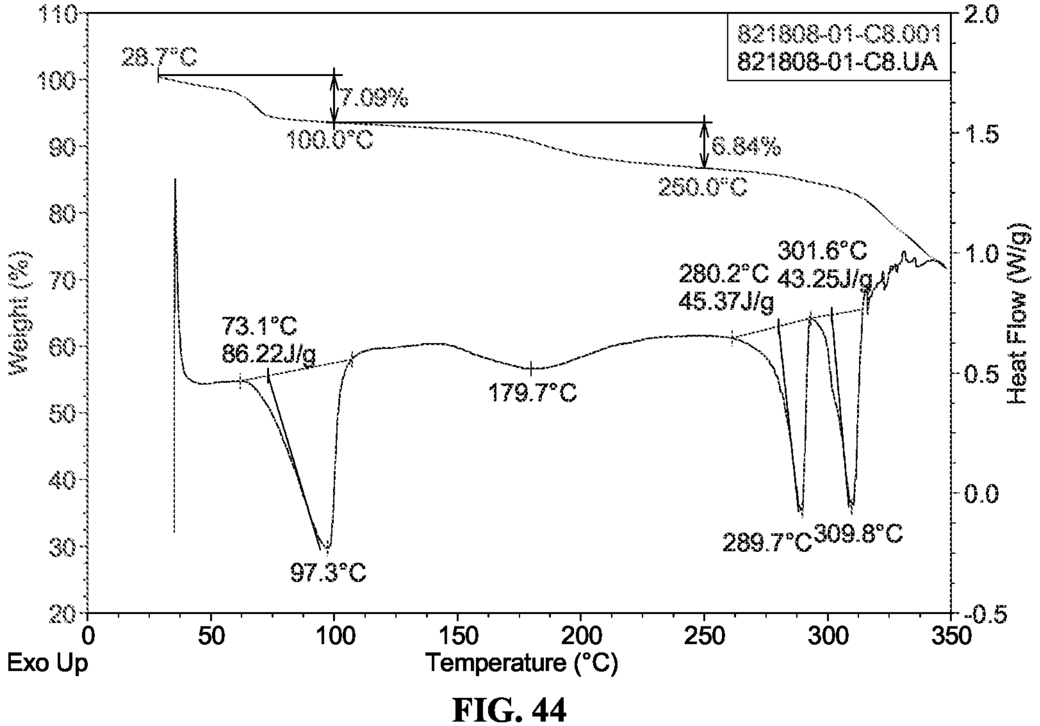
FIG. 44 illustrates TGA/DSC curves for citrate crystal form B of compound of formula (I).

The TGA/DSC results of the citrate crystal form B are shown in FIG. 44, and the results show that a weight loss of 7.1% occurred when the sample was heated to 100° C. and a weight loss of 6.8% occurred when the heating continued to 250° C.; and that four heat absorption peaks were observed at 73.1, 280.2, 301.6° C. (onset temperature) and 179.7° C. (peak temperature). The $^1$H NMR results show that a molar ratio of compound of formula (I) to citric acid in the citrate crystal form B is 1:0.5.

9. Preparation and Characterization of p-Toluenesulfonate Crystal Form A

The p-toluenesulfonate was prepared from the hydrate crystal form A of compound of formula (I) by dispersing and stirring the hydrate crystal form A with p-toluenesulfonic acid at a molar ratio of 1:1 in Acetone/$H_2O$ (19:1, v/v) for about 3 days, and then followed by centrifugation for isolation. The solid was transferred to dry at room temperature under vacuum for 2 hours to give the p-toluenesulfonate crystal form A.

Figure 45:
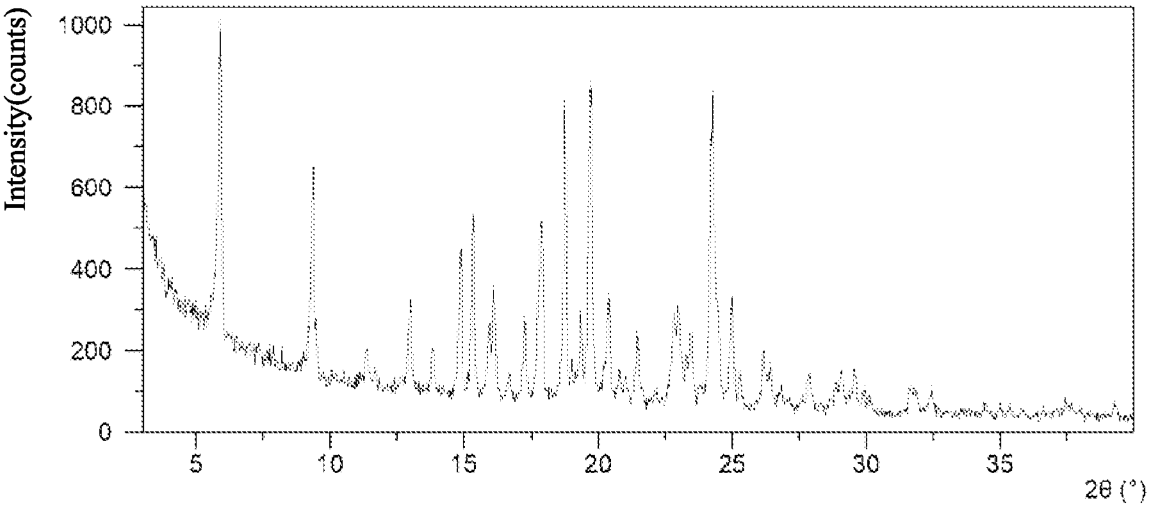
FIG. 45 illustrates an XRPD diagram for p-toluenesulfonate crystal form A of compound of formula (I).

The XRPD results of the p-toluenesulfonate crystal form A are shown in FIG. 45, and the specific data are as follows.

TABLE 24

| XRPD data of p-toluenesulfonate crystal form A | | | | |
|---|---|---|---|---|
| Pos. [°2θ] | Height [cts] | FWHM Left [°2θ] | d-spacing [Å] | Rel. Int. [%] |
| 5.90 | 742.23 | 0.1023 | 14.99 | 97.20 |
| 9.34 | 443.97 | 0.2047 | 9.47 | 58.14 |
| 11.38 | 72.11 | 0.1535 | 7.78 | 9.44 |
| 12.99 | 209.10 | 0.1279 | 6.82 | 27.38 |
| 13.84 | 96.45 | 0.1279 | 6.40 | 12.63 |
| 14.87 | 347.64 | 0.1023 | 5.96 | 45.52 |
| 15.33 | 438.64 | 0.1023 | 5.78 | 57.44 |
| 16.10 | 251.79 | 0.1023 | 5.50 | 32.97 |
| 16.68 | 51.18 | 0.1535 | 5.31 | 6.70 |
| 17.27 | 189.54 | 0.1023 | 5.14 | 24.82 |
| 17.88 | 420.22 | 0.2047 | 4.96 | 55.03 |
| 18.76 | 694.41 | 0.1279 | 4.73 | 90.93 |
| 19.34 | 203.25 | 0.1023 | 4.59 | 26.62 |
| 19.71 | 763.64 | 0.1023 | 4.51 | 100.00 |
| 20.39 | 233.56 | 0.1279 | 4.36 | 30.58 |
| 21.47 | 142.45 | 0.2047 | 4.14 | 18.65 |
| 22.92 | 188.77 | 0.3582 | 3.88 | 24.72 |
| 23.45 | 173.37 | 0.1023 | 3.79 | 22.70 |
| 24.26 | 760.56 | 0.1535 | 3.67 | 99.60 |
| 24.99 | 269.09 | 0.1279 | 3.56 | 35.24 |
| 25.28 | 79.53 | 0.1023 | 3.52 | 10.42 |
| 26.16 | 142.66 | 0.1279 | 3.41 | 18.68 |
| 27.85 | 78.88 | 0.1535 | 3.20 | 10.33 |
| 29.07 | 93.39 | 0.3070 | 3.07 | 12.23 |
| 29.56 | 95.43 | 0.1535 | 3.02 | 12.50 |
| 31.71 | 53.43 | 0.1535 | 2.82 | 7.00 |
| 32.43 | 52.76 | 0.1535 | 2.76 | 6.91 |
| 37.56 | 22.27 | 0.6140 | 2.39 | 2.92 |

Figure 46:
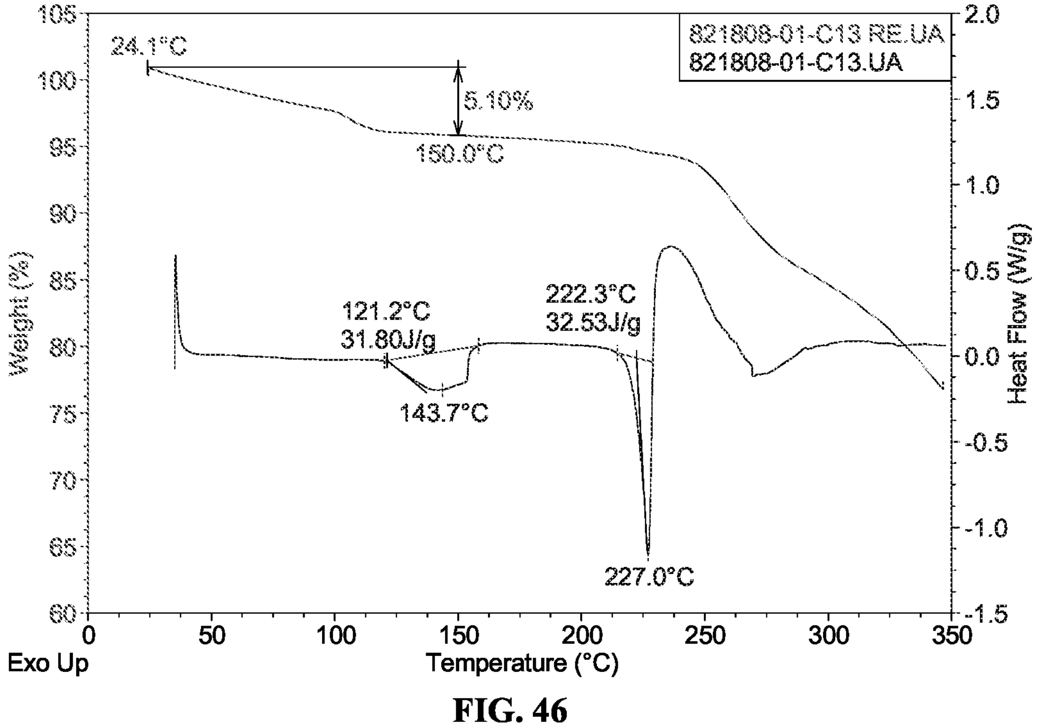
FIG. 46 illustrates TGA/DSC curves for p-toluenesulfonate crystal form A of compound of formula (I).

The TGA/DSC data of p-toluenesulfonate crystal form A was shown in FIG. 46. The results show that a weight loss of 5.1% occurred when the sample was heated to 150° C., and two thermal signals could be observed at 121.2 and 222.3° C. (onset temperature). The $^1$H NMR results show that a molar ratio of compound of formula (I) to p-toluenesulfonate in the p-toluenesulfonate crystal form A is 1:1.

10. Preparation and Characterization of Benzenesulfonate Crystal Forms A and B

The benzenesulfonate was prepared from the hydrate crystal form A of compound of formula (I) by dispersing and stirring the hydrate crystal form A with benzenesulfonic acid at a molar ratio of 1:1 in EtOAc or Acetone/$H_2O$ (19:1, v/v) for about 3 days, and then followed by centrifugation for isolation. The solid was transferred to dry at room temperature under vacuum for 2 hours to give the benzenesulfonate crystal form A or B.

Figure 47:
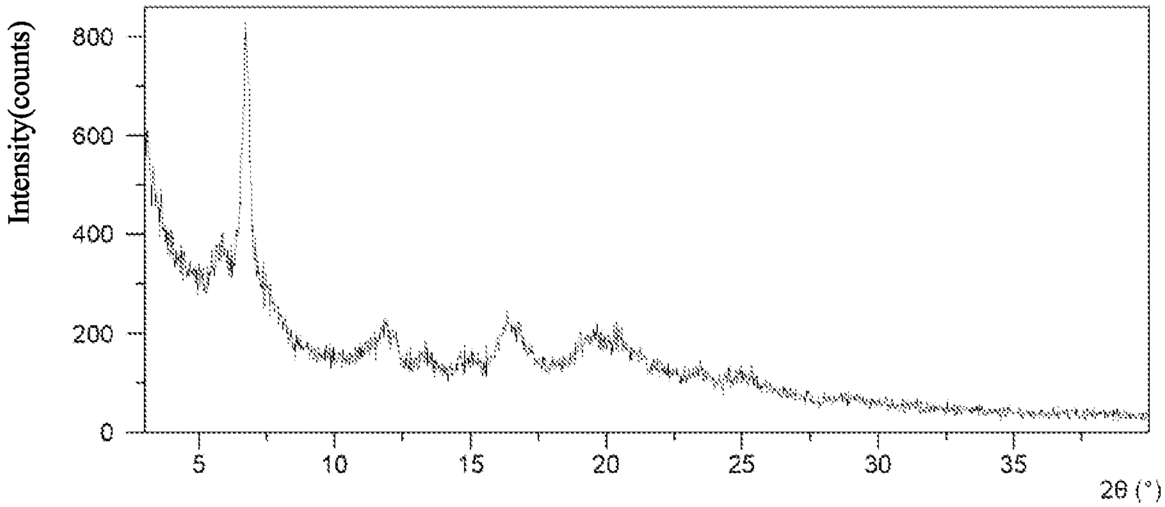
FIG. 47 illustrates an XRPD diagram for benzenesulfonate crystal form A of compound of formula (I).

The XRPD results of the benzenesulfonate crystal form A are shown in FIG. 47, and the specific data are as follows.

TABLE 25

XRPD data of benzenesulfonate crystal form A

| Pos. [°2θ] | Height [cts] | FWHM Left [°2θ] | d-spacing [Å] | Rel. Int. [%] |
|---|---|---|---|---|
| 5.82 | 88.58 | 0.4093 | 15.18 | 16.34 |
| 6.74 | 542.24 | 0.1791 | 13.11 | 100.00 |
| 11.85 | 73.26 | 0.6140 | 7.47 | 13.51 |
| 16.38 | 87.15 | 0.5117 | 5.41 | 16.07 |
| 19.46 | 57.99 | 0.6140 | 4.56 | 10.70 |
| 20.20 | 51.19 | 0.8187 | 4.40 | 9.44 |
| 24.97 | 20.27 | 0.8187 | 3.57 | 3.74 |

Figure 48:
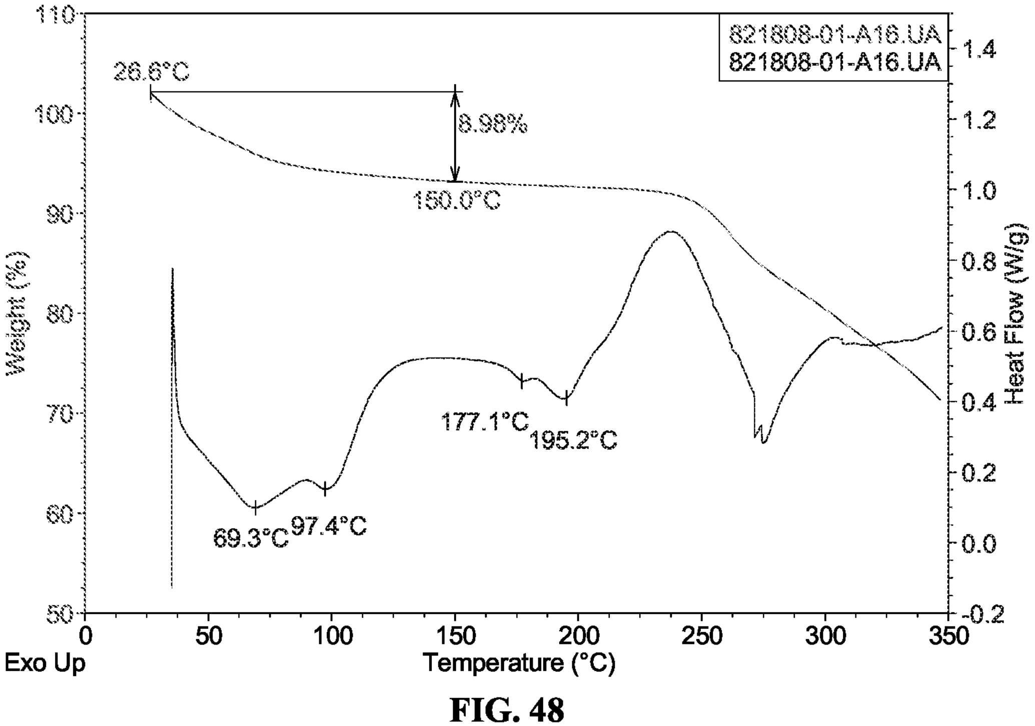
FIG. 48 illustrates TGA/DSC curves for benzenesulfonate crystal form A of compound of formula (I).

The TGA/DSC results of the benzenesulfonate crystal form A are shown in FIG. 48, and the results show that a weight loss of 9.0% occurred when the sample was heated to 150° C., and multiple thermal signals could be observed at 60-200° C. The $^{1}H$ NMR results show that a molar ratio of compound of formula (I) to benzenesulfonic acid in the benzenesulfonate crystal form A is 1:1.

Figure 49:
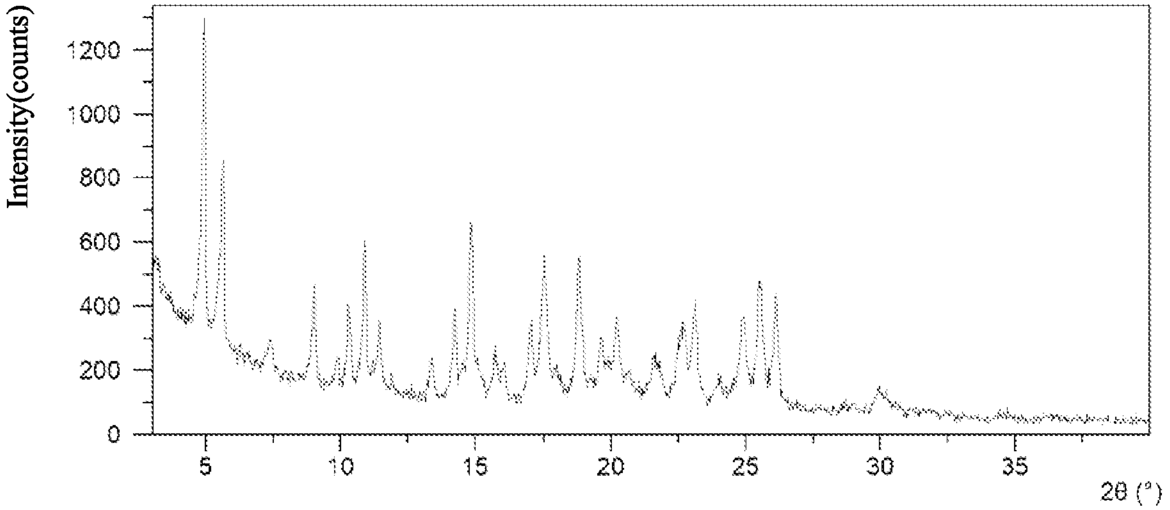
FIG. 49 illustrates an XRPD diagram of crystal form B of benzenesulfonate salt of compound of formula (I).

The XRPD results of the benzenesulfonate crystal form B are shown in FIG. 49, and the specific data are as follows.

TABLE 26

XRPD data of benzenesulfonate crystal form B

| Pos. [°2θ] | Height [cts] | FWHM Left [°2θ] | d-spacing [Å] | Rel. Int. [%] |
|---|---|---|---|---|
| 4.93 | 968.04 | 0.1023 | 17.91 | 100.00 |
| 5.63 | 547.75 | 0.1279 | 15.69 | 56.58 |
| 7.40 | 85.03 | 0.1535 | 11.94 | 8.78 |
| 9.02 | 298.15 | 0.1279 | 9.80 | 30.80 |
| 9.88 | 84.59 | 0.1023 | 8.95 | 8.74 |
| 10.30 | 249.02 | 0.1279 | 8.59 | 25.72 |
| 10.89 | 457.61 | 0.1023 | 8.13 | 47.27 |
| 11.43 | 209.76 | 0.1023 | 7.74 | 21.67 |
| 13.35 | 109.80 | 0.1023 | 6.63 | 11.34 |
| 14.23 | 281.07 | 0.1023 | 6.22 | 29.04 |
| 14.84 | 519.20 | 0.1279 | 5.97 | 53.63 |
| 15.73 | 134.52 | 0.1535 | 5.63 | 13.90 |
| 16.02 | 96.56 | 0.1535 | 5.53 | 9.98 |
| 17.04 | 239.02 | 0.1535 | 5.20 | 24.69 |
| 17.55 | 458.38 | 0.1535 | 5.05 | 47.35 |
| 18.84 | 443.77 | 0.1279 | 4.71 | 45.84 |
| 19.66 | 203.57 | 0.1535 | 4.52 | 21.03 |
| 20.24 | 259.09 | 0.1791 | 4.39 | 26.76 |
| 21.61 | 144.55 | 0.1279 | 4.11 | 14.93 |
| 22.71 | 255.49 | 0.1791 | 3.92 | 26.39 |
| 23.12 | 298.28 | 0.1791 | 3.85 | 30.81 |
| 24'02 | 81.04 | 0'1535 | 3.70 | 8.37 |
| 24.91 | 282.40 | 0.1791 | 3.57 | 29.17 |
| 25.55 | 378.69 | 0.1535 | 3.49 | 39.12 |
| 26.14 | 343.49 | 0.1535 | 3.41 | 35.48 |
| 29.95 | 74.56 | 0.2047 | 2.98 | 7.70 |

Figure 50:
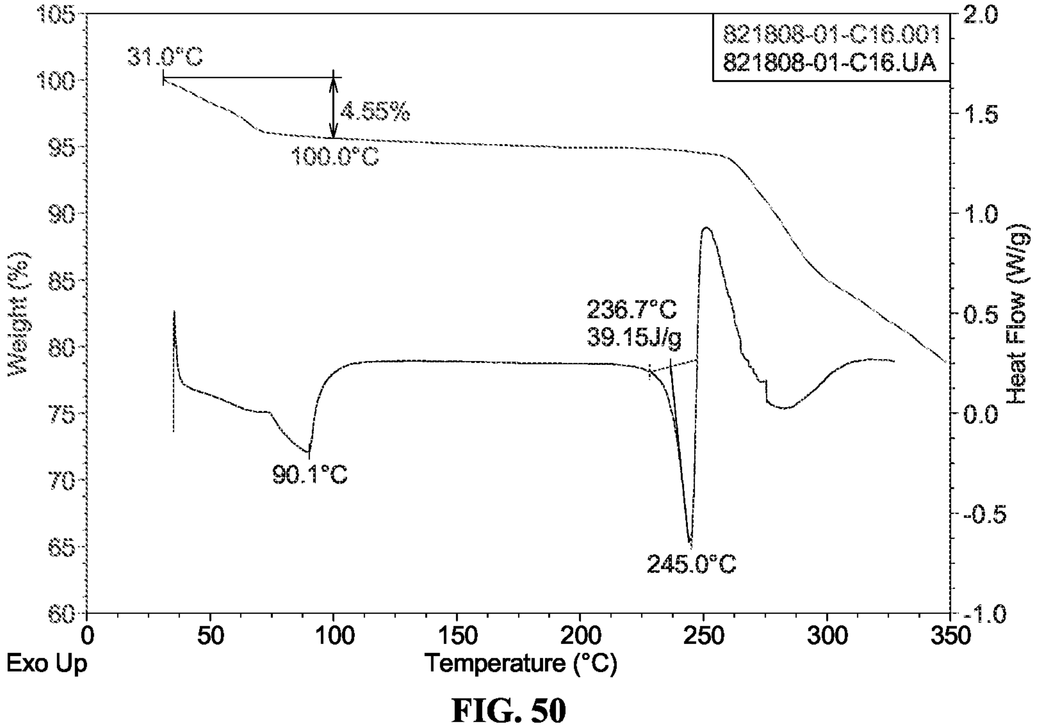
FIG. 50 illustrates TGA/DSC curves for benzenesulfonate crystal form B of compound of formula (I).

The TGA/DSC results of the benzenesulfonate crystal form B was shown in FIG. 50. The results show that a weight loss of 4.6% occurred when the sample was heated to 100° C., and two thermal signals could be observed at 90.1° C. (peak temperature) and 236.7° C. (onset temperature). The $^{1}H$ NMR results show that a molar ratio of compound of formula (I) to benzenesulfonic acid in the benzenesulfonate crystal form B is 1:0.5.

III. Screening of Salt Crystal Forms

Based on the physical characterization data of the above prepared salt crystal forms, phosphate crystal form A, maleate crystal form A and methanesulfonate crystal form B with a higher XRPD diffraction peak intensity (sharp peak), a lower TGA weight loss, a higher DSC melting temperature and a higher safety level of acid were selected for the next study and evaluation.

TABLE 27

Summary of characterization data for salt crystal forms

| Salt crystal form/ sample number | TGA weight loss (%) | DSC heat absorption peak (° C., onset temperature) | NMR molar ratio (compound of formula (I)/ acid) |
|---|---|---|---|
| Phosphate crystal form A | 1.8 (190° C.) | 279.3 | (1:1)# |

TABLE 27-continued

Summary of characterization data for salt crystal forms

| Salt crystal form/ sample number | TGA weight loss (%) | DSC heat absorption peak (° C., onset temperature) | NMR molar ratio (compound of formula (I)/ acid) |
|---|---|---|---|
| Maleate crystal form A | 3.3 (150° C.) | 211.3 | (1:1) |
| Methanesulfonate crystal form B | 2.2 (190° C.) | 234.4*, 264.1 | (1:1) |

*peak temperature.
#measured by IC and HPLC.

IV. Evaluation of Salt Crystal Forms

The evaluation of the three salt crystal forms was carried out in vitro in terms of solubility, solid stability and hygroscopicity.

1. Reagents and Materials

TABLE 28

Reagents used for solubility experiments

| | | |
|---|---|---|
| SGF | NaCl | Sinopharm Chemical Reagent Company |
| | Triton X-100 | Sigma-Aldrich |
| | HCl | Shanghai Ampoule Experimental Technology Co. |
| FeSSIF | Acetic acid | Aiddin |
| | NaOH | Sinopharm Chemical Reagent Company |
| | NaCl | Sinopharm Chemical Reagent Company |
| | SIF powder | Biorelevant |

2. Solubility

To assess the solubility of the three salt forms in different media, a dynamic solubility (1, 2, 4, 24 h) of three batches of samples in biolysis media (simulated gastric SGF and simulated intestinal fluid FeSSIF) at room temperature, and their solubility in ethanol, water, and pH=7.4 phosphate buffer for 24 h were investigated. The specific steps are as follows.

1) About 10 mg of the salt crystal form sample was weighed and charged into an HPLC vial, and 1 mL of ethanol, water, and pH=7.4 phosphate buffer were added, respectively.
2) About 40 mg of the salt crystal form sample was weighed and charged into a 5 mL centrifuge tube, and 4 mL of SGF and FeSSIF were added, respectively.
3) Magnetic suspension stirring at about 750 rpm was performed at 25° C.
4) After equilibration for an adequate time, the solid and supernatant were separated by centrifugation at room temperature, and the supernatant was used for pH and solubility tests.

The experimental results are shown in Table 29. At a feeding concentration of 10 mg/mL, the solubilities of the three salt crystal forms in SGF range from 0.05 to 0.30 mg/mL, among which the solubility of the methanesulfonate crystal form B was relatively high; and the solubilities in FeSSIF range from 0.08 to 6.21 mg/mL, among which the solubilities of the methanesulfonate crystal form B and the maleate crystal form A are relatively high. For water, ethanol and pH=7.4 phosphate buffer, the solubilities of the three salt crystal forms in water range from 0.04 to 1.30 mg/mL, with relatively high solubility of the phosphate crystal form A; the solubilities in ethanol range from 1.14 to 2.14 mg/mL, with relatively high solubility of the maleate crystal form A, and the solubilities in pH=7.4 medium range from 0.02 to 0.15 mg/mL, with relatively high solubility of the methanesulfonate crystal form B.

TABLE 29

Summary 1 of solubilities of three salt crystal forms in different media at 25° C.
Dynamic solubility in SGF, FeSSIF

| | Salt | 1 h | | 2 hs | | 4 hs | | 24 hs | |
|---|---|---|---|---|---|---|---|---|---|
| Medium | crystal form | S | pH | S | pH | S | pH | S | pH |
| SGF | Phosphate crystal form A | 0.08 | 1.7 | 0.08 | 1.7 | 0.06 | 1.7 | 0.05 | 1.6 |
| | Maleate crystal form A | 0.16 | 1.6 | 0.14 | 1.7 | 0.07 | 1.7 | 0.05 | 1.6 |
| | Methane-sulfonate crystal form B | 0.30 | 1.6 | 0.25 | 1.6 | 0.29 | 1.6 | 0.23 | 1.6 |
| FeSSIF | Phosphate crystal form A | 0.26 | 5.0 | 0.23 | 5.0 | 0.17 | 4.8 | 0.08 | 4.8 |
| | Maleate crystal form A | 5.14 | 4.7 | 4.84 | 4.7 | 5.77 | 4.8 | 6.18 | 4.7 |
| | Methane-sulfonate crystal form B | 6.00 | 4.8 | 4.75 | 4.8 | 4.99 | 4.8 | 6.21 | 4.8 |

S: API solubility (mg/mL).
NA: pH not tested.

TABLE 30

Summary 2 of solubilities of three salt crystal forms in different media at 25° C.
Solubility in in ethanol, water, and pH = 7.4 phosphate buffer for 24 h

| Salt crystal form | Ethanol | | Water | | pH = 7.4 phosphate buffer | |
|---|---|---|---|---|---|---|
| (sample batch) | S | pH | S | pH | S | pH |
| Phosphate crystal form A | 1.14 | NA | 1.30 | 2.4 | 0.02 | 6.6 |
| Maleate crystal form A | 2.14 | NA | 0.04 | 2.5 | 0.03 | 6.2 |
| Methane-sulfonate crystal form B | 1.89 | NA | 0.28 | 1.9 | 0.15 | 6.7 |

S: API solubility (mg/mL).
NA: pH not tested.

3. Solid Stability

To evaluate the solid stability of the salt crystal forms, three sample batches were placed at 25° C./60% RH and 40° C./75% RH (wrapped in sealing film with 6 small holes) for 1-week conditioning to assess their physicochemical stability. HPLC tests and XRPD characterization were performed on the conditioned samples to detect changes in sample purity and crystal form. The XRPD results and HPLC results show no significant changes in sample crystal form and purity, and the test results are summarized in Table 31.

TABLE 31

Summary of stability test results for the three salt crystal forms

| Salt type (Sample number) | Starting sample HPLC purity (area %) | Stability conditions | Conditioned sample HPLC purity (area %) | Relative purity # (%) | Change of crystal form |
|---|---|---|---|---|---|
| Phosphate crystal form A | 98.63 | 40° C./75% RH | 98.51 | 99.9 | No change |
| | | 25° C./60% RH | 98.41 | 99.8 | No change |
| Maleate crystal form A | 98.70 | 40° C./75% RH | 97.97 | 99.3 | No change |
| | | 25° C./60% RH | 98.56 | 99.9 | No change |
| Methanesulfonate crystal form B | 97.97 | 40° C./75% RH | 97.95 | 100.0 | No change |
| | | 25° C./60% RH | 99.60 | 99.9 | No change |

#The relative purity is the ratio of the purity of the conditioned sample to the purityof the starting sample.

4. Hygroscopicity

Figure 51:
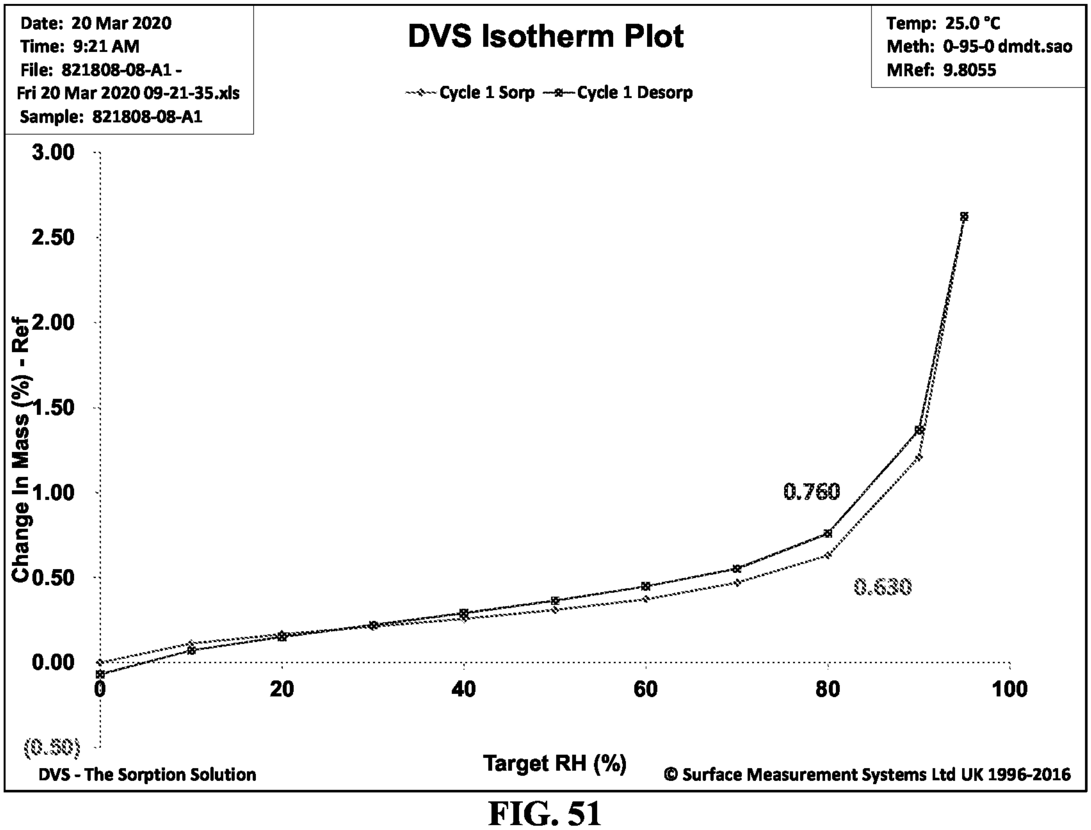
FIG. 51 illustrates a DVS plot for phosphate crystal form A of compound of formula (I).
Figure 52:
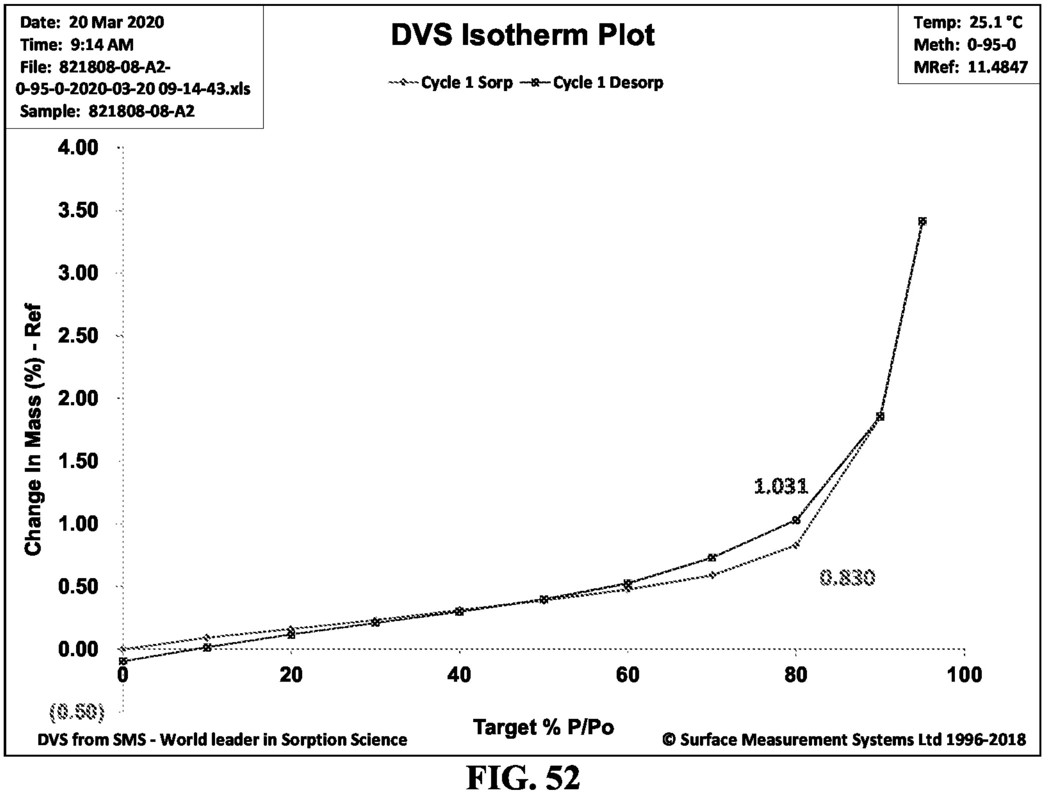
FIG. 52 illustrates a DVS plot for maleate crystal form A of compound of formula (I)
Figure 53:
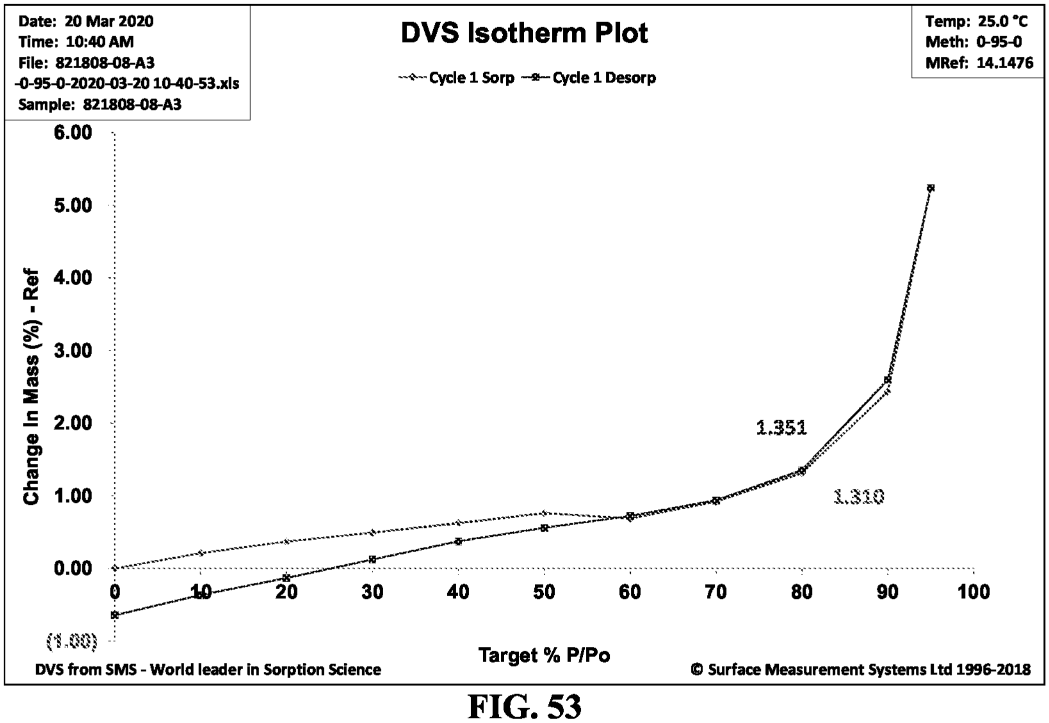
FIG. 53 illustrates a DVS plot for methanesulfonate crystal form B of compound of formula (I).

In order to evaluate hygroscopicity of the salt crystal forms, DVS tests were conducted on three samples. The results of DVS are shown in FIG. 51, FIG. 52 and FIG. 53. Phosphate crystal form A gained 0.6% by weight after absorbing moisture at 80% RH/25° C., maleate crystal form A gained 0.8% by weight after absorbing moisture at 80% RH/25° C., and methanesulfonate crystal form B gained 1.3% by weight after absorbing moisture at 80% RH/25° C., all of which were determined to be slightly hygroscopic. With the further increase of humidity in environment, it could be observed that the weight gains of these three samples after absorbing moisture were relatively more obvious. In addition, the XRPD results show that there was no change in the crystal form of the three batches of samples before and after the DVS test.

V. Conclusion (1) Salt-forming and salt crystal form screening tests were performed on(S)-(2-(6-(2-ethyl-5-fluoro-4-hydroxyphenyl)-1H-indazol-3-yl)-4,6-dihydropyrrolo[3,4-d] imidazol-5-(1H)-yl) (3-hydroxypyrrolidin-1-yl) methanone compounds of formula (I), and based on XRPD, TGA, DSC, NMR or HPLC/IC characterization results, a total of 10 different salt forms (involving 12 different crystal forms) were identified.

(2) Phosphate crystal form A, maleate crystal form A and methanesulfonate crystal form B of the compound of formula (I) were selected for in vitro evaluation in terms of hygroscopicity, solubility and solid stability based on the criteria of higher XRPD diffraction peak intensity, lower TGA weight loss, higher DSC melting temperature and higher safety level of acids.

(3) The phosphate crystal form A, maleate crystal form A and methanesulfonate crystal form B have a solubility range of 0.05-0.30 mg/mL in SGF, of 0.08-6.21 mg/mL in FeSSIF, of 0.04-1.30 mg/mL in water, of 1.14-2.14 mg/mL in ethanol and of 0.02-0.15 mg/mL in pH=7.4 phosphate buffer. The purity and crystal form of the three samples did not change significantly after they were placed at 40° C./75% RH and 25° C./60% RH for 1 week. The DVS results of the three samples show a weight gain of 0.6-1.3% after absorbing moisture, indicating that the samples are all slightly hygroscopic, and the results also show that the crystal forms remained unchanged after the DVS tests. In summary, all three salt crystal forms have good properties in terms of hygroscopicity and solid stability.

Example 6: Pharmacological Activity Evaluation of Compound of Formula (I)

1. Experimental Principle

A drug screening system based on kinases JAK1, JAK2, JAK3, and TYK2 was used to detect the inhibitory ability of small compounds on kinase activity. A kinase undergoes an enzymatic reaction with its substrates IRS1, IGF1Rtide, and Poly (4:1 Glu, Tyr), consuming ATP to produce ADP, wherein the ADP-Glo reagent and luminescence method can be used to detect the amount of the product to reflect the activity of the kinase.

2. Experimental Scheme 2.1 Experimental Materials and Instruments

| Item | Name | Source/Supplier | Catalogue No. |
|---|---|---|---|
| 1 | Tris | Sinopharm | 30188336 |
| 2 | DTT | Sigma | 43816 |
| 3 | MgCl2 | Sigma | M1028 |
| 4 | BSA | PE | CR84-100 |
| 5 | ADP-Glo Kinase Assay | Promega | V9101 |
| 6 | JAK1 | Thermofisher | PV4774 |
| 7 | JAK2 | Carna | 08-045 |
| 8 | JAK3 | Carna | 08-046 |
| 9 | TYK2 | Carna | 08-147 |
| 10 | ATP | Promega | V915B |
| 11 | IRS1 | Signalchem | I40-58-1000 |
| 12 | IGFIRtide | Signalchem | I15-58 |
| 13 | Poly (4:1 Glu, Tyr) | Sigma | P0275 |
| 15 | 384 polystyrene shallow flat white | Greiner | 784075 |
| 16 | 384-Well Polypropylene microplate | Labcyte | PP-0200 |
| 17 | Biotek Enzyme Labeler | Biotek | Synergy 4 |
| 18 | Microplate low-speed centrifuge | Xiang Zhi | TD5B |

2.2 Experimental Methods 2.2.1 Kinase Reaction Reagent Formulation 2.2.1.1 1× Kinase Reaction Buffer (6 mL)

| Name | Stock Concentration | Volume | Final Concentration |
|---|---|---|---|
| Tris | 1M (25X) | 240 μL | 40 mM |
| MgCl2 | 1M (50X) | 120 μL | 20 mM |
| BSA | 7.5% (75X) | 80 μL | 0.1% |
| DTT | 1M (500X) | 3 μL | 0.5 mM |
| ddH2O | | 5557 μL | |

2.2.1.2 2× Kinase Formulation

| Name | Stock concentration | Volume | 2X Final Concentration | Final Concentration |
|---|---|---|---|---|
| JAK1 kinase solution | | | | |
| JAK1 | 2667 nM | 7.5 μL | 33 nM | 16.7 nM |
| 1X Kinase Reaction Buffer | | 592.5 μL | | |
| JAK2 kinase solution | | | | |
| JAK2 | 4256 nM | 0.56 μL | 2 nM | 2 nM |
| 1X Kinase Reaction Buffer | | 599.44 μL | | |
| JAK3 kinase solution | | | | |
| JAK3 | 3195 nM | 0.75 μL | 4 nM | 2 nM |
| 1X Kinase Reaction Buffer | | 599.25 μL | | |
| TYK2 kinase solution | | | | |
| TYK2 | 3174 nM | 3 μL | 16 nM | 8 nM |
| 1X Kinase Reaction Buffer | | 597 μL | | |

2.2.1.3 4× Substrate Mixture Formulation

| Name | Stock concentration | Volume | 2X Final Concentration | Final Concentration |
|---|---|---|---|---|
| JAK1 substrate mixture solution | | | | |
| ATP | 10 mM | 2.4 μL | 80 μM | 20 μM |
| IRS1 | 1 mg/mL | 60 μL | 0.2 mg/mL | 0.05 mg/mL |
| 1X Kinase Reaction Buffer | | 237.6 μL | | |
| JAK2 substrate mixture solution | | | | |
| ATP | 10 mM | 6 μL | 20 μM | 5 μM |
| IGFIRtide | 1 mg/mL | 12 μL | 0.04 mg/mL | 0.01 mg/mL |
| 1X Kinase Reaction Buffer | | 287.4 μL | | |
| JAK3 substrate mixture solution | | | | |
| ATP | 10 mM | 1.2 μL | 40 μM | 10 μM |
| Poly (4:1 Glu, Tyr) Peptide | 6 mg/mL | 6 μL | 0.12 mg/mL | 0.03 mg/mL |
| 1X Kinase Reaction Buffer | | 292.8 μL | | |
| TYK2 substrate mixture solution | | | | |
| ATP | 10 mM | 1.2 μL | 40 μM | 10 μM |
| IRS1 | 1 mg/mL | 60 μL | 0.08 mg/mL | 0.02 mg/mL |
| 1X Kinase Reaction Buffer | | 238.8 μL | | |

2.2.1.4 Compounds to be Tested

| Name | Molecular weight | Mass/ mg | Purity | Stock Concentration/ mM |
|---|---|---|---|---|
| Methanesulfonate of Compound of formula (I) | 572.61 | 2.6 | 99% | 10 |

2.2.2 Kinase Reaction Experiment Procedure 2.2.2.1 JAK1 & JAK2 Kinase Reaction Experimental Procedure a) Diluting Tofacitinib and compound to be tested (10 mM stock solution) by 50 times with 100% DMSO as diluent to perform a series of dilutions at a ratio of 1:3 in a 96-well dilution plate. Taking out 1 μL of the compound and adding it to 49 μL of kinase reaction buffer, and shaking the resulting mixture on a microplate shaker for 20 minutes.

b) Transferring 2 μL of kinase (prepared according to 2.2.1.2) to a 384-well reaction plate, adding 1 μL of the compound solution to be tested (prepared in step a) to the 384-well reaction plate (Greiner, 784075), centrifuging it at 1000 rpm/min for 1 min and incubating it at 25° C. for 10 min.

c) Transferring 1 μL of the substrate mixture (prepared according to 2.2.1.3) to the 384-well reaction plate, centrifuging it at 1000 rpm/min for 1 min, and incubating it at 25° C. for 60 min. In the reaction system, the final concentrations of Tofacitinib and the compound to be tested: 1000, 250, 62.5, 15.625, 3.906, 0.977, 0.244, 0.061, 0.015, 0.0038, nM, with a final DMSO concentration of 0.5%.

d) Transferring 4 μL of ADP-Glo to the 384-well reaction plate, centrifuging it at 1000 rpm/min for 1 min, and incubating it at 25° C. for 40 min.

e) Transferring 8 μL of Detection solution to the 384-well reaction plate, centrifuging it at 1000 rpm/min for 1 min, and incubating it at 25° C. for 40 min.

f) Using Biotek multi-function plate reader to read the luminescence signal, the intensity of which is used to characterize the degree of kinase activity.

2.2.3 Experimental Data Processing Method

Compound inhibition rate (% inh)=(negative control−compound)/(negative control−positive control)*100%

Negative control: DMSO

Positive control: 1000 nM Tofacitinib

IC50 (half inhibitory concentration) of the compound can be obtained using the following nonlinear fitting formula:

$$Y=\text{Bottom}+(\text{Top}-\text{Bottom})/(1+10\hat{}((\text{Log IC50}-X)*\text{HillSlope}))$$

X: log value of the compound concentration

Y: Compound inhibition rate (% inh)

Z' factor calculation equation:

$$Z'=1-3(\text{SDmin}+\text{SDmax})/(\text{AVEmax}-\text{AVEmin})$$

in which:

Min is the RLU value of the positive control 10 μM/100 μM/30 μM Filgotinib, and Max is the RLU value of the negative control DMSO; and SD is the standard error, and AVE is the average value of RLU.

3. Results

The results of the test assays are shown in the following table.

| Assays | Compound | IC50 (nM) |
|---|---|---|
| JAK1 assay | Tofacitinib | 2.2 |
| | Methanesulfonate of Compound of formula (I) | 0.12 |
| JAK2 assay | Tofacitinib | 1.5 |
| | Methanesulfonate of Compound of formula (I) | 0.3 |
| JAK3 assay | Tofacitinib | 1.6 |
| | Methanesulfonate of Compound of formula (I) | 0.24 |
| TYK2 assay | Tofacitinib | 55 |
| | Methanesulfonate of Compound of formula (I) | 0.18 |

The test results show that similar to the compound of formula (I), methanesulfonate of the compound of formula (I) also has an inhibitory activity that is much higher than that of Tofacitinib, in particular by more than one order of magnitude higher than that of Tofacitinib for JAK1 and TYK2, and can effectively inhibit JAK1, JAK2, JAK3 and TYK2 at very low concentrations.

Although specific embodiments of the present disclosure have been illustrated and described, it does not mean that these embodiments illustrate and describe all possible implementation forms of the present disclosure. More precisely, the language used in this specification are only descriptive words and not restrictive. It will be obvious to those skilled in the art that various kinds of changes and modifications can be made without departing from the general scope of the present disclosure. Therefore, the appended claims are intended to include all these changes and modifications within the scope of the present disclosure.

What is claimed is:

1. A crystal form of a pharmaceutically acceptable salt of a compound of formula (I):

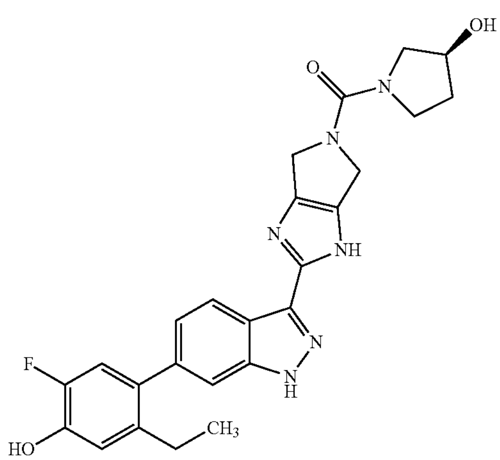

(I)

wherein the crystal form of the pharmaceutically acceptable salt of the compound of formula (I) is selected from the group consisting of:

(1) the crystal form A of the benzenesulfonate salt of the compound of formula (I) characterized by an X-ray powder diffraction (XRPD) pattern comprising at least one characteristic peak at a diffraction angle (° 2θ) selected from the group consisting of 5.82°±0.10°, 6.74°±0.10°, 11.85°±0.10°, and 16.38°±0.10°;

(2) the crystal form B of the benzenesulfonate salt of the compound of formula (I) characterized by an X-ray powder diffraction (XRPD) pattern comprising at least one characteristic peak at a diffraction angle (° 2θ) selected from the group consisting of 4.93°±0.10°, 5.63°±0.10°, 9.02°±0.10°, 10.89°±0.10°, 14.84°±0.10°, 17.55°±0.10°, 18.84°±0.10°, 23.12°±0.10°, 25.55°±0.10°, and 26.14°±0.10°;

(3) the crystal form A of the citrate salt of the compound of formula (I) characterized by an X-ray powder diffraction (XRPD) pattern comprising at least one characteristic peak at a diffraction angle (° 2θ) selected from the group consisting of 4.85°±0.10°, 6.42°±0.10°, 14.63°±0.10°, 17.12°±0.10°, 20.75°±0.10°, and 25.34°±0.10°;

(4) the crystal form B of the citrate salt of the compound of formula (I) characterized by an X-ray powder diffraction (XRPD) pattern comprising at least one characteristic peak at a diffraction angle (° 2θ) selected from the group consisting of 4.96°±0.10°, 7.67°±0.10°, 10.20°±0.10°, 11.04°±0.10°, 14.73°±0.10°, 19.23°±0.10°, 22.86°±0.10°, 23.54°±0.10°, 24.28°±0.10°, and 25.08°±0.10°;

(5) the crystal form A of the fumarate salt of the compound of formula (I) characterized by an X-ray powder diffraction (XRPD) pattern comprising at least one characteristic peak at a diffraction angle (° 2θ) selected from the group consisting of 4.96°±0.10°, 7.66°±0.10°, 10.21°±0.10°, 11.06°±0.10°, 14.74°±0.10°, 16.11°±0.10°, 22.87°±0.10°, and 25.10°±0.10°;

(6) the crystal form A of the hydrochloride salt of the compound of formula (I) characterized by an X-ray powder diffraction (XRPD) pattern comprising at least one characteristic peak at a diffraction angle (° 2θ)

selected from the group consisting of 8.05°±0.10°, 17.11°±0.10°, 18.02°±0.10°, 20.84°±0.10°, 21.09°±0.10°, 22.77°±0.10°, and 23.14°±0.10°;

(7) the crystal form A of the maleate salt of the compound of formula (I) characterized by an X-ray powder diffraction (XRPD) pattern comprising at least one characteristic peak at a diffraction angle (° 2θ) selected from the group consisting of 4.55°±0.10°, 8.78°±0.10°, 12.69°±0.10°, 13.96°±0.10°, 16.62°=0.10°, 17.61°±0.10°, 18.32°±0.10°, 25.39°±0.10°, and 26.53°±0.10°;

(8) the crystal form B of the methanesulfonate salt of the compound of formula (I) characterized by an X-ray powder diffraction (XRPD) pattern comprising at least one characteristic peak at a diffraction angle (°20) selected from the group consisting of 5.91°±0.10°, 9.22°±0.10°, 15.83°±0.10°, 17.73°±0.10°, 19.02°±0.10°, and 25.01°±0.10°;

(9) the crystal form A of the mucolate salt of the compound of formula (I) characterized by an X-ray powder diffraction (XRPD) pattern comprising at least one characteristic peak at a diffraction angle (° 2θ) selected from the group consisting of 4.98°±0.10°, 10.22°±0.10°, 11.07°±0.10°, 14.75°±0.10°, 14.94°±0.10°, 16.13°±0.10°, 19.65°±0.10°, and 30.79°±0.10°;

(10) the crystal form A of the phosphate salt of the compound of formula (I) characterized by an X-ray powder diffraction (XRPD) pattern comprising at least one characteristic peak at a diffraction angle (° 2θ) selected from the group consisting of 5.29°±0.10°, 7.47°±0.10°, 10.61°±0.10°, 19.16°±0.10°, and 21.32°±0.10°;

(11) the crystal form A of the tartrate salt of the compound of formula (I) characterized by an X-ray powder diffraction (XRPD) pattern comprising at least one characteristic peak at a diffraction angle (° 2θ) selected from the group consisting of 7.90°±0.10°, 8.69°±0.10°, 13.12°±0.10°, 13.43°±0.10°, 18.11°=0.10°, 21.28°±0.10°, and 22.90°±0.10°; and

(12) the crystal form A of the p-toluenesulfonate salt of the compound of formula (I) characterized by an X-ray powder diffraction (XRPD) pattern comprising at least one characteristic peak at a diffraction angle (°20) selected from the group consisting of 5.90°±0.10°, 9.34°±0.10°, 14.87°±0.10°, 15.33°±0.10°, 17.88°±0.10°, 18.76°±0.10°, 19.71°±0.10°, and 24.26°±0.10°.

2. The crystal form according to claim 1, wherein the crystal form is crystal form A of the benzenesulfonate salt of the compound of formula (I) characterized by an X-ray powder diffraction (XRPD) pattern comprising at least one characteristic peak at a diffraction angle (° 2θ) selected from the group consisting of 5.82°±0.10°, 6.74°±0.10°, 11.85°±0.10°, and 16.38°±0.10°.

3. The crystal form according to claim 2, wherein the crystal form is further characterized by an X-ray powder diffraction (XRPD) pattern comprising at least one additional characteristic peak at a diffraction angle (° 2θ) selected from the group consisting of 19.46°±0.10° and 20.20°±0.10°.

4. The crystal form according to claim 1, wherein the crystal form is crystal form B of the benzenesulfonate salt of the compound of formula (I) characterized by an X-ray powder diffraction (XRPD) pattern comprising at least one characteristic peak at a diffraction angle (° 2θ) selected from the group consisting of 4.93°±0.10°, 5.63°±0.10°, 9.02°±0.10°, 10.89°±0.10°, 14.84°±0.10°, 17.55°±0.10°, 18.84°±0.10°, 23.12°±0.10°, 25.55°±0.10°, and 26.14°±0.10°.

5. The crystal form according to claim 4, wherein the crystal form is further characterized by an X-ray powder diffraction (XRPD) pattern comprising at least one additional characteristic peak at a diffraction angle (° 2θ) selected from the group consisting of 10.30°±0.10°, 11.43°±0.10°, 14.23°±0.10°, 17.04°±0.10°, 19.66°±0.10°, 20.24°±0.10°, 22.71°±0.10°, and 24.91°±0.10°.

6. The crystal form according to claim 1, wherein the crystal form is crystal form A of the citrate salt of the compound of formula (I) characterized by an X-ray powder diffraction (XRPD) pattern comprising at least one characteristic peak at a diffraction angle (° 2θ) selected from the group consisting of 4.85°±0.10°, 6.42°±0.10°, 14.63°±0.10°, 17.12°±0.10°, 20.75°±0.10°, and 25.34°±0.10°.

7. The crystal form according to claim 6, wherein the crystal form is further characterized by an X-ray powder diffraction (XRPD) pattern comprising at least one additional characteristic peak at a diffraction angle (° 2θ) selected from the group consisting of 7.64°±0.10°, 15.40°±0.10°, 18.12°±0.10°, 18.84°±0.10°, and 19.37°±0.10°.

8. The crystal form according to claim 1, wherein the crystal form is crystal form B of the citrate salt of the compound of formula (I) characterized by an X-ray powder diffraction (XRPD) pattern comprising at least one characteristic peak at a diffraction angle (° 2θ) selected from the group consisting of 4.96°±0.10°, 7.67°±0.10°, 10.20°±0.10°, 11.04°±0.10°, 14.73°±0.10°, 19.23°±0.10°, 22.86°±0.10°, 23.54°±0.10°, 24.28°±0.10°, and 25.08°±0.10°.

9. The crystal form according to claim 8, wherein the crystal form is further characterized by an X-ray powder diffraction (XRPD) pattern comprising at least one additional characteristic peak at a diffraction angle (° 2θ) selected from the group consisting of 12.42°±0.10°, 16.09°±0.10°, 17.55°±0.10°, and 27.91°±0.10°.

10. The crystal form according to claim 1, wherein the crystal form is crystal form A of the fumarate salt of the compound of formula (I) characterized by an X-ray powder diffraction (XRPD) pattern comprising at least one characteristic peak at a diffraction angle (° 2θ) selected from the group consisting of 4.96°±0.10°, 7.66°±0.10°, 10.21°±0.10°, 11.06°±0.10°, 14.74°±0.10°, 16.11°±0.10°, 22.87°±0.10°, and 25.10°±0.10°.

11. The crystal form according to claim 10, wherein the crystal form is further characterized by an X-ray powder diffraction (XRPD) pattern comprising at least one additional characteristic peak at a diffraction angle (° 2θ) selected from the group consisting of 12.44°±0.10°, 19.25°±0.10°, 23.54°±0.10°, 24.27°±0.10°, and 25.37°±0.10°.

12. The crystal form according to claim 1, wherein the crystal form is crystal form A of the hydrochloride salt of the compound of formula (I) characterized by an X-ray powder diffraction (XRPD) pattern comprising at least one characteristic peak at a diffraction angle (° 2θ) selected from the group consisting of 8.05°±0.10°, 17.11°±0.10°, 18.02°±0.10°, 20.84°±0.10°, 21.09°±0.10°, 22.77°±0.10°, and 23.14°±0.10°.

13. The crystal form according to claim 12, wherein the crystal form is further characterized by an X-ray powder diffraction (XRPD) pattern comprising at least one additional characteristic peak at a diffraction angle (° 2θ)

selected from the group consisting of 15.04°±0.10°, 20.44°±0.10°, and 22.07°±0.10°.

14. The crystal form according to claim 1, wherein the crystal form A of the maleate salt of the compound of formula (I) characterized by an X-ray powder diffraction (XRPD) pattern comprising at least one characteristic peak at a diffraction angle (° 2θ) selected from the group consisting of 4.55°±0.10°, 8.78°±0.10°, 12.69°±0.10°, 13.96°±0.10°, 16.62°±0.10°, 17.61°±0.10°, 18.32°±0.10°, 25.39°±0.10°, and 26.53°±0.10°.

15. The crystal form according to claim 14, wherein the crystal form is further characterized by an X-ray powder diffraction (XRPD) pattern comprising at least one additional characteristic peak at a diffraction angle (° 2θ) selected from the group consisting of 13.74°±0.10° and 21.72°±0.10°.

16. The crystal form according to claim 1, wherein the crystal form is crystal form B of the methanesulfonate salt of the compound of formula (I) characterized by an X-ray powder diffraction (XRPD) pattern comprising at least one characteristic peak at a diffraction angle (° 2θ) selected from the group consisting of 5.91°±0.10°, 9.22°±0.10°, 15.83°±0.10°, 17.73°±0.10°, 19.02°±0.10°, and 25.01°±0.10°.

17. The crystal form according to claim 16, wherein the crystal form is further characterized by an X-ray powder diffraction (XRPD) pattern comprising at least one additional characteristic peak at a diffraction angle (° 2θ) selected from the group consisting of 20.61°±0.10°, 21.36°±0.10°, and 23.18°±0.10°.

18. The crystal form according to claim 1, wherein the crystal form is crystal form A of the mucolate salt of the compound of formula (I) characterized by an X-ray powder diffraction (XRPD) pattern comprising at least one characteristic peak at a diffraction angle (2θ) selected from the group consisting of 4.98°±0.10°, 10.22°±0.10°, 11.07°±0.10°, 14.75°±0.10°, 14.94°±0.10°, 16.13°±0.10°, 19.65°±0.10°, and 30.79°=0.10°.

19. The crystal form according to claim 18, wherein the crystal form is further characterized by an X-ray powder diffraction (XRPD) pattern comprising at least one additional characteristic peak at a diffraction angle (° 2θ) selected from the group consisting of 7.69°±0.10°, 21.51°±0.10°, and 22.92°±0.10°.

20. The crystal form according to claim 1, wherein the crystal form is crystal form A of the phosphate salt of the compound of formula (I) characterized by an X-ray powder diffraction (XRPD) pattern comprising at least one characteristic peak at a diffraction angle (° 2θ) selected from the group consisting of 5.29°±0.10°, 7.47°±0.10°, 10.61°±0.10°, 19.16°±0.10°, and 21.32°±0.10°.

21. The crystal form according to claim 20, wherein the crystal form is further characterized by an X-ray powder diffraction (XRPD) pattern comprising at least one additional characteristic peak at a diffraction angle (° 2θ) selected from the group consisting of 15.94°±0.10°, 16.77°±0.10°, 18.68°±0.10°, and 25.36°±0.10°.

22. The crystal form according to claim 1, wherein the crystal form is crystal form A of the tartrate salt of the compound of formula (I) characterized by an X-ray powder diffraction (XRPD) pattern comprising at least one characteristic peak at a diffraction angle (° 2θ) selected from the group consisting of 7.90°±0.10°, 8.69°±0.10°, 13.12°±0.10°, 13.43°±0.10°, 18.11°±0.10°, 21.28°±0.10°, and 22.90°±0.10°.

23. The crystal form according to claim 22, wherein the crystal form is further characterized by an X-ray powder diffraction (XRPD) pattern comprising at least one additional characteristic peak at a diffraction angle (° 2θ) selected from the group consisting of 15.08°±0.10°, 17.17°±0.10°, 17.44°±0.10°, 19.40°±0.10°, 20.74°±0.10°, 24.15°±0.10°, and 24.95°±0.10°.

24. The crystal form according to claim 1, wherein the crystal form is crystal form A of the p-toluenesulfonate salt of the compound of formula (I) characterized by an X-ray powder diffraction (XRPD) pattern comprising at least one characteristic peak at a diffraction angle (° 2θ) selected from the group consisting of 5.90°±0.10°, 9.34°±0.10°, 14.87°±0.10°, 15.33°±0.10°, 17.88°±0.10°, 18.76°±0.10°, 19.71°±0.10°, and 24.26°±0.10°.

25. The crystal form according to claim 24, wherein the crystal form is further characterized by an X-ray powder diffraction (XRPD) pattern comprising at least one additional characteristic peak at a diffraction angle (° 2θ) selected from the group consisting of 12.99°±0.10°, 16.10°±0.10°, 19.34°±0.10°, 20.39°=0.10°, and 24.99°±0.10°.

26. A pharmaceutical composition comprising at least one pharmaceutically acceptable carrier, adjuvant, or excipient and the crystal form according to claim 1.

27. The pharmaceutical composition according to claim 26, wherein the pharmaceutical composition is formulated as a dispersion.

28. The pharmaceutical composition according to claim 27, wherein the dispersion comprises a pharmaceutically acceptable medium.

29. The pharmaceutical composition according to claim 28, wherein the pharmaceutically acceptable medium disperses the crystal form.

30. The pharmaceutical composition according to claim 26, wherein the pharmaceutical composition is formulated as a solution.

31. The pharmaceutical composition according to claim 30, wherein the solution comprises a pharmaceutically acceptable solvent.

32. The pharmaceutical composition according to claim 31, wherein the pharmaceutically acceptable solvent dissolves the crystal form.

* * * * *